United States Patent
Butler et al.

(10) Patent No.: US 7,326,828 B2
(45) Date of Patent: Feb. 5, 2008

(54) PHOSPHOLIPID:DIACYLGLYCEROL ACYLTRANSFERASES

(75) Inventors: Karlene H Butler, Newark, DE (US); Rebecca E Cahoon, Webster Grove, MO (US); Omolayo O Famodu, Newark, DE (US); Sarah E Hall, Thorndale, PA (US); Edgar B Cahoon, Webster Grove, MO (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 105 days.

(21) Appl. No.: 11/315,766

(22) Filed: Dec. 22, 2005

(65) Prior Publication Data

US 2006/0101544 A1    May 11, 2006

Related U.S. Application Data

(62) Division of application No. 10/321,802, filed on Dec. 17, 2002, now Pat. No. 7,053,269.

(60) Provisional application No. 60/341,448, filed on Dec. 17, 2001.

(51) Int. Cl.
| | | |
|---|---|---|
| *A01H 1/00* | (2006.01) | |
| *C07H 21/04* | (2006.01) | |
| *C12N 15/29* | (2006.01) | |
| *C12N 15/52* | (2006.01) | |
| *C07K 14/415* | (2006.01) | |

(52) U.S. Cl. .................. 800/295; 435/6; 435/69.1; 435/468; 435/419; 435/252.3; 435/320.1; 435/183; 530/370; 536/23.6; 800/278

(58) Field of Classification Search ............ 435/6, 435/69.1, 468, 419, 252.3, 320.1, 183; 530/370; 536/23.6; 800/278
See application file for complete search history.

(56) References Cited

U.S. PATENT DOCUMENTS 7,157,619 B1 *   1/2007   Lassner et al. ............ 800/281

* cited by examiner

*Primary Examiner*—Phuong T Bui

(57) ABSTRACT

This invention relates to an isolated nucleic acid fragment encoding an acyltransferase, more specifically a phospholipid:diacylglycerol acyltransferase. The invention also relates to the construction of a recombinant DNA construct encoding all or a portion of the phospholipid:diacylglycerol acyltransferase, in sense or antisense orientation, wherein expression of the recombinant DNA construct results in production of altered levels of the phospholipid:diacylglycerol acyltransferase in a transformed host cell.

11 Claims, 11 Drawing Sheets

Figure 1A

```
                              +----+----+----+----+----+----+
                                  10        20        30        40        50        60
                              +----+----+----+----+----+----+
SEQ ID NO:30  ---------------MPLIHRKKPTEKPSTPPSEEVVHDEDSQKK----------PHESSKSHHKKSNGGG    46
SEQ ID NO:16  ------------------------------------------------------------------------     0
SEQ ID NO:18  MSLLRRRKQPQHPDPTPD----EENEEKEQK------------------------------------------    37
SEQ ID NO:20  MSFLRRRK-----PLPPSDGDESDHDDNDKGKK--------------------------AFKKQAKTN        44
SEQ ID NO:22  MSLLRRRKQPQPPEQPNEDSSNGSDLDEKGKKKPGSSSSSAAPPPEAAAAAKEATKRT                    60
SEQ ID NO:24  MSLLRRRKGSEPEKGPSPSSEPKVLSEDETEDDK------------------PSSSSGSPSKEPTKRT           49
SEQ ID NO:26  MALLRRRKQPDSDPHPDPGQDPKPDEEDDKEQK--------------------NNKKNKKKRDEVGEK           42
SEQ ID NO:28  L-----------------------------------------------------ASKKSNKNG                6
SEQ ID NO:36  MSLLRRRKGSEPEKGPSPSSEPKVLSEDETEDDK-------------------VPNS                     49
                                                                     NNKKNKKKRDEVGE

+----+----+----+----+----+----+
                                  70        80        90       100       110       120
                              +----+----+----+----+----+----+
SEQ ID NO:30  K---WSCIDSCCWFIGCVCVTWWFLLFLYNAMPASFPQYVTERITGPLPDPPGVKLKKEG                 103
SEQ ID NO:16  ------------------------------------------------------------                   0
SEQ ID NO:18  KTKNYTCLDNCCWFVGCVCSVWWLLLFLYNAMPASFPQFVTEAISGPVPDPPGVKCLKEG                 97
SEQ ID NO:20  KAK-WSCVDSCCWLVGCVCSAWWLLLFLYNAMPASFPQFVTEAITGPLPDPPGVKLQKEG                 103
SEQ ID NO:22  RAR-WSCVDSCCWLVGCVCSAWWLLLFLYNAMPASFPQYVTEAITGPLPDPPGVKLQKEG                 119
SEQ ID NO:24  KKNKWSCFDSCCWWVGCICTLMWFLLFLYQMMPSSIPQYVTEAFTGPMPDPPGLKLKKEG                 109
SEQ ID NO:26  KIKNYSCLDNCCWFVGCVCSVWWLLLFLYNAMPASFPQFVTEAISGPFPDPPGVKCLKEG                 102
SEQ ID NO:28  RA----------------------------------------EAITGPLPDPPGVKLQKEG                 27
SEQ ID NO:36  KKNKWSCFDSCCWWVGCICTLWCFLLFLYQMPSSIPQYVTEAFTGPMPDPPGLKLKKEG                  109
```

Figure 1B

```
                  130        140        150        160        170        180
                   +----+----+----+----+----+----+----+----+----+----+----+
SEQ ID NO:30       LKAKHPVVFIPGIVTGGLELWEGKQCADGLFRKRLWGGTFGEVYKRPLCWVEHMSLDNET   163
SEQ ID NO:16                                                                 0
SEQ ID NO:18       LKAKHPVVFVFVPGIVTGGLELWEGHQCMDGLFRKRLWGGTFGEVYKRPSCWVQHMSLDNKT  157
SEQ ID NO:20       LRAKHPVVFVFVPGIVTGGLELWEGHQCAEGLFRKRLWGGTFGDVYKRPLCWVEHMSLDNET  163
SEQ ID NO:22       LRAKHPVVFVFVPGIVTGGLELWEGHQCAEGLFRKRLWGGTFGDVYKRPLCWVEHMSLDNET  179
SEQ ID NO:24       LKVKHPVVFVFVPGIVTGGLELWEGHLCAEGLFRKRLWGGTFGEVYKRPSCWVDHMSLDNET  169
SEQ ID NO:26       LKAKHPVVFVFVPGIVTGGLELWEGHQCMDGLFRKRLWGGTFGEVYKRPSCWVQHMSLDNKT  162
SEQ ID NO:28       LHAKHPVIFVFVPGIVTGGLELWEGHHCAEGLFRKRLWGGTFGDVYKRPLCWIEHMSLDNET  87
SEQ ID NO:36       LKVKHPVVFVFVPGIVTGGLELWEGHLCAEGLFRKRLWGGTFGEVYKRPSCWVDHMSLDNET  169

190        200        210        220        230        240
                   +----+----+----+----+----+----+----+----+----+----+----+
SEQ ID NO:30       GLDPAGIRVRAVSGLVAADYFAPGYFVWAVLIANLAHIGYEEKNMYMAAYDWRLSFQNTE   223
SEQ ID NO:16                                                                 0
SEQ ID NO:18       GMDPPGIRVRPVSGLVAADYFAPGYFVPGYFVPGYFVWAVLIANLARVGYEEKNMYMAAYDWRLSFQNTE   217
SEQ ID NO:20       GLDKPGIRVRPVSVTGLVAADYFVPGYFVWAVLIANLARIGYEEKTMYMAAYDWRLSFQNTE   223
SEQ ID NO:22       GLDKPGIRVRPVTGLVAADYFVPGYFVWAVLIANLARIGYEEKTMYMAAYDWRLSFQNTE   239
SEQ ID NO:24       GLDPPGIRVRPVSGLVAADYFAAGYFVPGYFVWAVLIANLARIGYEEKTMYMAAYDWRLSFQNTE   229
SEQ ID NO:26       GMDPPGIRVRPVSGLVAADYFAPGYFVPGYFVWAVLIANLARVGYEEKNMYMAAYDWRLSFQNTE   222
SEQ ID NO:28       GLDKPGIRVRPVTGLVAADYFVPGYFVWAVLIANLARIGYEEKTMYMAAYDWRLSFQNTE   147
SEQ ID NO:36       GLDPPGIRVRPVSGLVAADYFAAGYFVWAVLIANLARIGYEEKTMYMAAYDWRIAFQNTE   229
```

Figure 1C

```
                        250         260         270         280         290         300
                ----+----|----+----|----+----|----+----|----+----|----+----|
SEQ ID NO:30                                                                              283
SEQ ID NO:16                                                                                0
SEQ ID NO:18    VRDQTLSRIKSNIELMVATNGGKKAVIIPHSMGVIYFLHFMKWVEAPAPMGGGGGPDWCA              277
SEQ ID NO:20    VRDQTLSRIKSNIELMVATNGGNRVVIPHSMGVLYFLHFMKWVEAPPPMGGGGPNWCE              283
SEQ ID NO:22    VRDQTLSRIKSNIELLVATNGGNRVVIPHSMGVLYFLHFMKWVEAPPPMGGGGGPNWCA             299
SEQ ID NO:24    VRDQTLSRIKSNIELMVATNGGNKAVIIPHSMGVLYFLHFMKWVEAPAPMGGGGGPDWCS            289
SEQ ID NO:26    VRDQTLSRIKSNIELMVATNGGKKAVIIPHSMGVLYFLHFMKWVEAPAPMGGGGGPDWCA            282
SEQ ID NO:28    TRDQTLSRIKSNIELLVATNGGNRAVVIPHSMGVLYFLHFMKWVEAPSPMGGGGGPDWCA            207
SEQ ID NO:36    VRDQTLSRIKSNIELMVATNGGNKAVIIPHSMGVLYFLHFMKWVEAPAPTGGGGPDWCS             289

310         320         330         340         350         360
                ----+----|----+----|----+----|----+----|----+----|----+----|
SEQ ID NO:30    KYIKAVMNIGGPFLGVPKAVAGLFSAEEAKDVAVARAIAPGFLDTDIFRLQTLQHVMRMTR            343
SEQ ID NO:16    -HIKAVMNIGGPFLGVPKSVAGLFSLEARDIAVARAEAPGVLDKDVFGLQTLLHLMRMTR             59
SEQ ID NO:18    KHIKAVMNIGGPFLGVPKAVAGLFSAEAKDIASVRALAPGMLDSDLFQIQTLQHIMRMSR            337
SEQ ID NO:20    KHIKAVMNIGGPFLGVPKAVAGLFSSEAKDIAVARAIAPDVLDSDFLGLQTLRHLMRMTR            343
SEQ ID NO:22    KHIKSVMNIGGPFLGVPKAVAGLFSSEAKDIAVARAIAPEVLDSDFLGLQTLRHLMRMTR            359
SEQ ID NO:24    KYIKAVMNIGGPFLGVPKAIAGLFSAEARDIAVARTIAPGFLDNDLFRIQTLQHVMKMTR            349
SEQ ID NO:26    KHIKAVMNIGGPFLGVPKAVAGLFSAEAKDIASVRALAPGVLDSDLFQIQTLQHVMRMSR            342
SEQ ID NO:28    KHIKAVANIGGPFLGVPKAVAGLFSSEAKDVAVARAIAPEMLDSDFLGLQTLRHLMRMTR            267
SEQ ID NO:36    TYIKAVVNIGGPFLGVPKAIAGLFSAEARDIAVARTIAPGFLDNDLFRIQTLQHVMKMTR            349
```

Figure 1D

```
                      370       380       390       400       410       420
                        +---------+---------+---------+---------+---------+
SEQ ID NO:30  TWDSTMSMLPKGGDTIWGGLDWSPEKGHTCCGKKQKNNETCGEAGENGVS---KKSPVNY    400
SEQ ID NO:16  TWDSTMSMIPKGGDTIWGGLDWSPEGHYSCSAKKLKKNDTYNSFQNDKENLKF-VKSVNY    118
SEQ ID NO:18  TWDSTMSMIPKGGDTIWGGLDWSPEDGYSPSKRKHGKNDTESSTQNESASEECEVTHANY    397
SEQ ID NO:20  TWDSTMSMLPKGGDTIWGNLDWSPEDGLECKAKKHKTNDTEVSKDSNGENIEVQPEPINY    403
SEQ ID NO:22  TWDSTMSMIPKGGDTIWGDLDWSPEDGFECKAKNQKINDSEVSKDANGKN-EVHPEPVKY    418
SEQ ID NO:24  TWDSTMSMIPRGGDTIWGGLDWSPEEGYHPSQRKHSSDYTQLTDQETN-----QTNVVNY    404
SEQ ID NO:26  TWDSTMSMIPKGGDTIWGGLNWSPEEGYSPRRSKHGKNDTESPTVSDSAS---EVTHANY    399
SEQ ID NO:28  TWDSTMSMLPKGGDTIWGGLDWSPEDGFECKSKKRKTNDSEVSKDVHGEPVEVNPEPVNF    327
SEQ ID NO:36  TWDSTMSMIPRGGDTIWGGLDWSPEEGYHPSQRKHSNNNTQLKDHETN-----QTNFVNY    404

430       440       450       460       470       480
                        +---------+---------+---------+---------+---------+
SEQ ID NO:30  GRMISFGKEVAEAAPSEINNIDFRGAVKGQSIPNH--TCRDVWTEYHDMGIAGIKAIAEY    458
SEQ ID NO:16  GRLISFGKHIAELHSSKLERLDFRGALKGRNLANTS-SC-DVWTEYHEMGIEGIKAVLDY    176
SEQ ID NO:18  GRIVSFGRDVAEAPSSEIERIEFRGAVKGNNVANN--TCRAVWTEYHDMGFGGIKAVAEY    455
SEQ ID NO:20  GRLVSFGKDVAEAPSSEIEQIEFRDAVKGNDIVHSNASCREIWTEYHELGWGGIKAVADY    463
SEQ ID NO:22  GRIVSFGKDVAEAPSSEIEQIEFRDAVKGNNIAHSNTSCRDIWTEYHELGWGGIKAVADY    478
SEQ ID NO:24  GRMISFGRDVAEAHSSKIEMADFRGAIKGRSVA--NTTCRDVWTEYHEMGFEGVRAVAEH    462
SEQ ID NO:26  GRIVSFGRDVAEAPSSEIERIEFRGAVKGINVANN--TCRAVWTEYHDMGFGGIKAVAEY    457
SEQ ID NO:28  GRMVSFGKDVAEAPASNIEQIEFRDAVKGNNLAHSNTSCRDVWTEYQELGWGGIKAVSDY    387
SEQ ID NO:36  GRMISFGRDVAEAHSPEIQMTDFRGAIKGRSIA--NTTCRDVWTEYHEMGFEGVRAVAEH    462
```

Figure 1E

```
                      490       500       510       520       530       540
                 ----+---------+---------+---------+---------+---------+---------+
SEQ ID NO:30         KVYTAGEAIDLLHYVAPKMARGAAHFSYGIADDLDDTKYQDPKYWSNPLETKLPNAPEM   518
SEQ ID NO:16         KTYTADSVLDLLHYVAPKMKRGDAHFSHGIADNLDDEKYQHYKYWSNPLETRLPNAPDM   236
SEQ ID NO:18         KVYTAGEIVDMLEFVAPKMERGSAHFSYGIADNLDDPKYSHYKYWSNPLETKLPNAPDM   515
SEQ ID NO:20         KVYTASSVIDLLHFVAPRMMQRGNVHFSYGIADNLDDPKYQHYKYWSNPLETKLPNAPDM   523
SEQ ID NO:22         KVYTAGSIIDLLRFVAPRMMQRGSVHFSYGIADNLDDPKYGHYKYWSNPLETKLPNAPEM   538
SEQ ID NO:24         KVYTAGSIVELLQFVAPKMMARGSAHFSYEIADNLDDPKYNHYKYWSNPLETKLPNAPDM   522
SEQ ID NO:26         KVYTAGEIVELLEFVAPKMMERGSAHFSYGIADNLDDPKYTHYKYWSNPLETKLPNAPDM   517
SEQ ID NO:28         KAFTAGSIIDLFNFVAPRMMQRGSVHFSYGIADNLDDPKYGHYKYWSNPLETKLPDAPEM   447
SEQ ID NO:36         KVYTAGSVVDLLQFVAPKMMARGSAHFSYGIADNLDDPKYNHYKYWSNPLETKLPNAPDM   522
                 ----+---------+---------+---------+---------+---------+---------+
                      550       560       570       580       590       600
                 ----+---------+---------+---------+---------+---------+---------+
SEQ ID NO:30         EIYSLYGVGIPTERAYVYKLNQSPDSCIPFQIFTSAHEE-DEDSCLKAGVYNVDGDETVP   577
SEQ ID NO:16         EIYSMYGVGIPTERAYVYKFNPQSECQIPFQIDTSADGE-NEDSCLKDGVYCSDGDETVP   295
SEQ ID NO:18         EIYSMYGVGIPTERAYVYKLTPAAECYIPFQIDTSAKDK-NEDGCLKDGVYTVDGDETVP   574
SEQ ID NO:20         EIISMYGVGIPTERAYVYKLAPQAECYIPFRIDASADGG-EENKCLKGGVYLADGDETVP   582
SEQ ID NO:22         EIFSMYGVGIPTERAYVYKLAPQAECYIPFQIDASAEGG-DENSCLKGGVYLSNGDETVP   597
SEQ ID NO:24         EIYSMYGVGIPTERSYIYKLTPFAECYIPFEIDTTQDGGSDEDSCLQGGSDEDSCLKGGVYTVDGDETVP   582
SEQ ID NO:26         EIYSMYGVGIPTERAYVYKLTPAAECYIPFQIDTSAKDK-GEDGCLKDGVYTVDGDETVP   576
SEQ ID NO:28         EIFSMYGVGIPTERAYVYKLSPQAECYIPFQIDASAEGG-DENSCLKGGVYMSNGDETVP   506
SEQ ID NO:36         EIFSMYGVGLPTERSYIYKLTPFAECYIPFEIDTTQDGGSDEDSCLQGGVYTVDGDETVP   582
                 ----+---------+---------+---------+---------+---------+---------+
```

Figure 1F

```
                           610         620         630         640         650         660
                      ----+----|----+----|----+----|----+----|----+----|----+----|
SEQ ID NO:30   VLSAGYMCAKAWRGKTRFNPSGIKTYIREYNHSPPANLLEGRGTQSGAHVDIMGNFALIE    637
SEQ ID NO:16   VLSAGFMCAKGWRGKTRFNPSGIHTYIREYDHAPPANLLEGRGTQSGAHVDILGNFALIE    355
SEQ ID NO:18   ALSAGYMCAKGWRGKTRFNPSGIKTYVREYDHNPPSNFLEGRGTQSGAHVDIMGNFQLIE    634
SEQ ID NO:20   VLSAGYMCAKGWRGKTRFNPAGSKTYVREYSHSPPSTLLEGRGTQSGAHVDIMGNFALIE    642
SEQ ID NO:22   VLSSGYMCAKGWRGKTRFNPSGSKTYVREYSHSPPSNLLEGRGTQSGAHVDIMGNFALIE    657
SEQ ID NO:24   VLSSGYMCAKGWRGKTRFNPSGMRTYVREYDHSPPANLLEGRGTQSGAHVDIMGNFALIE    642
SEQ ID NO:26   ALSAGYMCAKAWRGKTRFNPSGIKTYVREYDHNPPSNFLEGRGTQSGAHVDIMGNFQLIE    636
SEQ ID NO:28   VLSSGYMCAKGWRGKTRFNPSGSKTYVREYSHSPPSNLLEGRGTQSGAHVDIMGNFALME    566
SEQ ID NO:36   VLSSGFMCAKGWRGKTRFNPSGIRTYVREYDHSPPANLLEGRGTQSGAHVDIMGNFALIE    642

670         680         690
                      ----+----|----+----|----+----|
SEQ ID NO:30   DIMRVAAGGNGSDIGHDQVHSGIFEWSERIDLKL                              671
SEQ ID NO:16   DIIRVAAGASGEDLGGDRVYSDIFKWSENINLKL                              389
SEQ ID NO:18   DVIKVAAGATGEELGGDQVYTGIFEWSEKINLEL                              668
SEQ ID NO:20   DIIRIAAGATGEEIGGDQVYSDIFKWSEKIKLKL                              676
SEQ ID NO:22   DIIRIAAGATGEELGGDQVYSDIFKWSDKIKLKL                              691
SEQ ID NO:24   DVIRVAAGAKGEDLGGDKVYSDIFKWSEKIKLPL                              676
SEQ ID NO:26   DVIKVAAGATGEELGGDQVYTGIFEWSEKINLKL                              670
SEQ ID NO:28   DIIRIAAGATGEEIGGDQVYSDIFKWSEKIKLKL                              600
SEQ ID NO:36   DVIRVAAGAKGEDLGGDKVYSDIFKWSEKIKLPL                              676
```

Figure 2A

```
                           10         20         30         40         50         60
                  ---------+---------+---------+---------+---------+---------+
SEQ ID NO:29      ----------------------------------------------------------------   0
SEQ ID NO:2       MSLLLEEIIRSVEALLKL-RNRNQEPYVDPNLNPVLLVPGIAGSILNAVDHENGNEERVW         59
SEQ ID NO:4       MAVLLEEIVKSVELWLRLIKKPQP--YVDPNLDPLLIPGVAGSILNAVNEDTGREERVW          58
SEQ ID NO:6       MAVLLVDVVKAVEAWLKILK--EPEPYVDPNLDPVLIVPGIAGSILHAKDAETGKEERVW         58
SEQ ID NO:8       MAVLLEDILQSVEQWLKIRKPQP--YVDPNLDPVLLVPGVAGSILHAVDGSNKGERVW           58
SEQ ID NO:10      MAVLLEEIAQSVEIWLKLIKKPQP--YVDPNLDPVLLVPGIAGSILKAVDD-NGRGERVW         57
SEQ ID NO:12      ----SLSR--------------------------------------------------------     4
SEQ ID NO:14      MSVL-EDLIRAIELWLRIAK--EQVPLVDPSLDPVLLVPGIGGSILEAVDEA-GNKERVW         56
SEQ ID NO:32      MAILLDEILQSLELWLKLIKKPQPEPYINPNLDPVLLVPGIGGSMLHAVSDSNGNRERVW         60
SEQ ID NO:34      MSVL-EDLIRAIELWLRIAK--EQVPLVDPSLDPVLLVPGIGGSILEAVDEA-GNKERVW         56

70         80         90        100        110        120
                  ---------+---------+---------+---------+---------+---------+
SEQ ID NO:29      VRIFGADHEFRTKMWSREDPSTGKTISLDPKTSIVVPQDRAGLHAIDVLDPDMIVGRESV        119
SEQ ID NO:2       VRILGADSKFRTELMSFYDSASGESVCFDPKTKIRVPDERSGLYAIDILDPDLMIGCDSI        118
SEQ ID NO:4       VRIWEADREFRAKLWCQFDSETGKTVSLDPNISIVVPEDRNGLYAIDCLDPNMIIGRDSV        118
SEQ ID NO:6       VRIFGADYKCRTKLWSREDPAVGKTVSLDPKTNIVVPEDRYGLYAIDVLDPDMVLGRDCV        118
SEQ ID NO:8       VRIIGADYKFRTKLWSREDPSTGQTVSLDPKTHIVVPEERYGLHAIDVLDPEMIIGRDCV        117
SEQ ID NO:10      ----------------IDCLDPDMLIGRDSV                                       15
SEQ ID NO:12      VRILAADHECREKLWAQFDASTGKTISVDEKIRITVPEDRYGLYAIDTLDPDLIIGDDSV        116
SEQ ID NO:14      VRFLGADYMLRTKLWSRYDPSTGKSISLDTNTTLIPEDRHGLYAIDVLDPDLVIGSESV         120
SEQ ID NO:32      VRILAADHECREKLWAQFDASTGKTISVDEKIRITVPEDRYGLYAIDTLDPDLIIGDDSV        116
SEQ ID NO:34      (same)                                                                116
```

Figure 2B

```
                          130       140       150       160       170       180
                   ----+----|----+----|----+----|----+----|----+----|----+----|
SEQ ID NO:29       YYFHEMIVEMIGWGFEEGKTLFGFGYDFRQSNRLQETLDQFAKKLETVYKASGEKKINVI  179
SEQ ID NO:2        YYFHDMIVEMTKWGFQEGKTLFGFGYDFRQSNRLPESLDRLAAKLEAVFSASGGKKINII  178
SEQ ID NO:4        CYFHDMINEMTSWGYQEGKTLFGFGYDFRQSNRLKETMDRLAAKLDAIYTASGGKKITVI  178
SEQ ID NO:6        YYFHDMIVEMIKWGFQEGKTLFGFGYDFRQSNRFQETMECLAAKLESVYNAAGGKKMTII  178
SEQ ID NO:8        YYFHDMIVEMMKWGFQEGKTLFGFGYDFRQSNRFQETLERFAAKLEAVYTASGGKKINII  177
SEQ ID NO:10       --------------KTLFGFGYDFRQSNRLSETLDRFSRKLESVYIASGEKKINLI       46
SEQ ID NO:12       CYFHEMINEMTSWGYLEGKTLFGFGYDFRQSNRLQETMDRLATKLESIYTSSGGKKINVI   75
SEQ ID NO:14       YYYHDMIVQMIKWGYQ                                              132
SEQ ID NO:32       YYFHDMIVEMRKWGYQEGKTLFGFGYDFRQSNRLQETIDRLAAKLESIYDAAGGKKINII  180
SEQ ID NO:34       YYYHDMIVQMIKWGYQEGKTLFGFGYDFRQSNRLSETLDKFSNKLESVYTASGGKKINLI  176

190       200       210       220       230       240
                   ----+----|----+----|----+----|----+----|----+----|----+----|
SEQ ID NO:29       SHSMGGLLVKCFMGLHSDVCKSLFLYSYSRSMYRIGLLLLHFEVSSLTCGTSDSTGDNY  239
SEQ ID NO:2        SHSMGGLLVKCFMCLRSEI-----------------------------FE-------KY  201
SEQ ID NO:4        THSMGGLLVKCFMSLHTDI-----------------------------FE-------KY  201
SEQ ID NO:6        SHSMGGLLVKCFMCLHSDI-----------------------------FA-------KY  201
SEQ ID NO:8        SHSMGGLLVKCFMSLHTDI-----------------------------FE-------KY  200
SEQ ID NO:10       THSMGGLLVKCFMSLHSDV-----------------------------FE-------KY   69
SEQ ID NO:12       THSMGGLLVKCFMSLHSDI-----------------------------FE-------KY   98
SEQ ID NO:14                                                                    132
SEQ ID NO:32       SHSMGGLLVKCFMCLQSDI-----------------------------FE-------KC  203
SEQ ID NO:34       THSMGGLLVKCFMSLHGDV-----------------------------FE-------KY  199
```

Figure 2C

```
                         250         260         270         280         290         300
                    ----+----|----+----|----+----|----+----|----+----|----+----|
SEQ ID NO:29        HTDWFRIIDS--GAPGYITSTLLNGMSFVNGWEQNFFVSKWSMHQL--SC----------     285
SEQ ID NO:2         VQNWIAIAAPFQGAPGYVTSTFVNGMSFVNGWKQNFFISKWSMHQLLIECPSIYELMGSP     261
SEQ ID NO:4         VKSWIAIAAPFQGAPGYVTSTLMNGMSFVEGWEANFFVSKWSMHQLLIECPSIYELMACL     261
SEQ ID NO:6         VKNWIAIAAPFQGAPGYVTSTFLNGMSFVDGWEQNFFISKWSMHQLLIECPSIYELMACP     261
SEQ ID NO:8         VQNWIAIAAPFQGAPGYISSTFLNGMSFVEGWEQNFFISKWSMHQLLIECPSIYELMACP     260
SEQ ID NO:10        IKSWIAIAAPFQGAPGYITTSLLNGMSFVEGWESRFFISKWSMQQLLLECPSIYELLANS     129
SEQ ID NO:12        VKNWIAIXAPFQGAPGYVTXTLLNGMSFVEGWEAYFXXSXWXMHQLLIECPSIYELMACL     158
SEQ ID NO:14                                                                         132
SEQ ID NO:32        VKNWVAIAAPFQGAPGCINSTLLNGMSFVDGWEQKVYISKWSMHQLLIECPSIYELMGCP     263
SEQ ID NO:34        VKSWVAIAAPFQGAPGYINSGLLNGMSFVEGWQSKFFISKWTMQQLLIECPSIYELLASS     259

310         320         330         340         350         360
                    ----+----|----+----|----+----|----+----|----+----|----+----|
SEQ ID NO:29        ------------------GERKRAMMEL----EPLMLF---------LSLT--             305
SEQ ID NO:2         DFNWQHIPLLEIWRQKHDDDGNPHNVLESYLLKESVEILTESLSTNAILHDGLTIPLPFN     321
SEQ ID NO:4         DYEWEHLPLLQIWKEIQDENGNSTPMLETFTPMESVSIFTQALSVNELSFDGVDIPLPFN     321
SEQ ID NO:6         NFTWEHAPVLEIWRKKLDDCGDTRMILESYTPSESVNIFAEALSSNTVDYDGESISLPFN     321
SEQ ID NO:8         DFQWEHNPLLEIWREKHDKDGNSNIVLESYSPEESVPIFKEALSSNTVNYDGLDIPLPFN     320
SEQ ID NO:10        TFQWEDTPYLQIWRQKLDTNGKKSAMLESYEPDEAIKMIREALSKHEIISDGMHIPLPLD     189
SEQ ID NO:12        DYEWEHDPLLQIWKEIQNDDGNSTTILETFTPVEAVSIFTQALSINELNYGGVDIPLPFN     218
SEQ ID NO:14                                                                         132
SEQ ID NO:32        NFHWQHIPLLELWRERHDSDGKSGIILESYPPCDSVEVLKQALVNNTVNYNGEDLPLPFN     323
SEQ ID NO:34        TYHWEDTPLLQIWKESLDDNGKKSAILESYEPDEAIKMIQKALSKHEIISDGNHIPLPLN     319
```

Figure 2D

```
                          370             380             390             400             410             420
                  ----+----|----+----|----+----|----+----|----+----|----+----|----+----|----+----|----+----|----+----|
SEQ ID NO:29      ---VAW-------------RALKFLRNLF-------RIIHYGNEKMPVKDLTNLRYFQP                                          341
SEQ ID NO:2       LEILKWANETREVLKNAKLPSQVKFY-NIYATGLETPTHTVCYGDAEKPVADLHNLRYIEP                                        380
SEQ ID NO:4       KEILQWANKTREILSSAKLPSSVKFY-NVYGTGLDTPQSVCYGSADSPVSNLLELPFLDA                                        380
SEQ ID NO:6       QEILKWAHETRRILSCAKVPPGVKFY-NIYATNLETPHSVCYGSEDMPVTDLQELQFYLP                                        380
SEQ ID NO:8       LEILQWACETRKILSCAKVPSQVKFY-NIYGMNLETPHSVCYGSVEEPVTDLEQLKFVQA                                        379
SEQ ID NO:10      MDILRWAKETQDVLCNAKLPKSVKFY-NIYGTDYDTAHTVRYGSEHHPISNLSDLLYTQS                                        248
SEQ ID NO:12      KEILHWANKTREILSSAKLPPNVKFY-NVYGTGRDTPQSVCYGSADSPVSDLQELPLLDA                                        277
SEQ ID NO:14                                                                                                          132
SEQ ID NO:32      TEILKWAKKTWEILSSAKLPPNVKFY-NIYGTNLETAHSICYGSADKPVSDLQQLRYYQP                                        382
SEQ ID NO:34      EDILIWAKETQDILSQAKLPKSVKFY-NIYGIDYDTAHTVCYGSKRHPISNLSHLLYTQ-                                        377

430             440             450             460             470             480
                  ----+----|----+----|----+----|----+----|----+----|----+----|----+----|----+----|----+----|----+----|
SEQ ID NO:29      -TYICVDGDGTVPMESAMADGLEAVARVGVPGEHRGILNDHRVFRMLKKWLNVGEPDPFY                                        400
SEQ ID NO:2       -NYIYVDGDGTVPVESAKADGLDAVARIGVPGEHQRVLRDHRVFRRLKHWLKAGDPDPFY                                        439
SEQ ID NO:4       -TYVNVEGDGTVPVESARADGLDAEARVGIPGEHRGILCDKHLFRIVKHWLKA-DHDPFY                                        438
SEQ ID NO:6       -DYICVDGDGTVPTESAKADGLEAVARVGVPGEHRGILCDHHVFRILKHWLKA-DSDPYY                                        438
SEQ ID NO:8       -QYVCVDGDGTVPVESAMADGLTAEARIGVPGEHRGILAEPHVFRILKHWLKAGDPDPYY                                        438
SEQ ID NO:10      GNYICVDGDGSVPVESAKADGLDAVARVGVAADHRGIVCDRHVFRIIQHWLHAGEPDPFY                                        308
SEQ ID NO:12      -TFINVDGDGTVPMESAKADGLDAEARVGIPGEHRGILLDKHLFRIVKHWLKA-DHDPFY                                        335
SEQ ID NO:14                                                                                                          132
SEQ ID NO:32      -KYVCVDGDGTVPVESAKADGLNAEARVGVPGEHRGILRDPHVFRILKHWLKAGDPDPFY                                        441
SEQ ID NO:34      GKYICVDGDGSVPAESAKADGLDAVARIGVAADHRGIVCDHRVFRIVQHWLHAGEPDPFY                                        437
```

Figure 2E

```
                          490        500        510        520        530        540
                   ----+----|----+----|----+----|----+----|----+----|----+----|
SEQ ID NO:29       NPVNDYVILPTTYEFEKFHEN--GLEVASVKESWDIISDDNNIGTT------GSTVNSIS      452
SEQ ID NO:2        DPLNDYVILPTAFEVESHVE--KGLQVAALKEEWEIISHDQNKTDELC--NDKPLVSSIM      495
SEQ ID NO:4        NPVNDYVILPTLFEITKHQDSKEGKEVISLKEEWEIVSKEQQDE--------PMIGSIS      489
SEQ ID NO:6        NPLNDYVILPTTFEMERHHE--KGMEVTSLKEEWEIISKDANDDQGEVTI--MPSVSTIT      494
SEQ ID NO:8        NPLNDYVILPTAFEMERHKE--RGLQVTSLKEEWEIISRDSNDEDNIIVNNGKPLVSSIA     496
SEQ ID NO:10       DPLNDYVILPTAFEIEKYHE--KHG-DITSVREDWEIISHRD-DESKRPAELP-PMFNTLS     364
SEQ ID NO:12       NPVNDYVILPTIFEIERHKE--KGLEVMSLKEEWELVSGDQEDDDTY--DNRKPMVGSIS     391
SEQ ID NO:14                                                                         132
SEQ ID NO:32       NPLNDYVILPTAFEMESHKE--KGLEVASLKEEWEIISKDQDEQQSNIA--EEMSLSTIS     497
SEQ ID NO:34       DPLNDYVVIPTIFEVEKHHE-KRG-DVTSVREDWEIISHTDGDEAKRLAELP-AMVGAMS     494

550        560        570        580
                   ----+----|----+----|----+----|----+----|
SEQ ID NO:29       VSQPGDDQNP-QAEAARATLTVQPQSDGRQHVELNAVSVSVDA                      493
SEQ ID NO:2        LSRVTEDCPSSRAEACATVVVHPQQDGKQHVELNAVSVSVDA                       537
SEQ ID NO:4        ASRVGDD-GC-EEEARATFVVHPQSNGKQNIQLNAVSVSVSAGGA                    530
SEQ ID NO:6        VSQ-DRGHQSYRAEACATVVHPQNEGKQQVELNALSVSVDA                        535
SEQ ID NO:8        VSD-QSSL----TEARATVTLHPQSEGKRHIELNAISVSATV                       533
SEQ ID NO:10       ASR--EGEDGSLEEAQATIFVHPESKGRQHVEVRAVGVTHDG                       404
SEQ ID NO:12       ASHVGDD-GSFDEVARATFIVHPQSNGKQHIELNAMSVTAGGA                      433
SEQ ID NO:14                                                                        132
SEQ ID NO:32       VSH--EGANQSCSEAHATVVVRPGDEGKQHIQLNVVAVSVDAS                      538
SEQ ID NO:34       ASC--EGKDGLMDEAQATVVVHPESGGRQHVEVRAVGVSHGG                       534
```

PHOSPHOLIPID:DIACYLGLYCEROL ACYLTRANSFERASES

This application is a divisional application of U.S. Application No. 10/321,802, filed Dec. 17, 2002, now U.S. Pat. No. 7,053,269 and hereby incorporated by reference in its entirety, which claims the benefit of U.S. Provisional Application No. 60/341,448, filed Dec. 17, 2001.

FIELD OF THE INVENTION

The field of invention relates to plant molecular biology, and more specifically, to nucleic acid fragments encoding phospholipid:diacylglycerol acyltransferases in plants and seeds.

BACKGROUND OF INVENTION

In eukaryotic cells triacylglycerols are quantitatively the most important storage form of energy. The main pathway for synthesis of triacylglycerol is believed to involve three sequential acyl-transfers from acyl-CoA to the glycerol backbone. Acyl-CoA:diacylglycerol acyltransferase (DAGAT, EC 2.3.1.20) uses fatty acyl-CoA (acyl donor) and 1,2-diacylglycerol (acyl acceptor) as substrates to catalyze the third and only committed step in triacylglycerol synthesis. DAGAT plays a fundamental role in the metabolism of cellular glycerolipids.

Until recently, it was believed that only DAGAT could carry out the final step in triacylglycerol biosynthesis. However, it has now been demonstrated that microsomal preparation of developing seeds from several plants (sunflower, *Helianthus annus*; castor bean, *Ricinus communis*; hawk's beard, *Crepis palaestina*) as well as microsomal preparations from yeast (*Saccharomyces cerevisiae*) catalyze triacylglycerol formation via the enzyme phospholipid:diacylglycerol acyltransferase (PDAT, EC 2.3.1.158, Registry Number 288587-47-3) (WO 2000060095; Dahlqvist et al., *Proc. Natl. Acad. Sci. USA* 97(12):6487-6492 (2000)). This enzyme differs from DAGAT by synthesising triacylglycerol using an acyl-CoA-independent mechanism. The specificity of the enzyme for the acyl group in the phospholipid varies with species, e.g., the enzyme from castor bean preferentially incorporates vernoloyl (12,13-epoxyoctadec-9-enoyl) groups into triacylglycerol, whereas that from the hawk's beard incorporates both ricinoleoyl (12-hydroxyoctadec-9-enoyl) and vernoloyl groups. The enzyme from the yeast *Saccharomyces cerevisiae* specifically transfers acyl groups from the sn-2 position of the phospholipid to diacylglycerol, thus forming an sn-1-lysophospholipid. It has also been shown that PDAT activity is present in vegetative tissues of *Arabidopsis thaliana* (Banas et al., *Biochem. Soc. Trans.* 28:703-703 (2000)). Furthermore, the substrate specificity of PDAT varies between species and depends on the head group of the acyl donor, the acyl group transferred and the acyl chains of the acyl acceptor (1,2-diacylglycerol).

SUMMARY OF INVENTION

The present invention concerns isolated polynucleotides comprising a nucleotide sequence encoding a polypeptide having phospholipid:diacylglycerol acyltransferase activity, wherein the amino acid sequence of the polypeptide and the amino acid sequence of SEQ ID NO:2, 4, 6, 8, 10, 12, 14, 16, 18, 20, 22, 24, 26, 28, 32, 34 or 36 have at least 80%, 85%, 90% or 95% sequence identity, based on the Clustal V method of alignment. The present invention also relates to isolated polynucleotides comprising the complement of the nucleotide sequence. More specifically, the present invention includes isolated polynucleotides encoding the polypeptide sequence of SEQ ID NO:2, 4, 6, 8, 10, 12, 14, 16, 18, 20, 22, 24, 26, 28, 32, 34 or 36 or nucleotide sequences comprising the nucleotide sequence of SEQ ID NO:1, 3, 5, 7, 9, 11, 13, 15, 17, 19, 21, 23, 25, 27, 31, 33 or 35.

In a first embodiment, the present invention includes an isolated polynucleotide comprising: (a) a nucleotide sequence encoding a polypeptide having phospholipid:diacylglycerol acyltransferase activity, wherein the polypeptide has an amino acid sequence of at least 80%, 85%, 90%, or 95% sequence identity, based on the Clustal V method of alignment, when compared to one of SEQ ID NO:2, 4, 6, 8, 10, 12, 14, 16, 18, 20, 22, 24, 26, 28, 32, 34 or 36, or (b) a complement of the nucleotide sequence, wherein the complement and the nucleotide sequence consist of the same number of nucleotides and are 100% complementary. The polypeptide preferably comprises the amino acid sequence of SEQ ID NO:2, 4, 6, 8, 10, 12, 14, 16, 18, 20, 22, 24, 26, 28, 32, 34 or 36. The nucleotide sequence preferably comprises the nucleotide sequence of SEQ ID NO:1, 3, 5, 7, 9, 11, 13, 15, 17, 19, 21, 23, 25, 27, 31, 33 or 35.

In a second embodiment, the present invention includes a recombinant DNA construct comprising any of the isolated polynucleotides of the present invention operably linked to at least one regulatory sequence, and a cell, a plant, and a seed comprising the recombinant DNA construct.

In a third embodiment, the present invention includes a vector comprising any of the isolated polynucleotides of the present invention.

In a fourth embodiment, the present invention includes a method for transforming a cell comprising transforming a cell with any of the isolated polynucleotides of the present invention. The cell transformed by this method is also included. Advantageously, the cell is eukaryotic, e.g., a yeast or plant cell, or prokaryotic, e.g., a bacterium.

In a fifth embodiment, the present invention includes a method for producing a transgenic plant comprising transforming a plant cell with any of the isolated polynucleotides of the present invention and regenerating a plant from the transformed plant cell, a transgenic plant produced by this method, and seed obtained from this transgenic plant.

In a sixth embodiment, the present invention includes an isolated polypeptide having phospholipid:diacylglycerol acyltransferase activity, wherein the polypeptide has an amino acid sequence of at least 80%, 85%, 90%, or 95% identity, based on the Clustal V method of alignment, when compared to one of SEQ ID NO:2, 4, 6, 8, 10, 12, 14, 16, 18, 20, 22, 24, 26, 28, 32, 34 or 36. The polypeptide preferably comprises one of SEQ ID NO:2, 4, 6, 8, 10, 12, 14, 16, 18, 20, 22, 24, 26, 28, 32, 34 or 36.

In a seventh embodiment, the present invention includes a method for isolating a polypeptide having phospholipid:diacylglycerol acyltransferase activity comprising isolating the polypeptide from a cell or culture medium of the cell, wherein the cell comprises a recombinant DNA construct comprising a polynucleotide of the invention operably linked to at least one regulatory sequence.

In an eighth embodiment, this invention includes a method for selecting a transformed cell comprising: (a) transforming a host cell with the recombinant DNA construct or an expression cassette of the present invention; and (b) growing the transformed host cell, preferably a plant cell, under conditions that allow expression of the phospholipid:

diacylglycerol acyltransferase polynucleotide in an amount sufficient to complement a null mutant in order to provide a positive selection means.

In a ninth embodiment, this invention includes a method of altering the level of expression of a phospholipid:diacylglycerol acyltransferase protein in a host cell comprising: (a) transforming a host cell with a recombinant DNA construct of the present invention; and (b) growing the transformed host cell under conditions that are suitable for expression of the recombinant DNA construct wherein expression of the recombinant DNA construct results in production of altered levels of the phospholipid:diacylglycerol acyltransferase protein in the transformed host cell.

BRIEF DESCRIPTION OF THE DRAWINGS AND SEQUENCE LISTING

FIGS. 1A, 1B, 1C, 1D, 1E and 1F show a comparison of the amino acid sequences of the phospholipid:diacylglycerol acyltransferase (PDAT) 2 encoded by the following: (a) nucleotide sequence derived from guar clone Ids3c.pk001.j8:fis (SEQ ID NO:16), (b) nucleotide sequence derived from guayule clone epb3c.pk008.j11:fis (SEQ ID NO:18), (c) nucleotide sequence of a contig assembled from corn clone cds2f.pk002.k4:fis (SEQ ID NO:20), (d) nucleotide sequence derived from rice clone rlr6.pk00092.c4:fis (SEQ ID NO:22), (e) nucleotide sequence derived from soybean clone sdp2c.pk034.e7:fis (SEQ ID NO:24), (f) nucleotide sequence derived from sunflower clone hlp1c.pk004.11:fis (SEQ ID NO:26), (g) nucleotide sequence of a contig assembled from nucleotide sequences derived from wheat clones wip1c.pk005.b24:fis and wlm96.pk006.f11 (SEQ ID NO:28), (h) nucleotide sequence derived from soybean clone sgs4c.pk006.b20:fis (SEQ ID NO:36) and (i) nucleotide sequence from *Arabidopsis thaliana* (NCBI General Identification (GI) No. 15240676; SEQ ID NO:30). Dashes are used by the program to maximize alignment of the sequences.

FIGS. 2A, 2B, 2C, 2D and 2E show a comparison of the amino acid sequences of the phospholipid:diacylglycerol acyltransferase (PDAT) 1 encoded by the following: (a) nucleotide sequence derived from balsam pear clone fds.pk0003.b4:fis (SEQ ID NO:2), (b) nucleotide sequence derived from pot marigold clone ecs1c.pk009.j18:fis (SEQ ID NO:4), (c) nucleotide sequence derived from eucalyptus clone eef1c.pk006.c14:fis (SEQ ID NO:6), (d) nucleotide sequence derived from grape clone vmb1na.pk016.c2:fis (SEQ ID NO:8), (e) nucleotide sequence derived from rice clone rsr9n.pk002.f3:fis (SEQ ID NO:10), (f) nucleotide sequence derived from vernonia clone vs1n.pk016.n3:fis (SEQ ID NO:12), (g) nucleotide sequence derived from wheat clone wpa1c.pk009.g15 (SEQ ID NO:14, (h) nucleotide sequence derived from guar clone Ids3c.pk008.f17:fis (SEQ ID NO:32), (i) nucleotide sequence derived from wheat clone wpa1c.pk009.g15:fis (SEQ ID NO:34) and (j) nucleotide sequence from *Arabidopsis thaliana* (NCBI General Identification (GI) No. 7452457; SEQ ID NO:29). Dashes are used by the program to maximize alignment of the sequences.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821-1.825.

TABLE 1

Phospholipid:diacylglycerol Acyltransferases

| Protein | Clone Designation | SEQ ID NO: (Nucleotide) | (Amino Acid) |
| --- | --- | --- | --- |
| Balsam Pear Polypeptide Similar to *Arabidopsis thaliana* PDAT 1 | fds.pk0003.b4:fis | 1 | 2 |
| *Calendula* Polypeptide Similar to *Arabidopsis thaliana* PDAT 1 | Ecs1c.pk009.j18:fis | 3 | 4 |
| *Eucalyptus* Polypeptide Similar to *Arabidopsis thaliana* PDAT 1 | Eef1c.pk006.c14:fis | 5 | 6 |
| Grape Polypeptide Similar to *Arabidopsis thaliana* PDAT 1 | Vmb1na.pk016.c2:fis | 7 | 8 |
| Rice Polypeptide Similar to *Arabidopsis thaliana* PDAT 1 | rsr9n.pk002.f3:fis | 9 | 10 |
| *Vernonia* Polypeptide Similar to *Arabidopsis thaliana* PDAT 1 | vs1n.pk016.n3:fis | 11 | 12 |
| Wheat Polypeptide Similar to *Arabidopsis thaliana* PDAT 1 | Wpa1c.pk009.g15 | 13 | 14 |
| Guar Polypeptide Similar to *Arabidopsis thaliana* PDAT 1 | Lds3c.pk008.f17:fis | 31 | 32 |
| Wheat Polypeptide Similar to *Arabidopsis thaliana* PDAT 1 | Wpa1c.pk009.g15:fis | 33 | 34 |
| Guar Polypeptide Similar to *Arabidopsis thaliana* PDAT 2 | Lds3c.pk001.j8:fis | 15 | 16 |
| Guayule Polypeptide Similar to *Arabidopsis thaliana* PDAT 2 | Epb3c.pk008.j11:fis | 17 | 18 |
| Corn Polypeptide Similar to *Arabidopsis thaliana* PDAT 2 | Contig of: Cds2f.pk002.k4:fis | 19 | 20 |
| Rice Polypeptide Similar to *Arabidopsis thaliana* PDAT 2 | rlr6.pk0092.c4:fis | 21 | 22 |

TABLE 1-continued

Phospholipid:diacylglycerol Acyltransferases

| Protein | Clone Designation | SEQ ID NO: (Nucleotide) | SEQ ID NO: (Amino Acid) |
|---|---|---|---|
| Soybean Polypeptide Similar to *Arabidopsis thaliana* PDAT 2 | Sdp2c.pk034.e7:fis | 23 | 24 |
| Sunflower Polypeptide Similar to *Arabidopsis thaliana* PDAT 2 | Hlp1c.pk004.i1:fis | 25 | 26 |
| Wheat Polypeptide Similar to *Arabidopsis thaliana* PDAT 2 | Contig of: Wip1c.pk005.b24:fis Wlm96.pk0006.f11 | 27 | 28 |
| Soybean Polypeptide Similar to *Arabidopsis thaliana* PDAT 2 | Sgs4c.pk006.b20:fis | 35 | 36 |

SEQ ID NO:29 is the amino acid sequence of *Arabidopsis thaliana* (NCBI General Identification (GI) No. 7452457). NCBI General Identifier No. 7452457 is 100% identical to NCBI General Identifier No. 15235214 and NCBI Accession No. CAA19703. *Arabidopsis thaliana* CM19703 can be found in FIG. 5 of Dahlqvist et al., *Proc. Natl. Acad. Sci. USA* 97(12):6487-6492 (2000).

SEQ ID NO:30 is the amino acid sequence of *Arabidopsis thaliana* (NCBI General Identification (GI) No. 15240676). NCBI General Identifier No. 15240676 is 100% identical to NCBI General Identifier No. 9758029 and NCBI Accession No. AB006704. *Arabidopsis thaliana* AB006704 can be found in FIG. 5 of Dahlqvist et al., *Proc. Natl. Acad. Sci. USA* 97(12):6487-6492 (2000).

The Sequence Listing contains the one letter code for nucleotide sequence characters and the three letter codes for amino acids as defined in conformity with the IUPAC-IUBMB standards described in Nucleic Acids Res. 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. §1.822.

DETAILED DESCRIPTION OF THE INVENTION

The disclosure of each reference set forth herein is incorporated herein by reference in its entirety.

In the context of this disclosure, a number of terms shall be utilized. The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least 30 contiguous nucleotides, preferably at least 40 contiguous nucleotides, most preferably at least 60 contiguous nucleotides derived from SEQ ID NO:1, 3, 5, 7, 9, 11, 13, 15, 17, 19, 21, 23, 25, 27, 31, 33 or 35, or the complement of such sequences.

The term "isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques. A "recombinant DNA construct" comprises any of the isolated polynucleotides of the present invention operably linked to at least one regulatory sequence.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides, preferably at least 40 contiguous nucleotides, most preferably at least 60 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least 30 (preferably at least 40, most preferably at least 60) contiguous nucleotides derived from a nucleotide sequence selected from the group consisting of SEQ ID NO:1, 3, 5, 7, 9, 11, 13, 15, 17, 19, 21, 23, 25, 27, 31, 33 or 35, and the complement of such nucleotide sequences may be used to affect the expression and/or function of a phospholipid:diacylglycerol acyltransferases (PDAT 1 or PDAT 2) in a host cell. A method of using an isolated polynucleotide to affect the level of expression of a polypeptide in a host cell (eukaryotic, such as plant or yeast, prokaryotic such as bacterial) may comprise the steps of: constructing an isolated polynucleotide of the present invention or an isolated recombinant DNA construct of the present invention; introducing the isolated polynucleotide or isolated recombinant DNA construct into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 75% identical, preferably at least about 80% identical to the amino acid sequences reported herein. Preferred nucleic acid fragments encode amino acid sequences that are at least about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above identities but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal V method of alignment (Higgins and Sharp (1989) *CABIOS*. 5:151-153) with the default parameters (GAP PENALTY=10, GAP LENGTH PENALTY=10). Default parameters for pairwise alignments using the Clustal V method of alignment were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403410; see also the explanation of the BLAST alogarithm on the world wide web site for the National Center for Biotechnology Information at the National Library of Medicine of the National Institutes of Health). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign-gene" refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1-82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225-236).

"3'non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double stranded form using, for example, the Klenow fragment of DNA polymerase 1. "Sense-RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refers to the production of gene product(s) in transgenic organisms in amounts or proportions that differ from that of normal or non-transformed organisms.

"Mature protein" or the term "mature" when used in describing a protein refers to a post-translationally processed polypeptide; i.e., one from which any pre- or propeptides present in the primary translation product have been removed. "Precursor protein" or the term "precursor" when used in describing a protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627-1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature* (London) 327:70-73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

"PCR" or "polymerase chain reaction" is well known by those skilled in the art as a technique used for the amplification of specific DNA segments (U.S. Pat. Nos. 4,683,195 and 4,800,159).

The present invention includes an isolated polynucleotide comprising a nucleotide sequence encoding a phospholipid:diacylglycerol acyltransferase polypeptide having at least 80% identity, based on the Clustal V method of alignment, when compared to a polypeptide selected from the group consisting of SEQ ID NO:2, 4, 6, 8, 10, 12, 14, 16, 18, 20, 22, 24, 26, 28, 32, 34 or 36.

This invention also includes the isolated complement of such polynucleotides, wherein the complement and the polynucleotide consist of the same number of nucleotides, and the nucleotide sequences of the complement and the polynucleotide have 100% complementarity.

Nucleic acid fragments encoding at least a portion of several phospholipid:diacylglycerol acyltransferases have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other phospholipid:diacylglycerol acyltransferases (PDAT 1 or PDAT 2), either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, an entire sequence can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998-9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673-5677; Loh et al. (1989) *Science* 243:217-220). Products generated by the 3' and 5' RACE procedures can be combined to generate full-length cDNAs (Frohman and Martin (1989) *Techniques* 1:165). Consequently, a polynucleotide comprising a nucleotide sequence of at least 30 (preferably at least 40, most preferably at least 60) contiguous nucleotides derived from a nucleotide sequence selected from the group consisting of SEQ ID NO:1, 3, 5, 7, 9, 11, 13, 15, 17, 19, 21, 23, 25, 27, 31, 33 or 35 and the complement of such nucleotide sequences may be used in such methods to obtain a nucleic acid fragment encoding a substantial portion of an amino acid sequence of a polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1-34; Maniatis).

In another embodiment, this invention includes viruses and host cells comprising either the recombinant DNA constructs of the invention as described herein or an isolated polynucleotide or recombinant DNA construct of the invention as described herein. Examples of host cells which can be used to practice the invention include, but are not limited to, yeast, bacteria, and plants.

The nucleic acid fragments of the instant invention may be used to create transgenic plants in which the disclosed polypeptides are present at higher or lower levels than normal or in cell types or developmental stages in which they are not normally found. This would have the effect of altering the level of oil (triacylglycerol) in those cells. The genes of the instant invention may also be used in plant cells to alter the type of oil (triacylglycerol) produced in the cells. PDAT may be a critical enzyme in the metabolism of unusual fatty acids. More specifically, PDAT may be used to accumulate high amounts of uncommon fatty acids from renewable plant resources which have industrial potential. Accordingly, the availability of nucleic acid sequences encoding all or a portion of the enzyme phospholipid:diacylglycerol acyltransferase (PDAT) would facilitate studies to better understand triacylglycerol biosynthesis in plants and provide genetic tools to alter triacylglycerol metabolism.

Overexpression of the proteins of the instant invention may be accomplished by first constructing a recombinant DNA construct in which the coding region is operably linked to a promoter capable of directing expression of a gene in the desired tissues at the desired stage of development. The recombinant DNA construct may comprise promoter sequences and translation leader sequences derived from the same genes. 3' Non-coding sequences encoding transcription termination signals may also be provided. The instant recombinant DNA construct may also comprise one or more introns in order to facilitate gene expression.

Plasmid vectors comprising the instant isolated polynucleotide (or recombinant DNA construct) may be constructed. The choice of plasmid vector is dependent upon the method that will be used to transform host plants. The skilled artisan is well aware of the genetic elements that must be present on the plasmid vector in order to successfully transform, select and propagate host cells containing the recombinant DNA construct. The skilled artisan will also recognize that different independent transformation events will result in different levels and patterns of expression (Jones et al. (1985) *EMBO J.* 4:2411-2418; De Almeida et al. (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the recombinant DNA construct described above may be further supplemented by directing the coding sequence to encode the instant polypeptides with appropriate intracellular targeting sequences such as transit sequences (Keegstra (1989) *Cell* 56:247-253), signal sequences or sequences encoding endoplasmic reticulum localization (Chrispeels (1991) *Ann. Rev. Plant Phys. Plant Mol. Biol.* 42:21-53), or nuclear localization signals (Raikhel (1992) *Plant Phys.* 100:1627-1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a recombinant DNA construct designed for co-suppression of the instant polypeptide can be constructed by linking a gene or gene fragment encoding that polypeptide to plant promoter sequences. Alternatively, a recombinant DNA construct designed to express antisense RNA for all or part of the instant nucleic acid fragment can be constructed by linking the gene or gene fragment in reverse orientation to plant promoter sequences. Either the co-suppression or antisense recombinant DNA constructs could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation.of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different recombinant DNA constructs utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another embodiment, the present invention includes a phospholipid:diacylglycerol acyltransferase (PDAT) polypeptide having an amino acid sequence that is at least 80% identical, based on the Clustal V method of alignment, to a polypeptide selected from the group consisting of SEQ ID NO:2, 4, 6, 8, 10, 12, 14, 16, 18, 20, 22, 24, 26, 28, 32, 34 or 36.

The instant polypeptides (or portions thereof) may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a recombinant DNA construct for production of the instant polypeptides. This recombinant DNA construct could then be introduced into appropriate microorganisms via transformation to provide high level expression of the encoded phospholipid:diacylglycerol acyltransferase. An example of a vector for high level expression of the instant polypeptides in a bacterial host is provided (Example 7).

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174-181) in orderto construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314-331).

The production and use of plant gene-derived probes for use in genetic mapping is described in Bernatzky and Tanksley (1986) *Plant Mol. Biol. Reporter* 4:3741. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319-346, and references cited therein).

Nucleic acid probes derived from the instant nucleic acid sequences may be used in direct fluorescence in situ hybridization (FISH) mapping (Trask (1991) *Trends Genet.* 7:149-154). Although current methods of FISH mapping favor use of large clones (several to several hundred KB; see Laan et al. (1995) *Genome Res.* 5:13-20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95-96), polymorphism of PCR-amplified fragments (CAPS; Sheffield et al. (1993) *Genomics* 16:325-332), allele-specific ligation (Landegren et al. (1988) *Science* 241:1077-1080), nucleotide extension reactions (Sokolov (1990) *Nucleic Acid Res.* 18:3671), Radiation Hybrid Mapping (Walter et al. (1997) *Nat. Genet.* 7:22-28) and Happy Mapping (Dear and Cook (1989) *Nucleic Acid Res.* 17:6795-6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402-9406; Koes et al. (1995) *Proc. Natl. Acad. Sci USA* 92:8149-8153; Bensen et al. (1995) *Plant Cell* 7:75-84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further illustrated in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

Composition of cDNA Libraries; Isolation and Sequencing of cDNA Clones cDNA libraries representing mRNAs from various balsam pear (*Momordica charantia*), pot marigold (*Calendula officinalis*), eucalyptus (*Eucalyptus grandis*), grape (*Vitis* sp.), rice (*Oryza sativa*), vernonia (*Vernonia mespilifolia*), wheat-common (*Triticum aestivum*), guar (*Cyamopsos tetragonoloba*), guayule (*Parthenium argentatum* Grey), maize (*Zea mays*), rice (*Oryza sativa*), soybean (*Glycine max*) and sunflower (*Helianthus* sp.) tissues were prepared. The characteristics of the libraries are described below.

TABLE 2 cDNA Libraries from Balsam Pear, Pot marigold, Eucalyptus, Grape, Rice,
Vernonia, Wheat, Guar, Guayule, Maize, Rice, Soybean and Sunflower

| Library | Tissue | Clone |
|---------|--------|-------|
| fds | *Momordica charantia* developing seed | fds.pk0003.b4:fis |
| ecs1c | Pot marigold (*Calendula officinalis*) developing seeds | ecs1c.pk009.j18:fis |
| eef1c | *Eucalyptus tereticornis* flower buds from adult tree | eef1c.pk006.c14:fis |
| vmb1na | Grape (*Vitis* sp.) midstage berries normalized | vmb1na.pk016.c2:fis |
| rsr9n | Rice (*Oryza sative* L.) leaf 15 days after germination harvested 2-72 hours following infection with *Magnaporta grisea** | rsr9n.pk002.f3:fis |
| vs1n | *Vernonia* Seed* | vs1n.pk016.n3:fis |
| wpa1c | Wheat (*Triticum aestivum*) pre-meiotic anthers JIC | wpa1c.pk009.g15 wpa1c.pk009.g15:fis |
| lds3c | Guar (*Cyamopsos tetragonoloba*) seeds harvested 32 days after flowering | lds3c.pk001.j8:fis lds3c.pk008.f17:fis |
| epb3c | Guayule (*Parthenium argentatum*, 11591) stem bark harvested at Dec. 28, 1993 - high activity for rubber biosynthesis | epb3c.pk008.j11:fis |
| cds2f | Corn (*Zea mays*, B73) 11 day old seedling full length library using trehalose | cds2f.pk002.k4:fis |
| rlr6 | Rice leaf 15 days after germination, 6 hours after infection of strain with *Magaporthe grisea*; Resistant | rlr6.pk0092.c4:fis |
| sdp2c | Soybean (*Glycine max* L.) developing pods (6-7 mm) | sdp2c.pk034.e7:fis |
| sgs4c | Soybean (*Glycine max* L.) seeds 2 days after germination | sgs4c.pk006.b20:fis |

TABLE 2-continued cDNA Libraries from Balsam Pear, Pot marigold, Eucalyptus, Grape, Rice,
Vernonia, Wheat, Guar, Guayule, Maize, Rice, Soybean and Sunflower

| Library | Tissue | Clone |
|---|---|---|
| hlp1c | Sunflower (*Helianthus* sp.) leaf infected with phomopsis | hlp1c.pk004.i1:fis |
| wip1c | Wheat (*Triticum aestivum*, Hi Line) immature pistils | wip1c.pk005.b24:fis |
| wlm96 | Wheat (*Wheat aestivum*) seedlings 96 hours after inoculation with *Erysiphe graminis* f. sp *tritici* | wlm96.pk0006.f11 |

*These libraries were normalized essentially as described in U.S. Pat. No. 5,482,845, incorporated herein by reference.

CDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651-1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke (1994) *Nucleic Acids Res.* 22:3765-3772). The in vitro transposition system places unique binding sites randomly throughout a population of large DNA molecules. The transposed DNA is then used to transform DH10B electro-competent cells (Gibco BRL/Life Technologies, Rockville, Md.) via electroporation. The transposable element contains an additional selectable marker (named DHFR; Fling and Richards (1983) *Nucleic Acids Res.* 11:5147-5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism dye-terminator ReadyReaction mix) outward from the transposition event site, utilizing unique primers specific to the binding sites within the transposon.

Sequence data is collected (ABI Prism Collections) and assembled using Phred/Phrap (P. Green, University of Washington, Seattle). Phrep/Phrap is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (D. Gordon, University of Washington, Seattle).

In some of the clones the cDNA fragment corresponds to a portion of the 3'-terminus of the gene and does not cover the entire open reading frame. In order to obtain the upstream information one of two different protocols are used. The first of these methods results in the production of a fragment of DNA containing a portion of the desired gene sequence while the second method results in the production of a fragment containing the entire open reading frame. Both of these methods use two rounds of PCR amplification to obtain fragments from one or more libraries. The libraries some times are chosen based on previous knowledge that the specific gene should be found in a certain tissue and some times are randomly-chosen. Reactions to obtain the same gene may be performed on several libraries in parallel or on a pool of libraries. Library pools are normally prepared using from 3 to 5 different libraries and normalized to a uniform dilution. In the first round of amplification both methods use a vector-specific (forward) primer corresponding to a portion of the vector located at the 5'-terminus of the clone coupled with a gene-specific (reverse) primer. The first method uses a sequence that is complementary to a portion of the already known gene sequence while the second method uses a gene-specific primer complementary to a portion of the 3'-untranslated region (also referred to as UTR). In the second round of amplification a nested set of primers is used for both methods. The resulting DNA fragment is ligated into a pBluescript vector using a commercial kit and following the manufacturer's protocol. This kit is selected from many available from several vendors including Invitrogen (Carlsbad, Calif.), Promega Biotech (Madison, Wis.), and Gibco-BRL (Gaithersburg, Md.). The plasmid DNA is isolated by alkaline lysis method and submitted for sequencing and assembly using Phred/Phrap, as above.

Example 2

Identification of cDNA Clones cDNA clones encoding phospholipid:diacylglycerol acyltransferases were identified by conducting BLAST (Basic Local Alignment Search Tool; Altschul et al. (1993) *J. Mol. Biol.* 215:403410; see also the explanation of the BLAST alogarithm on the world wide web site for the National Center for Biotechnology Information at the National Library of Medicine of the National Institutes of Health) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example. 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266-272) provided by the NCBI. For convenience, the P-value (probability) of observing a match of a cDNA sequence to a sequence contained in the searched databases merely by chance as calculated by BLAST are reported herein as "plog" values, which represent the negative of the logarithm of the reported P-value. Accordingly, the greater the pLog value, the greater the likelihood that the cDNA sequence and the BLAST "hit" represent homologous proteins.

ESTs submitted for analysis are compared to the GenBank database as described above. ESTs that contain sequences more 5- or 3-prime can be found by using the BLASTn algorithm (Altschul et al (1997) *Nucleic Acids Res.* 25:3389-3402.) against the DuPont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described in Example 1. Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 3

Characterization of cDNA Clones Encoding Proteins Similar to *Arabidopsis thaliana* PDAT 2

The BLASTX search using the EST sequences from clones listed in Table 3 revealed similarity of the polypeptides encoded by the cDNAs to phospholipid:diacylglycerol acyltransferase (PDAT) 2 from *Arabidopsis thaliana* (NCBI General Identifier No. 15240676; SEQ ID NO:30) (NCBI General Identifier No. 15240676 is 100% identical to NCBI General Identifier No. 9758029.) Shown in Table 3 are the BLAST results for the sequences of the entire cDNA inserts comprising the indicated cDNA clones ("FIS"), the sequences of contigs assembled from two or more ESTs ("Contig"), sequences of contigs assembled from an FIS and one or more ESTs ("Contig*") or sequences encoding an entire protein derived from an FIS, a contig, or an FIS and PCR ("CGS"):

TABLE 3

BLAST Results for Sequences Encoding Polypeptides Homologous to Phospholipid:diacylglycerol Acyltransferase (PDAT) 2

| Clone | Status | BLAST pLog Score NCBI General Identifier No. 15240676 |
|---|---|---|
| lds3c.pk001.j8:fis | FIS | 165.00 |
| epb3c.pk008.j11:fis | CGS | 180.00 |
| Contig of: cds2f.pk002.k4:fis | CGS | 180.00 |
| rlr6.pk0092.c4:fis | CGS | 180.00 |
| sdp2c.pk034.e7:fis | CGS | 180.00 |
| hlp1c.pk004.i1:fis | CGS | 180.00 |
| Contig of: wip1c.pk005.b24:fis wlm96.pk0006.f11 | Contig | 180.00 |
| sgs4c.pk006.b20:fis | CGS | 180.00 |

The nucleotide sequence of the entire cDNA insert in clone Ids3c.pk001.j8:fis is shown in SEQ ID NO:15. The amino acid sequence deduced from nucleotides 10 through 1176 of SEQ ID NO:15 is shown in SEQ ID NO:16 (stop codon encoded by nucleotides 1177-1179). The nucleotide sequence of the entire cDNA insert in clone epb3c.pk008.j11:fis is shown in SEQ ID NO:17. The amino acid sequence deduced from nucleotides 39 through 2042 of SEQ ID NO:17 is shown in SEQ ID NO:18 (start codon encoded by nucleotides 3941 and stop codon encoded by nucleotides 2043-2045). The nucleotide sequence of the contig of clone cds2f.pk002.k4:fis is shown in SEQ ID NO:19. The amino acid sequence deduced from nucleotides 202 through 2229 of SEQ ID NO:19 is shown in SEQ ID NO:20 (start codon encoded by nucleotides 202-204 and stop codon encoded by nucleotides 2230-2232). The nucleotide sequence of the entire cDNA insert in clone rlr6.pk0092.c4:fis is shown in SEQ ID NO:21. The amino acid sequence deduced from nucleotides 160 through 2232 of SEQ ID NO:21 is shown in SEQ ID NO:22 (start codon encoded by nucleotides 160-162 and stop codon encoded by nucleotides 2233-2235). The nucleotide sequence of the entire cDNA insert in clone sdp2c.pk034.e7:fis is shown in SEQ ID NO:23. The amino acid sequence deduced from nucleotides 330 through 2357 of SEQ ID NO:23 is shown in SEQ ID NO:24 (start codon encoded by nucleotides 330-332 and stop codon encoded by nucleotides 2358-2360). The nucleotide sequence of the entire cDNA insert in clone hlp1c.pk004.11:fis is shown in SEQ ID NO:25. The amino acid sequence deduced from nucleotides 104 through 2113 of SEQ ID NO:25 is shown in SEQ ID NO:26 (start codon encoded by nucleotides 104-106 and stop codon encoded by nucleotides 2114-2116). The nucleotide sequence of the contig of clones wip1c.pk005.b24:fis and wlm96.pk0006.f11 is shown in SEQ ID NO:27. The amino acid sequence of SEQ ID NO:27 is shown in SEQ ID NO:28 (stop codon encoded by nucleotides 1801-1803). The nucleotide sequence of the entire cDNA insert in clone sgs4c.pk006.b20:fis is shown in SEQ ID NO:35. The amino acid sequence deduced from nucleotides 267 through 2294 of SEQ ID NO:35 is shown in SEQ ID NO:36 (start codon encoded by nucleotides 267-269 and stop codon encoded by nucleotides 2295-2297).

FIGS. 1A, 1B, 1C, 1D, 1E and 1F present an alignment of the amino acid sequences set forth in SEQ ID NOs:16, 18, 20, 22, 24, 26, 28, 36 and the sequence from *Arabidopsis thaliana* sequence (NCBI General Identification (GI) No. 15240676; SEQ ID NO:30). The data in Table 4 represents a calculation of the percent identity of the amino acid sequences set forth in SEQ ID NOs:16, 18, 20, 22, 24, 26, 28, 36 and the sequence from *Arabidopsis thaliana* sequence (NCBI General Identification (GI) No. 15240676; SEQ ID NO:30).

TABLE 4

Percent Identity of Amino Acid Sequences Deduced From the Nucleotide Sequences of cDNA Clones Encoding Polypeptides Homologous to Phospholipid:diacylglycerol Acyltransferase (PDAT) 2

| Clone | SEQ ID NO. | Percent Identity to NCBI General Identifier No. 15240676 (SEQ ID NO:30) |
|---|---|---|
| lds3c.pk001.j8:fis | 16 | 71.2 |
| epb3c.pk008.j11:fis | 18 | 74.0 |
| Contig of: cds2f.pk002.k4:fis | 20 | 73.3 |
| rlr6.pk0092.c4:fis | 22 | 73.2 |
| sdp2c.pk034.e7:fis | 24 | 71.8 |
| hlp1c.pk004.i1:fis | 26 | 74.6 |
| Contig of: wip1c.pk005.b24:fis wlm96.pk0006.f11 | 28 | 74.2 |
| sgs4c.pk006.b20:fis | 36 | 72.3 |

Sequence alignments and percent identity calculations were performed using the Megalign program of the LASERGENE bioinformatics computing suite (DNASTAR Inc., Madison, Wis.). Multiple alignment of the sequences was performed using the Clustal V method of alignment (Higgins and Sharp (1989) CABIOS. 5:151-153) with the default parameters (GAP PENALTY=10, GAP LENGTH PENALTY=10). Default parameters for pairwise alignments using the Clustal V method of alignment were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a phospholipid:diacylglycerol acyltransferase. These sequences are believed to represent the first dicot species sequences encoding phospholipid:diacylglycerol acyltransferases known to Applicant.

Example 4

Characterization of cDNA Clones Encoding Proteins Similar to *Arabidopsis thaliana* PDAT 1

The BLASTX search using the EST sequences from clones listed in Table 5 revealed similarity of the polypeptides encoded by the cDNAs to phospholipid:diacylglycerol acyltransferase (PDAT) 1 from *Arabidopsis thaliana* (NCBI General Identifier No. 7452457; SEQ ID NO:29). (NCBI General Identifier No. 7452457 is 100% identical to NCBI General Identifier No. 15235214.) Shown in Table 5 are the BLAST results for the sequences of the entire cDNA inserts comprising the indicated cDNA clones ("FIS"), the sequences of contigs assembled from two or more ESTs ("Contig"), sequences of contigs assembled from an FIS and one or more ESTs ("Contig*") or sequences encoding an entire protein derived from an FIS, a contig, or an FIS and PCR ("CGS"):

TABLE 5

BLAST Results for Sequences Encoding Polypeptides Homologous to Phospholipid:diacylglycerol Acyltransferase (PDAT) 1

| Clone | Status | BLAST pLog Score NCBI General Identifier No. 7452457 (SEQ ID NO:29) |
|---|---|---|
| fds.pk0003.b4:fis | CGS | 90.30 |
| ecs1c.pk009.j18:fis | CGS | 90.70 |
| eef1c.pk006.c14:fis | CGS | 146.00 |
| vmb1na.pk016.c2:fis | CGS | 99.00 |
| rsr9n.pk002.f3:fis | FIS | 45.52 |
| vs1n.pk016.n3:fis | FIS | 47.70 |
| wpa1c.pk009.g15 | EST | 42.70 |
| lds3c.pk008.f17:fis | CGS | 89.05 |
| wpa1c.pk009.g15:fis | CGS | 84.52 |

The nucleotide sequence of the entire cDNA insert in clone fds.pk0003.b4:fis is shown in SEQ ID NO:1. The amino acid sequence deduced from nucleotides 72 through 1682 of SEQ ID NO:1 is shown in SEQ ID NO:2 (start codon encoded by nucleotides 72-74 and stop codon encoded by nucleotides 1683-1685). The nucleotide sequence of the entire cDNA insert in clone ecs1c.pk009.j18:fis is shown in SEQ ID NO:3. The amino acid sequence deduced from nucleotides 29 through 1618 of SEQ ID NO:3 is shown in SEQ ID NO:4 (start codon encoded by nucleotides 29-31 and stop codon encoded by nucleotides 1619-1621). The nucleotide sequence of the entire cDNA insert in clone eef1c.pk006.c14:fis is shown in SEQ ID NO:5. The amino acid sequence deduced from nucleotides 216 through 1820 of SEQ ID NO:5 is shown in SEQ ID NO:6 (start codon encoded by nucleotides 216-218 and stop codon encoded by nucleotides 1821-1823). The nucleotide sequence of the entire cDNA insert in clone vmb1na.pk016.c2:fis is shown in SEQ ID NO:7. The amino acid sequence deduced from nucleotides 202 through 1800 of SEQ ID NO:7 is shown in SEQ ID NO:8 (start codon encoded by nucleotides 202-204 and stop codon encoded by nucleotides 1801-1803). The nucleotide sequence of the entire cDNA insert in clone rsr9n.pk002.f3:fis is shown in SEQ ID NO:9. The amino acid sequence deduced from nucleotides 2 through 1213 of SEQ ID NO:9 is shown in SEQ ID NO:10 (stop codon encoded by nucleotides 1214-1216). The nucleotide sequence of the contig of clone vs1n.pk016.n3:fis is shown in SEQ ID NO:11. The amino acid sequence deduced from nucleotides 2 through 1300 of SEQ ID NO:11 is shown in SEQ ID NO:12 (stop codon encoded by nucleotides 1301-1303). The nucleotide sequence of a portion of the cDNA insert in clone wpa1c.pk009.g15 is shown in SEQ ID NO:13. The amino acid sequence deduced from nucleotides 238 through 634 of SEQ ID NO:13 is shown in SEQ ID NO:14 (start codon encoded by nucleotides 238-240). The nucleotide sequence of the entire cDNA insert in clone lds3c.pk008.f17:fis is shown in SEQ ID NO:31. The amino acid sequence deduced from nucleotides 125 through 1741 of SEQ ID NO:31 is shown in SEQ ID NO:32 (start codon encoded by nucleotides 125-127 and stop codon encoded by nucleotides 1739-1741). The nucleotide sequence of the entire cDNA insert in clone wpa1c.pk009.g15:fis is shown in SEQ ID NO:33. The amino acid sequence deduced from nucleotides 238 through 1839 of SEQ ID NO:33 is shown in SEQ ID NO:34 (start codon encoded by nucleotides 238-240 and stop codon encoded by nucleotides 1840-1842).

FIGS. 2A, 2B, 2C, 2D and 2E present an alignment of the amino acid sequences set forth in SEQ ID NOs:2, 4, 6, 8, 10, 12, 14, 32, 34 and the sequence from *Arabidopsis thaliana* sequence (NCBI General Identification (GI) No. 7452457; SEQ ID NO:29). The data in Table 6 represents a calculation of the percent identity of the amino acid sequences set forth in SEQ ID NOs: 2, 4, 6, 8, 10, 12, 14, 32, 34 and the sequence from *Arabidopsis thaliana* sequence (NCBI General Identification (GI) No. 7452457; SEQ ID NO:29).

TABLE 6

Percent Identity of Amino Acid Sequences Deduced From the Nucleotide Sequences of cDNA Clones Encoding Polypeptides Homologous to Phospholipid:diacylglycerol Acyltransferase (PDAT) 1

| Clone | SEQ ID NO. | Percent Identity to NCBI General Identifier No. 7452457; SEQ ID NO:29 |
|---|---|---|
| fds.pk0003.b4:fis | 2 | 52.1 |
| ecs1c.pk009.j18:fis | 4 | 48.3 |
| eef1c.pk006.c14:fis | 6 | 56.2 |
| vmb1na.pk016.c2:fis | 8 | 54.4 |
| rsr9n.pk002.f3:fis | 10 | 39.1 |
| vs1n.pk016.n3:fis | 12 | 43.0 |
| wpa1c.pk009.g15 | 14 | 58.3 |
| lds3c.pk008.f17:fis | 32 | 52.5 |
| wpa1c.pk009.g15:fis | 34 | 47.7 |

Sequence alignments and percent identity calculations were performed using the Megalign program of the LASERGENE bioinformatics computing suite (DNASTAR Inc., Madison, Wis.). Multiple alignment of the sequences was performed using the Clustal V method of alignment (Higgins and Sharp (1989) CABIOS. 5:151-153) with the default parameters (GAP PENALTY=10, GAP LENGTH PENALTY=10). Default parameters for pairwise alignments using the Clustal V method of alignment were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a phospholipid:diacylglycerol acyltransferase.

Example 5

Expression of Recombinant DNA Constructs in Monocot Cells

A recombinant DNA construct comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a recombinant DNA construct encoding, in the 5' to 3' direction, the maize 27 kD zein promoter, a cDNA fragment encoding the instant polypeptides, and the 10 kD zein 3' region.

The recombinant DNA construct described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659-668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810-812) and the 3' region of the nopaline synthase gene from the T-DNA of the Ti plasmid of *Agrobacterium tumefaciens*.

The particle bombardment method (Klein et al. (1987) *Nature* 327:70-73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains bialophos (5 mg per liter) and lacks casein or proline. The tissue continues to grow slowly on this medium. After an additional 2 weeks the tissue can be transferred to fresh N6 medium containing bialophos. After 6 weeks, areas of about 1 cm in diameter of actively growing callus can be identified on some of the plates containing the bialophos-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833-839).

Example 6

Expression of Recombinant DNA Constructs in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228-9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites NcoI (which includes the ATG translation initiation codon), SmaI, KpnI and XbaI. The entire cassette is flanked by HindIII sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70-73, U.S. Pat. No. 4,945,050). A DuPont Biolisticm PDS1000/HE instrument (helium retrofit) can be used for these transformations.

A selectable marker gene which can be used to facilitate soybean transformation is a recombinant DNA construct composed of the 35S promoter from Cauliflower Mosaic Virus (Odell et al. (1985) *Nature* 313:810-812), the hygromycin phosphotransferase gene from plasmid pJR225 (from *E. coli*; Gritz et al. (1983) *Gene* 25:179-188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µL spermidine (0.1 M), and 50 µL $CaCl_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Expression of Recombinant DNA Constructs in Microbial Cells

The cDNAs encoding the instant polypeptides can be inserted into the T7 *E. coli* expression vector pBT430. This vector is a derivative of pET-3a (Rosenberg et al. (1987) *Gene* 56:125-135) which employs the bacteriophage T7 RNA polymerase/T7 promoter system. Plasmid pBT430 was constructed by first destroying the EcoRI and HindIII sites in pET-3a at their original positions. An oligonucleotide adaptor containing EcoRI and Hind III sites was inserted at the BamHI site of pET-3a. This created pET-3aM with additional unique cloning sites for insertion of genes into the expression vector. Then, the NdeI site at the position of translation initiation was converted to an NcoI site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% low melting agarose gel. Buffer and agarose contain 10 µg/ml ethidium bromide for visualization of the DNA fragment. The fragment can then be purified from the agarose gel by digestion with GELase™ (Epicentre Technologies, Madison, Wis.) according to the manufacturer's instructions, ethanol precipitated, dried and resuspended in 20 µL of water. Appropriate oligonucleotide adapters may be ligated to the fragment using T4 DNA ligase (New England Biolabs (NEB), Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113-130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25° C. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity. For example, assays for phospholipid:diacylglycerol acyltransferase (PDAT) are presented by Dahlqvist et al., *Proc. Natl. Acad. Sci. USA* 97(12):6487-6492 (2000).

What is claimed is:

1. An isolated polynucleotide comprising:
   (a) a nucleotide sequence encoding a polypeptide having phospholipid:diacylglycerol acyltransferase activity, wherein the polypeptide has an amino acid sequence of at least 90% sequence identity, based on the Clustal V method of alignment, when compared to SEQ ID NO:2, or
   (b) a complement of the nucleotide sequence, wherein the complement and the nucleotide sequence consist of the same number of nucleotides and are 100% complementary.

2. The polynucleotide of claim 1, wherein the amino acid sequence of the polypeptide has at least 95% sequence identity, based on the Clustal V method of alignment, when compared to SEQ ID NO:2.

3. The polynucleotide of claim 1, wherein the amino acid sequence of the polypeptide comprises SEQ ID NO:2.

4. The polynucleotide of claim 1 wherein the nucleotide sequence comprises SEQ ID NO:1.

5. A vector comprising the polynucleotide of claim 1.

6. A recombinant DNA construct comprising the polynucleotide of claim 1 operably linked to at least one regulatory sequence.

7. A method for transforming a cell, comprising transforming a cell with the polynucleotide of claim 1.

8. A cell comprising the recombinant DNA construct of claim 6.

9. A method for producing a plant comprising transforming a plant cell with the polynucleotide of claim 1 and regenerating a plant from the transformed plant cell.

10. A plant comprising the recombinant DNA construct of claim 6.

11. A seed comprising the recombinant DNA construct of claim 6.

* * * * *

SEQUENCE LISTING

<160> NUMBER OF SEQ ID NOS: 36

<210> SEQ ID NO 1
<211> LENGTH: 1982
<212> TYPE: DNA
<213> ORGANISM: Momordica charantia

<400> SEQUENCE: 1

```
gcacgagccg tcttctcaca atttgggggt ccgatttcac ttgcgcttga cgttcgtggg      60
gtgggattcc tatggctgtg ctcctggagg agattgtgaa gtccgttgag ttgtggttga     120
ggctgatcaa gaagcccccag ccgtacgtcg atcccaacct cgatccggtt cttctgattc     180
ccggagttgc agggtcgatt ttgaatgcgg taaatgagga caccggcagg gaggagcgtg     240
tttgggtcag gattttaggg gccgattcta agttccgaac tgagctctgg tcttttttacg     300 attccgcttc tggtgagtct gtatgttttg atccgaagac caaaattaga gttcctgatg     360
agagaagtgg attgtatgca atagatattt tggaccctga cctgatgatc ggatgcgatt     420
ctatatacta tttccatgac atgattgttg aaatgaccaa gtggggtttt caagaaggaa     480
aaactctttt tggatttgga tacgattttc ggcaaagtaa caggttgcca gaatcattgg     540
atcgtttagc tgctaaactg gaggcagtat ttagtgcttc aggagggaaa aagattaata     600
ttataagtca ctctatgggt ggtctttag tgaaatgctt catgtgcctg cgcagcgaaa     660
tctttgagaa gtatgtgcag aattggattg caattgctgc tccattccag ggtgcacctg     720
gatatgttac atctacctt gtgaatggaa tgtcatttgt caacggatgg aaacagaact     780
tctttatatc aaagtggagc atgcaccaac tgcttattga atgtccatcc atttacgaac     840
```

-continued

```
taatgggttc tccggacttt aattggcaac atattcctct tctagaaatc tggagacaga      900
aacatgatga cgatgggaac cctcacaatg tgttggaatc ttacctgctt aaagaaagtg      960
ttgaaatact gacagaatct ctttcaacaa acgcgattct tcatgatgga ttgactattc     1020
ccctgccatt taatttggag attttgaaat gggcaaacga gacacgggaa gttttaaaga     1080
atgctaaact tccttctcag gttaagtttt acaatatata tgcgacgggt cttgagacac     1140
cacatactgt ttgctatgga gatgcggaaa agccagttgc tgatttacat aatctacgat     1200
atattgagcc caattatatt tatgttgatg gtgatggcac ggttcctgtg gagtcggcaa     1260
aggctgatgg actcgatgca gtagcacgga tcggggtgcc cggtgagcac cagcgggttc     1320
ttagagacca ccgcgtcttc cggaggctca agcactggct caaggcaggt gatcctgatc     1380
ccttctatga cccgctaaac gactatgtga tcttgccaac agctttcgag gtcgaaagtc     1440
atgtggagaa aggtttgcaa gtagcagctc tgaaagagga atgggaaatc atctcccatg     1500
accaaaataa gacagatgag ttatgtaatg acaagccatt ggtgagttcc attatgctat     1560
ctcgagttac tgaggattgc ccgtcctcga gggccgaggc ttgcgcaact gttgtagttc     1620
atccccagca agacggtaag cagcacgtcg aactgaatgc tgttagtgta tcagttgatg     1680
catgaaagtg gcgcggcctg ttcttccaaa cccgactgca atcagcctca tgagcatttg     1740
ccattgatgc cgtttgatcg aatatctgta cagtcattat cacttgttta tgtggtgaga     1800
aatgtatatt aaaatttaga ttttctttta ttttttatta tttttttatg tatatagaag     1860
agacataact aaatgatcgt ttccttgcag tgctttaata atgggagaat ttaatcatgt     1920
aaatagaaat ataatgatt tagttgtttg tttgttaaaa aaaaaaaaaa aaaaaaaaa      1980
aa                                                                   1982
```

<210> SEQ ID NO 2
<211> LENGTH: 537
<212> TYPE: PRT
<213> ORGANISM: Momordica charantia

<400> SEQUENCE: 2

```
Met Ala Val Leu Leu Glu Glu Ile Val Lys Ser Val Glu Leu Trp Leu
 1               5                  10                  15

Arg Leu Ile Lys Lys Pro Gln Pro Tyr Val Asp Pro Asn Leu Asp Pro
            20                  25                  30

Val Leu Leu Ile Pro Gly Val Ala Gly Ser Ile Leu Asn Ala Val Asn
        35                  40                  45

Glu Asp Thr Gly Arg Glu Glu Arg Val Trp Val Arg Ile Leu Gly Ala
    50                  55                  60

Asp Ser Lys Phe Arg Thr Glu Leu Trp Ser Phe Tyr Asp Ser Ala Ser
65                  70                  75                  80

Gly Glu Ser Val Cys Phe Asp Pro Lys Thr Lys Ile Arg Val Pro Asp
                85                  90                  95

Glu Arg Ser Gly Leu Tyr Ala Ile Asp Ile Leu Asp Pro Asp Leu Met
            100                 105                 110

Ile Gly Cys Asp Ser Ile Tyr Tyr Phe His Asp Met Ile Val Glu Met
        115                 120                 125

Thr Lys Trp Gly Phe Gln Glu Gly Lys Thr Leu Phe Gly Phe Gly Tyr
    130                 135                 140

Asp Phe Arg Gln Ser Asn Arg Leu Pro Glu Ser Leu Asp Arg Leu Ala
145                 150                 155                 160
```

```
Ala Lys Leu Glu Ala Val Phe Ser Ala Ser Gly Gly Lys Lys Ile Asn
                165                 170                 175
Ile Ile Ser His Ser Met Gly Gly Leu Leu Val Lys Cys Phe Met Cys
                180                 185                 190
Leu Arg Ser Glu Ile Phe Glu Lys Tyr Val Gln Asn Trp Ile Ala Ile
                195                 200                 205
Ala Ala Pro Phe Gln Gly Ala Pro Gly Tyr Val Thr Ser Thr Phe Val
210                 215                 220
Asn Gly Met Ser Phe Val Asn Gly Trp Lys Gln Asn Phe Phe Ile Ser
225                 230                 235                 240
Lys Trp Ser Met His Gln Leu Leu Ile Glu Cys Pro Ser Ile Tyr Glu
                245                 250                 255
Leu Met Gly Ser Pro Asp Phe Asn Trp Gln His Ile Pro Leu Leu Glu
                260                 265                 270
Ile Trp Arg Gln Lys His Asp Asp Gly Asn Pro His Asn Val Leu
                275                 280                 285
Glu Ser Tyr Leu Leu Lys Glu Ser Val Glu Ile Leu Thr Glu Ser Leu
                290                 295                 300
Ser Thr Asn Ala Ile Leu His Asp Gly Leu Thr Ile Pro Leu Pro Phe
305                 310                 315                 320
Asn Leu Glu Ile Leu Lys Trp Ala Asn Glu Thr Arg Glu Val Leu Lys
                325                 330                 335
Asn Ala Lys Leu Pro Ser Gln Val Lys Phe Tyr Asn Ile Tyr Ala Thr
                340                 345                 350
Gly Leu Glu Thr Pro His Thr Val Cys Tyr Gly Asp Ala Glu Lys Pro
                355                 360                 365
Val Ala Asp Leu His Asn Leu Arg Tyr Ile Glu Pro Asn Tyr Ile Tyr
370                 375                 380
Val Asp Gly Asp Gly Thr Val Pro Val Glu Ser Ala Lys Ala Asp Gly
385                 390                 395                 400
Leu Asp Ala Val Ala Arg Ile Gly Val Pro Gly Glu His Gln Arg Val
                405                 410                 415
Leu Arg Asp His Arg Val Phe Arg Arg Leu Lys His Trp Leu Lys Ala
                420                 425                 430
Gly Asp Pro Asp Pro Phe Tyr Asp Pro Leu Asn Asp Tyr Val Ile Leu
                435                 440                 445
Pro Thr Ala Phe Glu Val Glu Ser His Val Glu Lys Gly Leu Gln Val
450                 455                 460
Ala Ala Leu Lys Glu Glu Trp Glu Ile Ile Ser His Asp Gln Asn Lys
465                 470                 475                 480
Thr Asp Glu Leu Cys Asn Asp Lys Pro Leu Val Ser Ser Ile Met Leu
                485                 490                 495
Ser Arg Val Thr Glu Asp Cys Pro Ser Ser Arg Ala Glu Ala Cys Ala
                500                 505                 510
Thr Val Val Val His Pro Gln Gln Asp Gly Lys Gln His Val Glu Leu
                515                 520                 525
Asn Ala Val Ser Val Ser Val Asp Ala
                530                 535

<210> SEQ ID NO 3
<211> LENGTH: 1788
<212> TYPE: DNA
<213> ORGANISM: Calendula officinalis

<400> SEQUENCE: 3
```

-continued

```
gcaccagatt catactttgg gttttaggat ggcggtgttg ctggttgatg tagttaaagc      60
agtagaggca tggttaaaga ttcttaagga accagagcct acgttgatc cgaatcttga      120
cccggttctt attgttcctg ggattgctgg ttcgattctt catgctaaag atgctgaaac      180
tgggaaagaa gagcgtgttt gggttcggat ctgggaagct gatcgtgagt tcgtgctaa      240
actttggtgc caatttgatt ctgaaactgg caaaactgtt tctttggatc ccaacatcag      300
catcgttgtc cctgaggaca gaaacgggct ttatgcaatt gattgtttgg atcccaatat      360
gattattggg cgtgatagtg tatgctattt ccatgatatg ataaatgaaa tgacaagttg      420
gggataccaa gaggaaaaa cgctattcgg ttttggatat gatttccgac aaagcaatag      480
acttaaagaa acaatggatc gtcttgctgc aaaattggat gcaatttata ctgcttcagg      540
agggaaaaag ataactgtaa ttactcattc aatgggtgga cttgttgtca atgttttat      600
gagtctgcac actgatattt ttgagaaata tgttaagagt tggatagcaa ttgctgcacc      660
atttcagggt gcacctggat atgtaacatc tacattaatg aatgggatgt catttgtgga      720
aggttgggaa gcaaactttt ttgtatccaa gtggagtatg catcaactgc tgattgaatg      780
tccatccata tatgaattaa tggcctgttt ggactatgaa tgggaacatc ttcctctttt      840
acaaatttgg aaagaaattc aggatgaaaa cggtaattct actcccatgc tggagacatt      900
taccccaatg gaatctgttt ccattttcac tcaggccctt tcagtcaatg agttgagctt      960
tgatggagtg gatattcctc taccatttaa caaagaaata ttgcaatggg ctaataaaac      1020
acgagagatc ttatcttcag ccaaacttcc atcaagtgtt aaattctata cgtctatgg      1080
cactggtctt gacactcccc agagtgtatg ttatggaagt gctgattcac ccgtctcaaa      1140
cctattggaa ctaccatttc tagatgcaac ttatgtgaat gttgaaggtg atggaactgt      1200
acctgtagaa tctgccaggg ctgatgggct ggatgcagaa gctagggttg aatcccagg      1260
tgaacataga ggaattttat gtgacaaaca cctattcagg atagtgaaac actggctaaa      1320
agcagatcat gatccctttt acaatcctgt taacgattat gtaatcctac caactttatt      1380
tgagatcaca aaacatcagg acagcaaaga gggcaaagaa gtaatttcac tcaaagaaga      1440
atgggaaatt gtttcaaaag agcaacaaga tgagcctatg attgggtcaa tttctgcttc      1500
tcgtgttggt gatgatggtt gtgaagaaga agcacgtgca acttttgttg ttcatccaca      1560
aagtaatggt aaacagaata ttcaacttaa tgcggtgagt gtttctgctg gtggtgcgta      1620
aatttgtcat ttgtaattgt ggttgatgaa gttatgtggc gttttctggt aatgtgtata      1680
tatttcagtg tttgtaatga attgaagtga ataaataaaa gaataaagat ggaaaaagaa      1740
gtggttggct tgaaaaaaaa aaaaaaaaaa aaaaaaaaaa aaaaaaaa                  1788
```

<210> SEQ ID NO 4
<211> LENGTH: 530
<212> TYPE: PRT
<213> ORGANISM: Calendula officinalis

<400> SEQUENCE: 4

Met Ala Val Leu Leu Val Asp Val Val Lys Ala Val Glu Ala Trp Leu
1               5                   10                  15

Lys Ile Leu Lys Glu Pro Glu Pro Tyr Val Asp Pro Asn Leu Asp Pro
            20                  25                  30

Val Leu Ile Val Pro Gly Ile Ala Gly Ser Ile Leu His Ala Lys Asp
        35                  40                  45

Ala Glu Thr Gly Lys Glu Glu Arg Val Trp Val Arg Ile Trp Glu Ala

-continued

```
                50                    55                    60
Asp Arg Glu Phe Arg Ala Lys Leu Trp Cys Gln Phe Asp Ser Glu Thr
 65                      70                      75                      80

Gly Lys Thr Val Ser Leu Asp Pro Asn Ile Ser Ile Val Pro Glu
                     85                      90                      95

Asp Arg Asn Gly Leu Tyr Ala Ile Asp Cys Leu Asp Pro Asn Met Ile
                    100                     105                     110

Ile Gly Arg Asp Ser Val Cys Tyr Phe His Asp Met Ile Asn Glu Met
                    115                     120                     125

Thr Ser Trp Gly Tyr Gln Glu Gly Lys Thr Leu Phe Gly Phe Gly Tyr
                    130                     135                     140

Asp Phe Arg Gln Ser Asn Arg Leu Lys Glu Thr Met Asp Arg Leu Ala
145                     150                     155                     160

Ala Lys Leu Asp Ala Ile Tyr Thr Ala Ser Gly Gly Lys Lys Ile Thr
                    165                     170                     175

Val Ile Thr His Ser Met Gly Gly Leu Val Val Lys Cys Phe Met Ser
                    180                     185                     190

Leu His Thr Asp Ile Phe Glu Lys Tyr Val Lys Ser Trp Ile Ala Ile
                    195                     200                     205

Ala Ala Pro Phe Gln Gly Ala Pro Gly Tyr Val Thr Ser Thr Leu Met
                    210                     215                     220

Asn Gly Met Ser Phe Val Glu Gly Trp Glu Ala Asn Phe Phe Val Ser
225                     230                     235                     240

Lys Trp Ser Met His Gln Leu Leu Ile Glu Cys Pro Ser Ile Tyr Glu
                    245                     250                     255

Leu Met Ala Cys Leu Asp Tyr Glu Trp Glu His Leu Pro Leu Leu Gln
                    260                     265                     270

Ile Trp Lys Glu Ile Gln Asp Glu Asn Gly Asn Ser Thr Pro Met Leu
                    275                     280                     285

Glu Thr Phe Thr Pro Met Glu Ser Val Ser Ile Phe Thr Gln Ala Leu
                    290                     295                     300

Ser Val Asn Glu Leu Ser Phe Asp Gly Val Asp Ile Pro Leu Pro Phe
305                     310                     315                     320

Asn Lys Glu Ile Leu Gln Trp Ala Asn Lys Thr Arg Glu Ile Leu Ser
                    325                     330                     335

Ser Ala Lys Leu Pro Ser Ser Val Lys Phe Tyr Asn Val Tyr Gly Thr
                    340                     345                     350

Gly Leu Asp Thr Pro Gln Ser Val Cys Tyr Gly Ser Ala Asp Ser Pro
                    355                     360                     365

Val Ser Asn Leu Leu Glu Leu Pro Phe Leu Asp Ala Thr Tyr Val Asn
                    370                     375                     380

Val Glu Gly Asp Gly Thr Val Pro Val Glu Ser Ala Arg Ala Asp Gly
385                     390                     395                     400

Leu Asp Ala Glu Ala Arg Val Gly Ile Pro Gly Glu His Arg Gly Ile
                    405                     410                     415

Leu Cys Asp Lys His Leu Phe Arg Ile Val Lys His Trp Leu Lys Ala
                    420                     425                     430

Asp His Asp Pro Phe Tyr Asn Pro Val Asn Asp Tyr Val Ile Leu Pro
                    435                     440                     445

Thr Leu Phe Glu Ile Thr Lys His Gln Asp Ser Lys Glu Gly Lys Glu
                    450                     455                     460

Val Ile Ser Leu Lys Glu Glu Trp Glu Ile Val Ser Lys Glu Gln Gln
465                     470                     475                     480
```

```
Asp Glu Pro Met Ile Gly Ser Ile Ser Ala Ser Arg Val Gly Asp Asp
            485                 490                 495
Gly Cys Glu Glu Glu Ala Arg Ala Thr Phe Val Val His Pro Gln Ser
        500                 505                 510
Asn Gly Lys Gln Asn Ile Gln Leu Asn Ala Val Ser Val Ser Ala Gly
        515                 520                 525
Gly Ala
    530

<210> SEQ ID NO 5
<211> LENGTH: 2046
<212> TYPE: DNA
<213> ORGANISM: Eucalyptus grandis

<400> SEQUENCE: 5
gcaccagaat tcgagcccta attccccacc attctccccc aaatcctcgc cgccgatcgc      60
ctccgtcctt ccgccgctgc cgccgccgat cgccccccgg aaatccgacc tcgaagcgag     120
agtccccccc ggacggacga gcggcgactt ggcggcggag ggcgagattg cgacggcgcc     180
gggaccgggt gtgttagggc tttgattgcg ggcggatggc ggtgctgttg gaggacatcc     240
tgcagtccgt ggagcagtgg ctgaagctga tcaggaagcc ccagccctac gtggacccga     300
acctcgaccc ggtcctcctc gtgcccgggg tcgccggatc gatactgcac gccgtcgacg     360
gcagcaacgg caagggcgag agggtctggg tccggatctt cggggccgac tacaagtgcc     420
ggaccaagct ctggtctcgc ttcgaccctg ccgtcggtaa accgtttcc ttagatccta     480
agacgaacat cgtggttcct gaagacagat atggactgta tgccattgat gttttggacc     540
ctgatatggt ccttgggcgt gattgtgtat actatttcca tgacatgata gtcgaaatga     600
tcaaatgggg ttttcaggaa gggaagacat gttcggtttt gggtatgac ttcaggcaaa     660
gtaacaggtt tcaagaaaca atggagtgtt tggctgcaaa gttggaatct gtatataatg     720
ctgcgggagg gaagaagatg accattatca gtcactctat gggaggtctt ctagtgaagt     780
gctttatgtg cctgcacagt gatatttttg caaagtatgt gaagaattgg attgctatag     840
ctgcaccttt tcaaggtgcc cctggatatg tcacatctac ctttctgaat gggatgtcat     900
tgtggatgg tgggagcaa acttttttca tttcaaagtg gagcatgcat cagctgctga     960
ttgaatgccc atcaatctat gaattgatgg catgtccaaa ctttacctgg aacatgccc    1020
cagtgttaga gatctggagg aagaagcttg atgattgtgg tgataccgtg atgatccttg    1080
agtcttacac cccttccgag agtgtaaata tattcgctga agcactttca gtaatacgg    1140
ttgattatga tggtgagagc atttccttac catttaacca ggaaatcttg aaatgggctc    1200
atgagacccg taggatttta tcttgtgcta agttccgcc cggggtgaaa ttctacaaca    1260
tatatgcgac caatctggag acaccacaca gtgtttgcta tggcagtgag acatgcctg    1320
ttacggactt gcaagaactt caattttacc tgcctgatta tatatgtgtt gatggtgatg    1380
gaacagttcc gactgaatca gctaaggcag atgggcttga agcagttgca agagttggag    1440
tacccgggga gcaccgggga attctgtgtg atcatcatgt tttccgcatt ctgaagcact    1500
ggctaaaggc agattcagac ccctactata acccgcttaa cgactatgtg attctaccca    1560
ccacgtttga gatggaaaga caccacgaga agggcatgga ggtgacttca ctcaaagagg    1620
agtgggaaat catttccaaa gatgccaatg atgaccaagg agaggttacc ataatgccct    1680
cagtaagcac cataaccgtt tcccaagaca gaggtcacca atcttatcgg gccgaggctt    1740
```

```
gtgccactgt gaccgtgcac ccccaaaatg agggcaagca acaggttgag ctcaatgcct      1800
tgagtgtatc tgttgatgcc taaatttagt tacttgcact gtgtgaaaga aaagcccgca      1860
attggggcag tgctgtgtat agtagtatgt tggtcgtgta caaaatgtgc gtattgtaaa      1920
tataaggatc actggtggca attgccttga tgaaccataa cattggaaga tcgttctggg      1980
ttttgtaatg aagacccat catctaaaaa aaaaaaaaaa aaaaaaaaaa aaaaaaaaaa      2040
aaaaaa                                                                2046

<210> SEQ ID NO 6
<211> LENGTH: 535
<212> TYPE: PRT
<213> ORGANISM: Eucalyptus grandis

<400> SEQUENCE: 6
```

Met Ala Val Leu Leu Glu Asp Ile Leu Gln Ser Val Glu Gln Trp Leu
 1               5                  10                  15

Lys Leu Ile Arg Lys Pro Gln Pro Tyr Val Asp Pro Asn Leu Asp Pro
             20                  25                  30

Val Leu Leu Val Pro Gly Val Ala Gly Ser Ile Leu His Ala Val Asp
         35                  40                  45

Gly Ser Asn Gly Lys Gly Glu Arg Val Trp Val Arg Ile Phe Gly Ala
     50                  55                  60

Asp Tyr Lys Cys Arg Thr Lys Leu Trp Ser Arg Phe Asp Pro Ala Val
 65                  70                  75                  80

Gly Lys Thr Val Ser Leu Asp Pro Lys Thr Asn Ile Val Val Pro Glu
                 85                  90                  95

Asp Arg Tyr Gly Leu Tyr Ala Ile Asp Val Leu Asp Pro Asp Met Val
            100                 105                 110

Leu Gly Arg Asp Cys Val Tyr Tyr Phe His Asp Met Ile Val Glu Met
        115                 120                 125

Ile Lys Trp Gly Phe Gln Glu Gly Lys Thr Leu Phe Gly Phe Gly Tyr
    130                 135                 140

Asp Phe Arg Gln Ser Asn Arg Phe Gln Glu Thr Met Glu Cys Leu Ala
145                 150                 155                 160

Ala Lys Leu Glu Ser Val Tyr Asn Ala Ala Gly Gly Lys Lys Met Thr
                165                 170                 175

Ile Ile Ser His Ser Met Gly Gly Leu Leu Val Lys Cys Phe Met Cys
            180                 185                 190

Leu His Ser Asp Ile Phe Ala Lys Tyr Val Lys Asn Trp Ile Ala Ile
        195                 200                 205

Ala Ala Pro Phe Gln Gly Ala Pro Gly Tyr Val Thr Ser Thr Phe Leu
    210                 215                 220

Asn Gly Met Ser Phe Val Asp Gly Trp Glu Gln Asn Phe Phe Ile Ser
225                 230                 235                 240

Lys Trp Ser Met His Gln Leu Leu Ile Glu Cys Pro Ser Ile Tyr Glu
                245                 250                 255

Leu Met Ala Cys Pro Asn Phe Thr Trp Glu His Ala Pro Val Leu Glu
            260                 265                 270

Ile Trp Arg Lys Lys Leu Asp Asp Cys Gly Asp Thr Arg Met Ile Leu
        275                 280                 285

Glu Ser Tyr Thr Pro Ser Glu Ser Val Asn Ile Phe Ala Glu Ala Leu
    290                 295                 300

Ser Ser Asn Thr Val Asp Tyr Asp Gly Glu Ser Ile Ser Leu Pro Phe
305                 310                 315                 320

```
Asn Gln Glu Ile Leu Lys Trp Ala His Glu Thr Arg Arg Ile Leu Ser
            325                 330                 335

Cys Ala Lys Val Pro Pro Gly Val Lys Phe Tyr Asn Ile Tyr Ala Thr
            340                 345                 350

Asn Leu Glu Thr Pro His Ser Val Cys Tyr Gly Ser Glu Asp Met Pro
            355                 360                 365

Val Thr Asp Leu Gln Glu Leu Gln Phe Tyr Leu Pro Asp Tyr Ile Cys
    370                 375                 380

Val Asp Gly Asp Gly Thr Val Pro Thr Glu Ser Ala Lys Ala Asp Gly
385                 390                 395                 400

Leu Glu Ala Val Ala Arg Val Gly Val Pro Gly Glu His Arg Gly Ile
                405                 410                 415

Leu Cys Asp His His Val Phe Arg Ile Leu Lys His Trp Leu Lys Ala
            420                 425                 430

Asp Ser Asp Pro Tyr Tyr Asn Pro Leu Asn Asp Tyr Val Ile Leu Pro
            435                 440                 445

Thr Thr Phe Glu Met Glu Arg His His Glu Lys Gly Met Glu Val Thr
    450                 455                 460

Ser Leu Lys Glu Glu Trp Glu Ile Ile Ser Lys Asp Ala Asn Asp Asp
465                 470                 475                 480

Gln Gly Glu Val Thr Ile Met Pro Ser Val Ser Thr Ile Thr Val Ser
                485                 490                 495

Gln Asp Arg Gly His Gln Ser Tyr Arg Ala Glu Ala Cys Ala Thr Val
            500                 505                 510

Thr Val His Pro Gln Asn Glu Gly Lys Gln Gln Val Glu Leu Asn Ala
            515                 520                 525

Leu Ser Val Ser Val Asp Ala
            530                 535

<210> SEQ ID NO 7
<211> LENGTH: 2043
<212> TYPE: DNA
<213> ORGANISM: Vitis sp.

<400> SEQUENCE: 7
gcttctctct ccaattaaca actcgtctcc aaacccccaat ttcatccgat tttcatctca    60
aattcatctc tagttttcga tcgttgtgtc tggtggtcgc caagtttgaa tccgcttgcg   120
gctaaagttt ctcagaattt ggaatcggag ggataggtta gatgcatttg tcggaattga   180
gttgcgatta gggtttcgga gatggcggtg ttgttggagg agatagcgca gtcggtggag   240
atatggttga agctgattaa gaaacctcag ccgtacgttg accccaatct tgacccggtt   300
ctgttggtgc ccggcatcgc cggttcgatc ctgaaagccg tcgacgacaa tggtcgcggc   360
gagcgggttt gggtccggat aatcggtgcc gattacaagt tccggactaa gctttggtcg   420
cgatttgacc cctctactgg tcaaacagtg tctttagatc caaaaaccca tattgtggtc   480
cctgaagaga gatatggatt gcatgcaatt gatgtcttgg atcctgaaat gattattggg   540
cgtgattgtg tttattattt ccatgacatg atagttgaaa tgatgaaatg gggttttcaa   600
gagggaaaaa cactatttgg ttttggttat gatttccgcc aaagtaacag gtttcaggaa   660
acactagagc gctttgctgc gaaactggag gctgtgtaca ccgcctcagg aggaaaaaaa   720
ataaacataa taagtcattc tatgggggt ctacttgtga atgtttcat gagtttacac     780
actgatatct tgagaagta tgtgcagaac tggatagcaa ttgctgcacc attccagggt    840
```

```
gcacctggat atatctcatc gacatttctg aatggaatgt catttgtgga aggttgggaa    900
cagaattttt ttatatcaaa atggagcatg caccagctgc ttattgaatg tccatcaata    960
tatgaattga tggcttgtcc ggattttcaa tgggaacaca atccactttt ggaaatttgg   1020
agagagaagc atgataagga tggtaactct aacattgttc tggagtctta ttccccagaa   1080
gaaagtgttc caatttttaa ggaagctctt tccagtaata cggttaatta cgatggattg   1140
gacattcctc tacctttcaa tttagagatc ttgcaatggg cttgtgaaac acgcaagatc   1200
ttatcttgtg ctaaggttcc ttctcaagtt aaattttaca atatatatgg gatgaacctc   1260
gagacgcctc atagtgtttg ttatggaagt gtggaagaac ctgttacaga tctagagcaa   1320
ttaaaatttg tccaggctca atatgtatgc gttgatggtg atgggactgt tccagtggaa   1380
tcagcaatgg cggatgggct tactgcagaa gcaaggattg gagtccctgg tgagcaccgg   1440
ggaatccttg ctgaaccgca tgtatttcgg attctaaaac actggctgaa ggcaggggac   1500
ccagatcctt actacaatcc tctaaacgat tacgtgatcc tgcccactgc atttgaaatg   1560
gagaggcaca agagagagg cctgcaggtg acttccctca agaagaatg ggaaatcatc   1620 tctagagact caaacgatga ggacaatatc atcgtcaaca acgggaagcc tctggtaagc   1680
tcaatagctg tttctgatca gtcatctctg acagaggctc gagccaccgt cactcttcac   1740
ccccagagtg agggcaagcg acacattgaa ctaaatgcca taagcgtttc tgcaactgtt   1800
taaaacccag ttggtggtga aaaattgtca tcagctctgg gattcaatgg tctctactgt   1860
atagttgcta ttccttcagt ttgaactttg aagccggtat cccttgtgcc tcttgtgtgt   1920
atatagtgtt cctggaagaa gggtttcatg taagatctat tctggacaaa ttcattcatg   1980
ggatatatga atatatgcat atatacatat atataatatt tgttaaaaaa aaaaaaaaa   2040 aaa                                                                 2043
```

<210> SEQ ID NO 8
<211> LENGTH: 533
<212> TYPE: PRT
<213> ORGANISM: Vitis sp.

<400> SEQUENCE: 8

```
Met Ala Val Leu Leu Glu Glu Ile Ala Gln Ser Val Glu Ile Trp Leu
  1               5                  10                  15

Lys Leu Ile Lys Lys Pro Gln Pro Tyr Val Asp Pro Asn Leu Asp Pro
                 20                  25                  30

Val Leu Leu Val Pro Gly Ile Ala Gly Ser Ile Leu Lys Ala Val Asp
             35                  40                  45

Asp Asn Gly Arg Gly Glu Arg Val Trp Val Arg Ile Ile Gly Ala Asp
         50                  55                  60

Tyr Lys Phe Arg Thr Lys Leu Trp Ser Arg Phe Asp Pro Ser Thr Gly
 65                  70                  75                  80

Gln Thr Val Ser Leu Asp Pro Lys Thr His Ile Val Val Pro Glu Glu
                 85                  90                  95

Arg Tyr Gly Leu His Ala Ile Asp Val Leu Asp Pro Glu Met Ile Ile
                100                 105                 110

Gly Arg Asp Cys Val Tyr Tyr Phe His Asp Met Ile Val Glu Met Met
            115                 120                 125

Lys Trp Gly Phe Gln Glu Gly Lys Thr Leu Phe Gly Phe Gly Tyr Asp
        130                 135                 140

Phe Arg Gln Ser Asn Arg Phe Gln Glu Thr Leu Glu Arg Phe Ala Ala
145                 150                 155                 160
```

```
Lys Leu Glu Ala Val Tyr Thr Ala Ser Gly Gly Lys Lys Ile Asn Ile
                165                 170                 175

Ile Ser His Ser Met Gly Gly Leu Leu Val Lys Cys Phe Met Ser Leu
            180                 185                 190

His Thr Asp Ile Phe Glu Lys Tyr Val Gln Asn Trp Ile Ala Ile Ala
        195                 200                 205

Ala Pro Phe Gln Gly Ala Pro Gly Tyr Ile Ser Thr Phe Leu Asn
    210                 215                 220

Gly Met Ser Phe Val Glu Gly Trp Glu Gln Asn Phe Phe Ile Ser Lys
225                 230                 235                 240

Trp Ser Met His Gln Leu Leu Ile Glu Cys Pro Ser Ile Tyr Glu Leu
                245                 250                 255

Met Ala Cys Pro Asp Phe Gln Trp Glu His Asn Pro Leu Leu Glu Ile
            260                 265                 270

Trp Arg Glu Lys His Asp Lys Asp Gly Asn Ser Asn Ile Val Leu Glu
        275                 280                 285

Ser Tyr Ser Pro Glu Glu Ser Val Pro Ile Phe Lys Glu Ala Leu Ser
    290                 295                 300

Ser Asn Thr Val Asn Tyr Asp Gly Leu Asp Ile Pro Leu Pro Phe Asn
305                 310                 315                 320

Leu Glu Ile Leu Gln Trp Ala Cys Glu Thr Arg Lys Ile Leu Ser Cys
                325                 330                 335

Ala Lys Val Pro Ser Gln Val Lys Phe Tyr Asn Ile Tyr Gly Met Asn
            340                 345                 350

Leu Glu Thr Pro His Ser Val Cys Tyr Gly Ser Val Glu Glu Pro Val
        355                 360                 365

Thr Asp Leu Glu Gln Leu Lys Phe Val Gln Ala Gln Tyr Val Cys Val
    370                 375                 380

Asp Gly Asp Gly Thr Val Pro Val Glu Ser Ala Met Ala Asp Gly Leu
385                 390                 395                 400

Thr Ala Glu Ala Arg Ile Gly Val Pro Gly Glu His Arg Gly Ile Leu
                405                 410                 415

Ala Glu Pro His Val Phe Arg Ile Leu Lys His Trp Leu Lys Ala Gly
            420                 425                 430

Asp Pro Asp Pro Tyr Tyr Asn Pro Leu Asn Asp Tyr Val Ile Leu Pro
        435                 440                 445

Thr Ala Phe Glu Met Glu Arg His Lys Glu Arg Gly Leu Gln Val Thr
    450                 455                 460

Ser Leu Lys Glu Glu Trp Glu Ile Ile Ser Arg Asp Ser Asn Asp Glu
465                 470                 475                 480

Asp Asn Ile Ile Val Asn Asn Gly Lys Pro Leu Val Ser Ser Ile Ala
                485                 490                 495

Val Ser Asp Gln Ser Ser Leu Thr Glu Ala Arg Ala Thr Val Thr Leu
            500                 505                 510

His Pro Gln Ser Glu Gly Lys Arg His Ile Glu Leu Asn Ala Ile Ser
        515                 520                 525

Val Ser Ala Thr Val
    530

<210> SEQ ID NO 9
<211> LENGTH: 1438
<212> TYPE: DNA
<213> ORGANISM: Oryza sativa
```

<400> SEQUENCE: 9

```
tctctctctc ggaaaacatt atttggattt ggttatgatt tccgccagag taacaggctt    60
tcagaaacac ttgatagatt ttccagaaag ttggagtcag tttacatagc ttccggagaa   120
aaaaagatca atctcattac tcattcaatg ggaggattgc ttgtcaaatg cttcatgtcc   180
ctccatagtg atgtcttcga gaaatacata aagagttgga ttgcaattgc tgcaccattt   240
caaggtgcac ctgggtacat aactactagt ctgctgaatg gtatgtcttt tgtcgaagga   300
tgggagtcaa gattctttat ttccaagtgg agtatgcagc aattgttgct cgaatgccca   360
tcaatttacg aattgttggc taactcgacc ttccaatggg aagatactcc atatctgcag   420
atctggagac agaaattgga tactaatggc aagaaaagtg ccatgttaga gtcatatgag   480
ccagatgaag caataaaaat gattagagaa gctctttcca agcatgagat catttctgat   540
ggtatgcaca ttccattgcc ccttgatatg gatatattga tgggcaaa agagacacag    600
gatgttttgt gcaatgcaaa gcttccaaaa tcagtgaagt tctacaatat ttacggaact   660
gattatgaca ctgcccatac cgttcgctac gggagtgaac accatccaat ttcaaatctc   720
agtgacctct tgtatactca gtcaggcaac tacatctgtg ttgatggtga tggatctgtc   780
cctgtagaat cagcaaaggc agatggcctc gatgcagtgg caagagttgg ggttgctgca   840
gaccaccgag gaatcgtctg tgatcgtcac gtgttccgga taattcagca ctggctccat   900
gccggtgagc ctgacccatt ctacgatccc ctcaacgact acgtcatact cccaacagcc   960
ttcgagatcg agaagtacca cgagaaacac ggggatatca catcggttag agaggactgg  1020
gagatcatct cccatcgcga tgacgaaagc aagaggccag ccgagcttcc tcctatgttc  1080
aacacgctat cggcgtcccg cgagggtgaa gacggctcgc tggaagaggc gcaggcgacg  1140
atctttgttc atccagagag caaagggagg cagcatgtgg aagttagggc agttggagtc  1200
acccatgacg gctagtcaag ccagtctac gaaaacacac ggttgtcaac tagctagtct   1260
gcacactcca aagcaaagtg gacaatgtaa atataagacg tccctagcta tgaactacgt  1320
gtaattttgc tgccttgtaa ataccagaac tgaaaatata ctgccactgg atgatgatac  1380
gaatagaaag gagaaagaaa aggatgaact tgatatgtta aaaaaaaaaa aaaaaaaa    1438
```

<210> SEQ ID NO 10
<211> LENGTH: 404
<212> TYPE: PRT
<213> ORGANISM: Oryza sativa

<400> SEQUENCE: 10

```
Ser Leu Ser Arg Lys Thr Leu Phe Gly Phe Gly Tyr Asp Phe Arg Gln
  1               5                  10                  15

Ser Asn Arg Leu Ser Glu Thr Leu Asp Arg Phe Ser Arg Lys Leu Glu
             20                  25                  30

Ser Val Tyr Ile Ala Ser Gly Glu Lys Lys Ile Asn Leu Ile Thr His
         35                  40                  45

Ser Met Gly Gly Leu Leu Val Lys Cys Phe Met Ser Leu His Ser Asp
     50                  55                  60

Val Phe Glu Lys Tyr Ile Lys Ser Trp Ile Ala Ile Ala Ala Pro Phe
 65                  70                  75                  80

Gln Gly Ala Pro Gly Tyr Ile Thr Thr Ser Leu Leu Asn Gly Met Ser
                 85                  90                  95

Phe Val Glu Gly Trp Glu Ser Arg Phe Phe Ile Ser Lys Trp Ser Met
            100                 105                 110
```

```
Gln Gln Leu Leu Leu Glu Cys Pro Ser Ile Tyr Glu Leu Leu Ala Asn
        115                 120                 125

Ser Thr Phe Gln Trp Glu Asp Thr Pro Tyr Leu Gln Ile Trp Arg Gln
        130                 135                 140

Lys Leu Asp Thr Asn Gly Lys Lys Ser Ala Met Leu Glu Ser Tyr Glu
145                 150                 155                 160

Pro Asp Glu Ala Ile Lys Met Ile Arg Glu Ala Leu Ser Lys His Glu
                165                 170                 175

Ile Ile Ser Asp Gly Met His Ile Pro Leu Pro Leu Asp Met Asp Ile
                180                 185                 190

Leu Arg Trp Ala Lys Glu Thr Gln Asp Val Leu Cys Asn Ala Lys Leu
            195                 200                 205

Pro Lys Ser Val Lys Phe Tyr Asn Ile Tyr Gly Thr Asp Tyr Asp Thr
        210                 215                 220

Ala His Thr Val Arg Tyr Gly Ser Glu His His Pro Ile Ser Asn Leu
225                 230                 235                 240

Ser Asp Leu Leu Tyr Thr Gln Ser Gly Asn Tyr Ile Cys Val Asp Gly
                245                 250                 255

Asp Gly Ser Val Pro Val Glu Ser Ala Lys Ala Asp Gly Leu Asp Ala
                260                 265                 270

Val Ala Arg Val Gly Val Ala Ala Asp His Arg Gly Ile Val Cys Asp
            275                 280                 285

Arg His Val Phe Arg Ile Ile Gln His Trp Leu His Ala Gly Glu Pro
        290                 295                 300

Asp Pro Phe Tyr Asp Pro Leu Asn Asp Tyr Val Ile Leu Pro Thr Ala
305                 310                 315                 320

Phe Glu Ile Glu Lys Tyr His Glu Lys His Gly Asp Ile Thr Ser Val
                325                 330                 335

Arg Glu Asp Trp Glu Ile Ile Ser His Arg Asp Asp Glu Ser Lys Arg
            340                 345                 350

Pro Ala Glu Leu Pro Pro Met Phe Asn Thr Leu Ser Ala Ser Arg Glu
        355                 360                 365

Gly Glu Asp Gly Ser Leu Glu Glu Ala Gln Ala Thr Ile Phe Val His
        370                 375                 380

Pro Glu Ser Lys Gly Arg Gln His Val Glu Val Arg Ala Val Gly Val
385                 390                 395                 400

Thr His Asp Gly

<210> SEQ ID NO 11
<211> LENGTH: 1475
<212> TYPE: DNA
<213> ORGANISM: Vernonia mespilifolia
<220> FEATURE:
<221> NAME/KEY: unsure
<222> LOCATION: (1471)
<223> OTHER INFORMATION: n = a, c, g or t

<400> SEQUENCE: 11
aatcgattgc ttggatcctg atatgctcat tgggcgtgat agtgtatgct acttccatga      60
aatgataaat gaaatgacaa gctggggata cctagaagga aaaacgcttt ttgggtttgg     120
gtatgatttc cgacaaagca acagacttca agaaactatg gatcgtcttg ctacaaagtt     180
ggaatctatc tatacttctt caggggggaa aaaataaat gtaattactc attcaatggg     240
cggacttctt gtcaaatgtt ttatgagcct gcacagtgat attttgaga aatatgttaa     300 gaattggata gcaattgytg caccatttca gggtgctcct ggatatgtaa catytacatt     360
```

-continued

```
attgaatggg atgtcatttg tggaagggtg ggaagcatac tttttsrtat ccmagtggar    420
tatgcatcag ctgctgattg aatgtccatc catctatgaa ttgatggcct gtctggacta    480
tgaatgggaa catgatccat tgttacaaat ttggaaggag attcagaatg atgatggaaa    540
ctctaccact attctggaga cattcacccc agtggaagct gtttcgatct tcactcaggc    600
tctgtcaatc aacgagctga actatggtgg agtggatatc cctctaccat tcaacaaaga    660
aatattgcat tgggctaaca aaacacgaga gatcttgtct tcagccaaac ttccaccaaa    720
tgttaaattc tataatgtat atggcactgg tcgtgacact cctcagagtg tatgttacgg    780
aagcgcagac tcacccgtct cggacctaca ggaattaccg ttgctcgatg ctactttcat    840
caatgttgat ggtgatggga ccgtacccat ggaatctgca aaggctgatg ggctagacgc    900
agaagctagg gttggtatcc caggtgaaca ccgagggatc ttattagaca agcatttgtt    960
ccggatagtc aagcattggc tgaaggcaga tcacgatccc ttctacaacc ctgtgaatga   1020
ttatgtgatc ctaccgacta tattcgagat cgagcggcac aaggaaaagg gcttagaagt   1080
aatgtcactc aaggaagaat gggaactcgt ttccggagac caagaagatg atgacaccta   1140
cgacaataga aaaccaatgg ttggatcgat atcagcttct catgtaggag acgatggatc   1200
ttttgatgaa gtggcacgtg cgactttcat cgttcatccg cagagcaacg gcaaacaaca   1260
tattgaattg aatgccatga gtgttactgc tggtggtgca taattctggt ggttaatgaa   1320
tttatcattc tgtttatgta tatattgttc aagtgtttgt ttaaatgagt ttaaataaaa   1380
ttttaataaa aaaatatgat ggaaacaact cgwtktgtak cccggtaccc aattcgccct   1440
atagtgagtc gtattacaat tcactggccg nccgg                              1475
```

<210> SEQ ID NO 12
<211> LENGTH: 433
<212> TYPE: PRT
<213> ORGANISM: Vernonia mespilifolia
<220> FEATURE:
<221> NAME/KEY: UNSURE
<222> LOCATION: (106)
<223> OTHER INFORMATION: Xaa = any amino acid
<220> FEATURE:
<221> NAME/KEY: UNSURE
<222> LOCATION: (118)
<223> OTHER INFORMATION: Xaa = any amino acid
<220> FEATURE:
<221> NAME/KEY: UNSURE
<222> LOCATION: (135)..(136)
<223> OTHER INFORMATION: Xaa = any amino acid
<220> FEATURE:
<221> NAME/KEY: UNSURE
<222> LOCATION: (138)
<223> OTHER INFORMATION: Xaa = any amino acid
<220> FEATURE:
<221> NAME/KEY: UNSURE
<222> LOCATION: (140)
<223> OTHER INFORMATION: Xaa = any amino acid

<400> SEQUENCE: 12

```
Ile Asp Cys Leu Asp Pro Asp Met Leu Ile Gly Arg Asp Ser Val Cys
  1               5                  10                  15

Tyr Phe His Glu Met Ile Asn Glu Met Thr Ser Trp Gly Tyr Leu Glu
             20                  25                  30

Gly Lys Thr Leu Phe Gly Phe Gly Tyr Asp Phe Arg Gln Ser Asn Arg
         35                  40                  45

Leu Gln Glu Thr Met Asp Arg Leu Ala Thr Lys Leu Glu Ser Ile Tyr
     50                  55                  60
```

```
Thr Ser Ser Gly Gly Lys Lys Ile Asn Val Ile Thr His Ser Met Gly
 65                  70                  75                  80

Gly Leu Leu Val Lys Cys Phe Met Ser Leu His Ser Asp Ile Phe Glu
                 85                  90                  95

Lys Tyr Val Lys Asn Trp Ile Ala Ile Xaa Ala Pro Phe Gln Gly Ala
            100                 105                 110

Pro Gly Tyr Val Thr Xaa Thr Leu Leu Asn Gly Met Ser Phe Val Glu
        115                 120                 125

Gly Trp Glu Ala Tyr Phe Xaa Xaa Ser Xaa Trp Xaa Met His Gln Leu
130                 135                 140

Leu Ile Glu Cys Pro Ser Ile Tyr Glu Leu Met Ala Cys Leu Asp Tyr
145                 150                 155                 160

Glu Trp Glu His Asp Pro Leu Leu Gln Ile Trp Lys Glu Ile Gln Asn
                165                 170                 175

Asp Asp Gly Asn Ser Thr Thr Ile Leu Glu Thr Phe Thr Pro Val Glu
            180                 185                 190

Ala Val Ser Ile Phe Thr Gln Ala Leu Ser Ile Asn Glu Leu Asn Tyr
        195                 200                 205

Gly Gly Val Asp Ile Pro Leu Pro Phe Asn Lys Glu Ile Leu His Trp
210                 215                 220

Ala Asn Lys Thr Arg Glu Ile Leu Ser Ser Ala Lys Leu Pro Pro Asn
225                 230                 235                 240

Val Lys Phe Tyr Asn Val Tyr Gly Thr Gly Arg Asp Thr Pro Gln Ser
                245                 250                 255

Val Cys Tyr Gly Ser Ala Asp Ser Pro Val Ser Asp Leu Gln Glu Leu
            260                 265                 270

Pro Leu Leu Asp Ala Thr Phe Ile Asn Val Asp Gly Asp Gly Thr Val
        275                 280                 285

Pro Met Glu Ser Ala Lys Ala Asp Gly Leu Asp Ala Glu Ala Arg Val
290                 295                 300

Gly Ile Pro Gly Glu His Arg Gly Ile Leu Leu Asp Lys His Leu Phe
305                 310                 315                 320

Arg Ile Val Lys His Trp Leu Lys Ala Asp His Asp Pro Phe Tyr Asn
                325                 330                 335

Pro Val Asn Asp Tyr Val Ile Leu Pro Thr Ile Phe Glu Ile Glu Arg
            340                 345                 350

His Lys Glu Lys Gly Leu Glu Val Met Ser Leu Lys Glu Glu Trp Glu
        355                 360                 365

Leu Val Ser Gly Asp Gln Glu Asp Asp Thr Tyr Asp Asn Arg Lys
370                 375                 380

Pro Met Val Gly Ser Ile Ser Ala Ser His Val Gly Asp Asp Gly Ser
385                 390                 395                 400

Phe Asp Glu Val Ala Arg Ala Thr Phe Ile Val His Pro Gln Ser Asn
                405                 410                 415

Gly Lys Gln His Ile Glu Leu Asn Ala Met Ser Val Thr Ala Gly Gly
            420                 425                 430

Ala

<210> SEQ ID NO 13
<211> LENGTH: 634
<212> TYPE: DNA
<213> ORGANISM: Triticum aestivum

<400> SEQUENCE: 13
```

```
cgcctccgga atccccaccc ccgtccaaat ccgggcaaac catataccccc agctacccgc    60 cgcggagcag attccccgcc atccgccgac gccacgccac gccacccccg tgccgctccg   120
attcgagctt gccggagctc ggtttggccg gaagcctcgc cctctcatgc tgatctcgcg   180
gccgggggct tgagagtgct tatttagggc ggggatttgg gcggcgggga agcaaggatg   240
tcggtgctgg aggatttgat ccgggcgatc gagctgtggc tgcggatcgc caaggagcag   300
gtgccgctgg tcgaccccag cctcgacccg gtgctgctcg tgcccggcat cggcggctcc   360
atcctcgagg ccgtggacga ggccgggaac aaggagcggg tctgggtgcg catcctcgcc   420
gccgaccacg agtgccgcga aagctctgg gcgcagttcg atgcctccac tggcaaaact   480
atttctgtgg atgagaaaat acgcatcact gtcccggagg ataggtatgg attgtacgcc   540
atcgacacat tggacccaga cctgattatt ggtgatgaca gtgtttacta ctatcatgac   600
atgatagtgc aaatgattaa atggggatat caag                              634
```

<210> SEQ ID NO 14
<211> LENGTH: 132
<212> TYPE: PRT
<213> ORGANISM: Triticum aestivum

<400> SEQUENCE: 14

```
Met Ser Val Leu Glu Asp Leu Ile Arg Ala Ile Glu Leu Trp Leu Arg
  1               5                  10                  15

Ile Ala Lys Glu Gln Val Pro Leu Val Asp Pro Ser Leu Asp Pro Val
             20                  25                  30

Leu Leu Val Pro Gly Ile Gly Gly Ser Ile Leu Glu Ala Val Asp Glu
         35                  40                  45

Ala Gly Asn Lys Glu Arg Val Trp Val Arg Ile Leu Ala Ala Asp His
     50                  55                  60

Glu Cys Arg Glu Lys Leu Trp Ala Gln Phe Asp Ala Ser Thr Gly Lys
 65                  70                  75                  80

Thr Ile Ser Val Asp Glu Lys Ile Arg Ile Thr Val Pro Glu Asp Arg
                 85                  90                  95

Tyr Gly Leu Tyr Ala Ile Asp Thr Leu Asp Pro Asp Leu Ile Ile Gly
            100                 105                 110

Asp Asp Ser Val Tyr Tyr Tyr His Asp Met Ile Val Gln Met Ile Lys
        115                 120                 125

Trp Gly Tyr Gln
    130
```

<210> SEQ ID NO 15
<211> LENGTH: 1510
<212> TYPE: DNA
<213> ORGANISM: C. tetragonoloba

<400> SEQUENCE: 15

```
gcacgagggc atatcaaagc agtgatgaac attggggggac catttcttgg tgttccaaaa    60
tcagttgctg gacttttctc tctagaggcc agggatatcg ctgttgccag ggcattcgca   120
ccaggagttt tggataaaga tgttttttggt cttcaaactt tactgcatct aatgcggatg   180
acccgaacat gggattcaac tatgtcaatg ataccaaaag gtggggatac tatatgggt    240 ggccttgatt ggtcacctga aggacactat agctgcagtg caaagaagct caagaaaaat   300
gatacttaca attcatttca aaatgacaaa gagaatctta gttcgtgaa aagtgtgaac   360 tatgggagac tcatatcatt tgggaaacat atcgctgagt acattcttc caagcttgag   420
```

```
aggttggatt ttaggggtgc tcttaagggt aggaaccttg caaacacatc tagttgtgat    480
gtctggacag agtaccatga atgggtatt gaaggaatca agctgttct agattacaaa     540 acttacacag ctgactcagt cttggatttg cttcattatg ttgctcccaa gatgatgaag    600
cgtggagatg ctcattttc tcatgggatt gctgataatt tggatgatga aaataccaa     660 cattacaagt actggtctaa ccccttagaa acaaggttac caaatgctcc agatatggaa    720
atttactcta tgtacgggt tgggatccct acagaaagag cctatgtcta caaatttaat    780
cctcaatctg aatgccaaat ccccttcag attgacacat cagctgatgg cgaaaatgag    840
gactcatgtc taaaggatgg agtttattgt tctgatggta tgaaactgt tcctgtttta    900 agtgctggtt tcatgtgtgc aaagggttgg cggggaaaaa cccgcttcaa tccttccgga    960
attcatacat acataaggga gtatgatcat gccccctccag ctaatcttct agaaggccgg   1020
ggaacccaga gtggtgctca tgttgatata ttgggtaact ttgcattgat tgaagatatt   1080
atacgagtag cggctggagc ctccggtgaa gacctgggtg gtgatcgagt gtactctgat   1140
attttcaaat ggtctgaaaa tatcaatttg aagctctaga ttcacatgta cgagatcaaa   1200
tcccatctcc ttcaaaccat cttgccagag attgacctaa tggtatgaac tacaaagctg   1260
atgcattgtt gacagcggca acttgcttta tgctaggatt ttatctgtag gaaagaaatt   1320
acacaatatc ttagttgtag aacatgtttt cagattttgt ttattctatt catttgtttg   1380
gattattgtc aggtattagt gtcaagtgtc caatactaac tattcgtgag acctgttata   1440
gaccagttag tggaaaatag gacataattt aatagataat gcgcttcaaa ttaaaaaaaa   1500
aaaaaaaaaa                                                           1510
```

<210> SEQ ID NO 16
<211> LENGTH: 389
<212> TYPE: PRT
<213> ORGANISM: C. tetragonoloba

<400> SEQUENCE: 16

```
His Ile Lys Ala Val Met Asn Ile Gly Gly Pro Phe Leu Gly Val Pro
  1               5                  10                  15

Lys Ser Val Ala Gly Leu Phe Ser Leu Glu Ala Arg Asp Ile Ala Val
             20                  25                  30

Ala Arg Ala Phe Ala Pro Gly Val Leu Asp Lys Asp Val Phe Gly Leu
         35                  40                  45

Gln Thr Leu Leu His Leu Met Arg Met Thr Arg Thr Trp Asp Ser Thr
     50                  55                  60

Met Ser Met Ile Pro Lys Gly Asp Thr Ile Trp Gly Gly Leu Asp
 65                  70                  75                  80

Trp Ser Pro Glu Gly His Tyr Ser Cys Ser Ala Lys Lys Leu Lys Lys
             85                  90                  95

Asn Asp Thr Tyr Asn Ser Phe Gln Asn Asp Lys Glu Asn Leu Lys Phe
            100                 105                 110

Val Lys Ser Val Asn Tyr Gly Arg Leu Ile Ser Phe Gly Lys His Ile
        115                 120                 125

Ala Glu Leu His Ser Ser Lys Leu Glu Arg Leu Asp Phe Arg Gly Ala
    130                 135                 140

Leu Lys Gly Arg Asn Leu Ala Asn Thr Ser Ser Cys Asp Val Trp Thr
145                 150                 155                 160

Glu Tyr His Glu Met Gly Ile Glu Gly Ile Lys Ala Val Leu Asp Tyr
                165                 170                 175
```

```
Lys Thr Tyr Thr Ala Asp Ser Val Leu Asp Leu Leu His Tyr Val Ala
            180                 185                 190

Pro Lys Met Met Lys Arg Gly Asp Ala His Phe Ser His Gly Ile Ala
        195                 200                 205

Asp Asn Leu Asp Asp Glu Lys Tyr Gln His Tyr Lys Tyr Trp Ser Asn
    210                 215                 220

Pro Leu Glu Thr Arg Leu Pro Asn Ala Pro Asp Met Glu Ile Tyr Ser
225                 230                 235                 240

Met Tyr Gly Val Gly Ile Pro Thr Glu Arg Ala Tyr Val Tyr Lys Phe
                245                 250                 255

Asn Pro Gln Ser Glu Cys Gln Ile Pro Phe Gln Ile Asp Thr Ser Ala
            260                 265                 270

Asp Gly Glu Asn Glu Asp Ser Cys Leu Lys Asp Gly Val Tyr Cys Ser
        275                 280                 285

Asp Gly Asp Glu Thr Val Pro Val Leu Ser Ala Gly Phe Met Cys Ala
    290                 295                 300

Lys Gly Trp Arg Gly Lys Thr Arg Phe Asn Pro Ser Gly Ile His Thr
305                 310                 315                 320

Tyr Ile Arg Glu Tyr Asp His Ala Pro Pro Ala Asn Leu Leu Glu Gly
                325                 330                 335

Arg Gly Thr Gln Ser Gly Ala His Val Asp Ile Leu Gly Asn Phe Ala
            340                 345                 350

Leu Ile Glu Asp Ile Ile Arg Val Ala Ala Gly Ala Ser Gly Glu Asp
        355                 360                 365

Leu Gly Gly Asp Arg Val Tyr Ser Asp Ile Phe Lys Trp Ser Glu Asn
    370                 375                 380

Ile Asn Leu Lys Leu
385

<210> SEQ ID NO 17
<211> LENGTH: 2479
<212> TYPE: DNA
<213> ORGANISM: Parthenium argentatum Grey

<400> SEQUENCE: 17
gcaccagctc cgccggttgc atacgtcatc atcacgtaat gtcactactt cgaagaagaa      60
agcaaccaca acaccatccg gatccaacac cagacgaaga aaacgaagaa aaggaacaaa     120
aagcgtttaa aaaacaagca aaaaccaaca aaacaaaaaa ctacacgtgt ctggataact     180
gctgttggtt cgtgggatgc gtatgttcag tatggtggtt attattattt ttatacaacg     240
cgatgccagc gtcgttccct cagtttgtaa cggaggctat atccggaccg gttccggatc     300 ctccagggggt taagtgtttg aaagaagggt tgaaggcgaa gcatccggtg gtgtttgtgc     360
ccgggattgt gaccggtggg cttgagctgt gggaagggca tcagtgtatg gatgggttgt     420
ttaggaagag gctgtggggt ggtacgtttg gtgaggttta taaaggcct tcatgttggg       480 tacaacatat gtccctggac aacaaaactg ggatggatcc gccaggtata cgggtcagac     540
ccgttagtgg acttgtagct gctgactact ttgccccggg atattttgtt tgggctgttt     600
tgattgctaa cttggcgcgt gttggatatg aagagaaaaa tatgtatatg gctgcatatg     660
actggagact ctcgtttcaa aacacggagg taagagacca acattgagt cggataaaga       720 gcaatataga actgatggtt gctacaaatg gtgggaaaaa ggcggttatt atcccacatt     780
caatgggtgt tatctacttc ctgcatttca tgaaatgggt cgaagcacca gctccaatgg     840
gtggtggagg tggaccagat tggtgtgcta acatatcaa agcggtaatg aacattggtg      900
```

```
gaccattttt aggtgtccca aaagctgtag ccgggctttt ctctgcagaa gctaaagata    960
ttgcatcagt cagggctctt gcaccaggta tgttggactc ggatttattt cagattcaga   1020
cgttacaaca tataatgaga atgagccgca catgggattc aaccatgtct atgataccaa   1080
aaggcgggga caccatttgg ggcggtcttg attggtctcc cgaagacggg tatagtccaa   1140
gtaagagaaa acatggaaaa aatgacactg aatcttctac ccaaaatgag tctgcaagtg   1200
aagaatgtga agtaacacac gcaaattatg gaaggatagt atcatttggg agagatgtag   1260
cagaggcacc atcttcagag atcgagagga tagaatttag gggtgctgtg aagggtaaca   1320
atgttgcaaa caatacatgc cgggccgtgt ggaccgaata ccatgacatg ggatttggtg   1380
gaatcaaggc tgttgcagag tacaaggtat atacagctgg cgaaattgtg gatatgctgg   1440
agtttgttgc tccaaaaatg atggaacgcg gcagtgctca tttttcatat ggtatagctg   1500
acaatttgga tgacccaaaa tactcacatt acaagtattg gtctaaccca ttagagacaa   1560
agctaccaaa cgctccagac atggagatct attcaatgta tggagttggc atcccaactg   1620
aaagagcata tgtttataaa ctcacacctg cagcagaatg ctacatacca ttccaaattg   1680
acacgtcggc aaaagataaa aacgaggatg ggtgtttaaa agatggagtt tatacggttg   1740
acggagatga aacagtacca gcattaagcg caggctacat gtgtgcaaaa ggttggcgtg   1800
ggaaaactag attcaatcct tcgggaatca aaacgtatgt tagggaatac gatcacaatc   1860
ctccatccaa ctttcttgag ggccgggggca cgcaaagcgg ggctcacgtg gatattatgg   1920
gtaatttcca gttaattgaa gatgttataa aggttgcagc cggagccacg ggtgaagaac   1980
tgggaggtga tcaggtgtac acaggtatat tcgagtggtc cgagaaaatc aatttagagt   2040
tatgaaatat ttgaggtagg aattatacaa acaatatatt ggggtgcgtt tattgcataa   2100
tcagttttga ttagagaatt gcgagaacct aagtactttg taccggtgca tggaagatgt   2160
gatagcgtct tttgtatcat acttaaagca ataagtattc gggttagtgt acttctcgca   2220
gttctgtatt tgattttggc tctgtattaa acgtaactcc gtgtgcatta ttgatccaca   2280
aatctgtact gtgggtggat tatttttgtaa tttgtagcat gttgcttcct taaacagcca   2340
taaaaatttg tttgttgtat cttgatatat gtaatcattt ttaggaagga gttaacattt   2400
atatgtaaaa aaaaaaaaaa aaaaaaaaaa aaaaaaaaaa aaaaaaaaaa aaaaaaaaaa   2460
aaaaaaaaaa aaaaaaaa                                                 2479
```

<210> SEQ ID NO 18
<211> LENGTH: 668
<212> TYPE: PRT
<213> ORGANISM: Parthenium argentatum Grey

<400> SEQUENCE: 18

```
Met Ser Leu Leu Arg Arg Arg Lys Gln Pro Gln His His Pro Asp Pro
 1               5                  10                  15

Thr Pro Asp Glu Glu Asn Glu Glu Lys Glu Gln Lys Ala Phe Lys Lys
                20                  25                  30

Gln Ala Lys Thr Asn Lys Thr Lys Asn Tyr Thr Cys Leu Asp Asn Cys
            35                  40                  45

Cys Trp Phe Val Gly Cys Val Cys Ser Val Trp Trp Leu Leu Leu Phe
        50                  55                  60

Leu Tyr Asn Ala Met Pro Ala Ser Phe Pro Gln Phe Val Thr Glu Ala
    65                  70                  75                  80

Ile Ser Gly Pro Val Pro Asp Pro Pro Gly Val Lys Cys Leu Lys Glu
```

-continued

```
                    85                   90                   95
Gly Leu Lys Ala Lys His Pro Val Val Phe Val Pro Gly Ile Val Thr
                100                 105                 110
Gly Gly Leu Glu Leu Trp Glu Gly His Gln Cys Met Asp Gly Leu Phe
                115                 120                 125
Arg Lys Arg Leu Trp Gly Gly Thr Phe Gly Glu Val Tyr Lys Arg Pro
                130                 135                 140
Ser Cys Trp Val Gln His Met Ser Leu Asp Asn Lys Thr Gly Met Asp
145                 150                 155                 160
Pro Pro Gly Ile Arg Val Arg Pro Val Ser Gly Leu Val Ala Ala Asp
                165                 170                 175
Tyr Phe Ala Pro Gly Tyr Phe Val Trp Ala Val Leu Ile Ala Asn Leu
                180                 185                 190
Ala Arg Val Gly Tyr Glu Glu Lys Asn Met Tyr Met Ala Ala Tyr Asp
                195                 200                 205
Trp Arg Leu Ser Phe Gln Asn Thr Glu Val Arg Asp Gln Thr Leu Ser
                210                 215                 220
Arg Ile Lys Ser Asn Ile Glu Leu Met Val Ala Thr Asn Gly Gly Lys
225                 230                 235                 240
Lys Ala Val Ile Ile Pro His Ser Met Gly Val Ile Tyr Phe Leu His
                245                 250                 255
Phe Met Lys Trp Val Glu Ala Pro Ala Pro Met Gly Gly Gly Gly Gly
                260                 265                 270
Pro Asp Trp Cys Ala Lys His Ile Lys Ala Val Met Asn Ile Gly Gly
                275                 280                 285
Pro Phe Leu Gly Val Pro Lys Ala Val Ala Gly Leu Phe Ser Ala Glu
                290                 295                 300
Ala Lys Asp Ile Ala Ser Val Arg Ala Leu Ala Pro Gly Met Leu Asp
305                 310                 315                 320
Ser Asp Leu Phe Gln Ile Gln Thr Leu Gln His Ile Met Arg Met Ser
                325                 330                 335
Arg Thr Trp Asp Ser Thr Met Ser Met Ile Pro Lys Gly Gly Asp Thr
                340                 345                 350
Ile Trp Gly Gly Leu Asp Trp Ser Pro Glu Asp Gly Tyr Ser Pro Ser
                355                 360                 365
Lys Arg Lys His Gly Lys Asn Asp Thr Glu Ser Ser Thr Gln Asn Glu
                370                 375                 380
Ser Ala Ser Glu Glu Cys Glu Val Thr His Ala Asn Tyr Gly Arg Ile
385                 390                 395                 400
Val Ser Phe Gly Arg Asp Val Ala Glu Ala Pro Ser Ser Glu Ile Glu
                405                 410                 415
Arg Ile Glu Phe Arg Gly Ala Val Lys Gly Asn Asn Val Ala Asn Asn
                420                 425                 430
Thr Cys Arg Ala Val Trp Thr Glu Tyr His Asp Met Gly Phe Gly Gly
                435                 440                 445
Ile Lys Ala Val Ala Glu Tyr Lys Val Tyr Thr Ala Gly Glu Ile Val
                450                 455                 460
Asp Met Leu Glu Phe Val Ala Pro Lys Met Met Glu Arg Gly Ser Ala
465                 470                 475                 480
His Phe Ser Tyr Gly Ile Ala Asp Asn Leu Asp Asp Pro Lys Tyr Ser
                485                 490                 495
His Tyr Lys Tyr Trp Ser Asn Pro Leu Glu Thr Lys Leu Pro Asn Ala
                500                 505                 510
```

```
Pro Asp Met Glu Ile Tyr Ser Met Tyr Gly Val Gly Ile Pro Thr Glu
        515                 520                 525

Arg Ala Tyr Val Tyr Lys Leu Thr Pro Ala Ala Glu Cys Tyr Ile Pro
    530                 535                 540

Phe Gln Ile Asp Thr Ser Ala Lys Asp Lys Asn Glu Asp Gly Cys Leu
545                 550                 555                 560

Lys Asp Gly Val Tyr Thr Val Asp Gly Asp Glu Thr Val Pro Ala Leu
                565                 570                 575

Ser Ala Gly Tyr Met Cys Ala Lys Gly Trp Arg Gly Lys Thr Arg Phe
            580                 585                 590

Asn Pro Ser Gly Ile Lys Thr Tyr Val Arg Glu Tyr Asp His Asn Pro
        595                 600                 605

Pro Ser Asn Phe Leu Glu Gly Arg Gly Thr Gln Ser Gly Ala His Val
    610                 615                 620

Asp Ile Met Gly Asn Phe Gln Leu Ile Glu Asp Val Ile Lys Val Ala
625                 630                 635                 640

Ala Gly Ala Thr Gly Glu Glu Leu Gly Gly Asp Gln Val Tyr Thr Gly
                645                 650                 655

Ile Phe Glu Trp Ser Glu Lys Ile Asn Leu Glu Leu
        660                 665

<210> SEQ ID NO 19
<211> LENGTH: 2565
<212> TYPE: DNA
<213> ORGANISM: Zea mays

<400> SEQUENCE: 19
cgcgacctca caagcgcgaa ccccacgaag ccggagccaa gccacgacgg gtcgaccggt      60
cgacggcccc tcgacctgcc cgcctcgctt cctccgacgc ctagggtttt ctaccggacg     120
ccgccgccgc cgcagcagcg gcccgggatg caggtgtgcc cgcgcagtta gccgccgtcg     180
gacccaccgc cgccgcgcgc catgtcattc ttgcggcggc gaaagccgct gccgccctct     240
gacggtgacg agtccgacca cgacgacaac gacaagggga agaagccgtc ctcatcctcc     300
gggtcgccgt ccaaggagcc cacgaagcgg accaaggcca gtggtcgtg cgtggacagc      360 tgctgctggc tggtcgggtg cgtgtgctcc gcctggtggt tgctgctctt tctctacaac     420
gcgatgccag cttcgttccc gcagtatgta acggaggcca tcacgggtcc gctcccggac     480
ccgcccgggg tcaagctgca gaaggagggg ctgcgagcta agcacccgt cgtctttgtc      540 cccggcatcg tcaccggggg cctcgagcta tgggagggac accaatgcgc cgagggtctc     600
ttccgcaagc ggctatgggg cggcacattt ggtgacgtat acaagagacc tctatgctgg     660
gttgaacata tgtcgttgga caatgaaact ggattagaca aacctggaat aagggtcagg    720
tcagtcacag gccttgttgc agcagactat ttcgtccccg atattttgt ttgggctgtc     780 ttaattgcca atttagctcg tattggatat gaagaaaaga ccatgtacat ggctgcatat    840
gattggaggt tatctttcca gaacactgag gttcgtgatc aaactttgag cagaataaag    900
agcaatattg aactcatggt agcaacaaat ggtgaaaata gggtggtggt gatcccacac    960
tccatggggg tcctctattt tctgcatttt atgaaatggg tcgaagcacc tcctcccatg   1020
gggggcggtg gtggtccgaa ctggtgtgag aagcatatta agctgtaat gaatattgga    1080 ggacctttct taggagttcc caaggctgtt gctgggcttt tctcatctga agccaaagat   1140
gttgccgttg ctagagctat cgctcctgat gtcctggact ctgattttct tggacttcaa   1200
```

-continued

```
actttgcgcc atttgatgcg tatgacccga acatgggatt caacaatgtc aatgcttcct    1260
aaaggtggtg atacaatttg gggaaatctg gattggtctc cagaagatgg ccttgaatgt    1320
aaagctaaga agcataaaac caatgatacc gaggtttcta aggatagcaa tggggaaaat    1380
atcgaagttc aacctgaacc tataaactac ggaaggctgg tatccttcgg taaagatgta    1440
gcagaggcac cttcttcaga gattgaacag atagaatttc gtgatgctgt taaaggtaac    1500
gatatcgtcc attcaaatgc atcatgccgg agatctggga cagagtacca tgaattagga    1560
tggggtggaa taaaggcagt cgcagactac aaagtttaca ctgccagttc tgttatagac    1620
cttcttcact tgttgctcc aaggatgatg cagcgtggca atgtccactt ttcatatgga     1680
attgctgata acttggatga tccgaaatat caacattaca aatattggtc aaacccttg     1740 gaaacaaagc taccgaatgc tcctgacatg gaaataattt ccatgtacgg agtaggcatt    1800
cctactgaaa gggcatatgt ctacaagttg gctccacagg cagagtgcta tataccattc    1860
cggattgacg cctcggctga tggcggggag gaaaacaaat gcttgaaagg gggtgtttac    1920
ttagctgacg gcgacgaaac tgttccagtt cttagcgcgg gctacatgtg tgcaaaaggg    1980
tggcgtggca aaactcgttt caaccctgcc ggcagcaaga cttacgtgag agagtacagc    2040
cattcaccac cctcaactct cctggaaggc agggggcactc agagcggtgc acatgttgat    2100
ataatgggga acttcgcttt gatcgaggac atcatcagga tagctgccgg ggcaaccggt    2160
gaggaaattg gtggcgacca ggtttattca gatatattca aatggtcaga gaaaatcaaa    2220
ttgaaattgt aacccatggg aagttaaaag aagtgcccca acccgttcat tgcgttccta    2280
aatgcttgcc tgagcgcaac tctggatttt gcttaaatat cgtattttt tcacgcctca     2340 ttcgtccctc tagtaaattt acattgacag gaccccggtg cgacgcggat gttgtaccgt    2400 attttttggca ttgtatatta aaatgtacag gcgtaagtta catttgctag ctgaaattat    2460
tgcagtagct tgccttttct tttgagcacg gaaaaaaaaa aaaaaaaaaa aaaaaaaaa     2520 aaaaaaaaaa aaaaaaaaaa aaaaaaaaa aaaaaaaaa aaaaa                      2565
```

<210> SEQ ID NO 20
<211> LENGTH: 676
<212> TYPE: PRT
<213> ORGANISM: Zea mays

<400> SEQUENCE: 20

```
Met Ser Phe Leu Arg Arg Arg Lys Pro Leu Pro Ser Asp Gly Asp
 1               5                  10                  15

Glu Ser Asp His Asp Asp Asn Asp Lys Gly Lys Lys Pro Ser Ser
                20                  25                  30

Ser Gly Ser Pro Ser Lys Glu Pro Thr Lys Arg Thr Lys Ala Lys Trp
            35                  40                  45

Ser Cys Val Asp Ser Cys Cys Trp Leu Val Gly Cys Val Cys Ser Ala
        50                  55                  60

Trp Trp Leu Leu Leu Phe Leu Tyr Asn Ala Met Pro Ala Ser Phe Pro
65                  70                  75                  80

Gln Tyr Val Thr Glu Ala Ile Thr Gly Pro Leu Pro Asp Pro Pro Gly
                85                  90                  95

Val Lys Leu Gln Lys Glu Gly Leu Arg Ala Lys His Pro Val Phe
            100                 105                 110

Val Pro Gly Ile Val Thr Gly Gly Leu Glu Leu Trp Glu Gly His Gln
        115                 120                 125

Cys Ala Glu Gly Leu Phe Arg Lys Arg Leu Trp Gly Gly Thr Phe Gly
```

-continued

```
            130                 135                 140
Asp Val Tyr Lys Arg Pro Leu Cys Trp Val Glu His Met Ser Leu Asp
145                 150                 155                 160
Asn Glu Thr Gly Leu Asp Lys Pro Gly Ile Arg Val Arg Ser Val Thr
                165                 170                 175
Gly Leu Val Ala Ala Asp Tyr Phe Val Pro Gly Tyr Phe Val Trp Ala
                180                 185                 190
Val Leu Ile Ala Asn Leu Ala Arg Ile Gly Tyr Glu Glu Lys Thr Met
            195                 200                 205
Tyr Met Ala Ala Tyr Asp Trp Arg Leu Ser Phe Gln Asn Thr Glu Val
        210                 215                 220
Arg Asp Gln Thr Leu Ser Arg Ile Lys Ser Asn Ile Glu Leu Met Val
225                 230                 235                 240
Ala Thr Asn Gly Gly Asn Arg Val Val Ile Pro His Ser Met Gly
                245                 250                 255
Val Leu Tyr Phe Leu His Phe Met Lys Trp Val Glu Ala Pro Pro
                260                 265                 270
Met Gly Gly Gly Gly Pro Asn Trp Cys Glu Lys His Ile Lys Ala
            275                 280                 285
Val Met Asn Ile Gly Gly Pro Phe Leu Gly Val Pro Lys Ala Val Ala
        290                 295                 300
Gly Leu Phe Ser Ser Glu Ala Lys Asp Val Ala Val Ala Arg Ala Ile
305                 310                 315                 320
Ala Pro Asp Val Leu Asp Ser Asp Phe Leu Gly Leu Gln Thr Leu Arg
                325                 330                 335
His Leu Met Arg Met Thr Arg Thr Trp Asp Ser Thr Met Ser Met Leu
                340                 345                 350
Pro Lys Gly Gly Asp Thr Ile Trp Gly Asn Leu Asp Trp Ser Pro Glu
            355                 360                 365
Asp Gly Leu Glu Cys Lys Ala Lys Lys His Lys Thr Asn Asp Thr Glu
        370                 375                 380
Val Ser Lys Asp Ser Asn Gly Glu Asn Ile Glu Val Gln Pro Glu Pro
385                 390                 395                 400
Ile Asn Tyr Gly Arg Leu Val Ser Phe Gly Lys Asp Val Ala Glu Ala
                405                 410                 415
Pro Ser Ser Glu Ile Glu Gln Ile Glu Phe Arg Asp Ala Val Lys Gly
                420                 425                 430
Asn Asp Ile Val His Ser Asn Ala Ser Cys Arg Glu Ile Trp Thr Glu
            435                 440                 445
Tyr His Glu Leu Gly Trp Gly Gly Ile Lys Ala Val Ala Asp Tyr Lys
        450                 455                 460
Val Tyr Thr Ala Ser Ser Val Ile Asp Leu Leu His Phe Val Ala Pro
465                 470                 475                 480
Arg Met Met Gln Arg Gly Asn Val His Phe Ser Tyr Gly Ile Ala Asp
                485                 490                 495
Asn Leu Asp Asp Pro Lys Tyr Gln His Tyr Lys Tyr Trp Ser Asn Pro
                500                 505                 510
Leu Glu Thr Lys Leu Pro Asn Ala Pro Asp Met Glu Ile Ile Ser Met
            515                 520                 525
Tyr Gly Val Gly Ile Pro Thr Glu Arg Ala Tyr Val Tyr Lys Leu Ala
        530                 535                 540
Pro Gln Ala Glu Cys Tyr Ile Pro Phe Arg Ile Asp Ala Ser Ala Asp
545                 550                 555                 560
```

Gly Gly Glu Glu Asn Lys Cys Leu Lys Gly Gly Val Tyr Leu Ala Asp
            565                 570                 575

Gly Asp Glu Thr Val Pro Val Leu Ser Ala Gly Tyr Met Cys Ala Lys
            580                 585                 590

Gly Trp Arg Gly Lys Thr Arg Phe Asn Pro Ala Gly Ser Lys Thr Tyr
            595                 600                 605

Val Arg Glu Tyr Ser His Ser Pro Pro Ser Thr Leu Leu Glu Gly Arg
        610                 615                 620

Gly Thr Gln Ser Gly Ala His Val Asp Ile Met Gly Asn Phe Ala Leu
625                 630                 635                 640

Ile Glu Asp Ile Ile Arg Ile Ala Ala Gly Ala Thr Gly Glu Glu Ile
                645                 650                 655

Gly Gly Asp Gln Val Tyr Ser Asp Ile Phe Lys Trp Ser Glu Lys Ile
            660                 665                 670

Lys Leu Lys Leu
        675

<210> SEQ ID NO 21
<211> LENGTH: 2433
<212> TYPE: DNA
<213> ORGANISM: Oryza sativa

<400> SEQUENCE: 21

| | |
|---|---|
| ttcggcacga ggtttaaacc aagcgcgaac cccgcggagc cgccacctct ctcgcctccc | 60 |
| cgcctccgcc gcgccgccta gggtttccac cgccccgggg atgcgcgcgc ccctcgccg | 120 |
| gtagcctccc ccccggttcc cgccgcctcc gccgccgcca tgtcgctgct gcggcgccgg | 180 |
| aagcagccgc agccgccgcc ggagcagccg aacgaggaca gcagcaacgg ctccgacctc | 240 |
| gacgagaagg ggaagaagaa gccgggatcg tcgtcctcct cggcggcgcc tcctccggag | 300 |
| gcggcggcgc cggcggcgaa ggaggcgacg aagcggacga gggccaggtg gtcgtgcgtg | 360 |
| gacagctgct gctggctggt ggggtgcgtg tgctcggcgt ggtggctgct gctcttcctg | 420 |
| tacaacgcga tgccggcgtc gttcccgcag tacgtcacgg aggcgatcac ggggccgctc | 480 |
| ccggaccctc ccggggtcaa gctgcagaag gaggggctgc gggcgaagca ccccgtcgtg | 540 |
| ttcgtcccgg gcatcgtcac cggcggcctc gagtctgggg aggggcacca gtgcgccgag | 600 |
| gggctcttcc gcaagcgcct ctggggcggc acgttcggcg acgtgtacaa gaggcctta | 660 |
| tgctggggttg aacatatgtc actggacaat gaaactggat tagataaacc aggaataaga | 720 |
| gttcggccag tcacaggcct agtggcagca gactattttg ttcctgggta ttttgtttgg | 780 |
| gctgttttga ttgcaaattt agctcgtatt ggatatgaag aaaagaccat gtacatggct | 840 |
| gcatatgatt ggaggttatc tttccagaac actgaggttc gtgatcaaac tttgagcagg | 900 |
| ataaaaagta acattgaact cctggtagca actaatggtg gaaatagggt ggtggtgatc | 960 |
| ccacattcta tggggttct ctattttctg cattttatga agtgggttga ggctcctcct | 1020 |
| cccatgggtg gtggtggtgg tccaaattgg tgtgcaaagc acatcaaatc tgtaatgaat | 1080 |
| attggcggac ctttcttagg agttcctaag gctgttgcag gacttttctc atctgaagcc | 1140 |
| aaagatgttg ctgttgctag agccattgca ccagaagtcc tagactctga cttccttgga | 1200 |
| cttcagacct tacgccattt gatgcgtatg acccgcacat gggattcaac aatgtcaatg | 1260 |
| attcctaagg gcggtgacac catttgggga gatttggatt ggtctccaga agatggttt | 1320 |
| gagtgtaaag ctaagaatca gaaaatcaat gattctgagg tttctaagga tgctaacggg | 1380 |

-continued

```
aagaatgagg ttcatccaga acctgttaag tatggaagaa ttgtctcttt cggtaaagat      1440
gtagcagagg ctccatcttc agaaattgag cagatagaat tcgtgatgc tgtcaaaggc       1500 aataatattg cccactcaaa tacatcatgc cgggatatat ggacagagta tcacgaatta      1560
ggatggggcg gaataaaggc agttgcagac tacaaggttt acactgctgg ctccattata      1620
gatcttcttc gttttgttgc tccaaggatg atgcagcgtg gaagtgttca cttttcgtat      1680
gggattgctg acaacttgga tgatccaaag tacggccact acaaatactg gtcaaatccc      1740
ttggaaacaa aattaccaaa tgcacctgaa atggaaatat tttcaatgta tggagttggc      1800
attccgacgg agagagcata tgtctataaa ttagccccac aagcagagtg ctatatacct      1860
tttcagatag acgcttcagc tgagggtggg gatgagaata gctgtctgaa aggcggcgtt      1920
tacctgtcta atggtgatga gaccgtacca gttcttagtg caggatatat gtgcgcaaaa      1980
ggctggcgag gaaaaacacg cttcaaccct tctggcagca agacctacgt cagagaatac      2040
agccattctc caccctcaaa tctcctcgaa ggcaggggca cccagagtgg tgcgcacgtt      2100
gatatcatgg ggaattttgc tttaatcgag gatattatca ggattgctgc tggggcaact      2160
ggtgaagagc ttggcggtga ccaggtttat tccgatatat tcaaatggtc tgataagatt      2220
aaattgaaac tataaaactt taaaaaagca tggtagtttt gtaggagaat tatttgtttc      2280
ctggccaaaa ttttatgagt tttgattcga tattgtaata tgattttttt tacctttccc      2340
ttaagctctt aattcagtag aggctgactt gatttgtatt attttgtgat ttgagcggca      2400
ttgtatatta aaaaaaaaa aaaaaaaaaa aaa                                    2433
```

<210> SEQ ID NO 22
<211> LENGTH: 691
<212> TYPE: PRT
<213> ORGANISM: Oryza sativa

<400> SEQUENCE: 22

```
Met Ser Leu Leu Arg Arg Arg Lys Gln Pro Gln Pro Pro Glu Gln
  1               5                  10                  15

Pro Asn Glu Asp Ser Ser Asn Gly Ser Asp Leu Asp Glu Lys Gly Lys
                 20                  25                  30

Lys Lys Pro Gly Ser Ser Ser Ser Ala Ala Pro Pro Glu Ala
             35                  40                  45

Ala Ala Ala Ala Ala Lys Glu Ala Thr Lys Arg Thr Arg Ala Arg Trp
         50                  55                  60

Ser Cys Val Asp Ser Cys Cys Trp Leu Val Gly Cys Val Cys Ser Ala
 65                  70                  75                  80

Trp Trp Leu Leu Leu Phe Leu Tyr Asn Ala Met Pro Ala Ser Phe Pro
                 85                  90                  95

Gln Tyr Val Thr Glu Ala Ile Thr Gly Pro Leu Pro Asp Pro Pro Gly
                100                 105                 110

Val Lys Leu Gln Lys Glu Gly Leu Arg Ala Lys His Pro Val Val Phe
            115                 120                 125

Val Pro Gly Ile Val Thr Gly Gly Leu Glu Leu Trp Glu Gly His Gln
        130                 135                 140

Cys Ala Glu Gly Leu Phe Arg Lys Arg Leu Trp Gly Gly Thr Phe Gly
145                 150                 155                 160

Asp Val Tyr Lys Arg Pro Leu Cys Trp Val Glu His Met Ser Leu Asp
                165                 170                 175

Asn Glu Thr Gly Leu Asp Lys Pro Gly Ile Arg Val Arg Pro Val Thr
            180                 185                 190
```

```
Gly Leu Val Ala Ala Asp Tyr Phe Pro Gly Tyr Phe Val Trp Ala
        195                 200                 205
Val Leu Ile Ala Asn Leu Ala Arg Ile Gly Tyr Glu Glu Lys Thr Met
        210                 215                 220
Tyr Met Ala Ala Tyr Asp Trp Arg Leu Ser Phe Gln Asn Thr Glu Val
225                 230                 235                 240
Arg Asp Gln Thr Leu Ser Arg Ile Lys Ser Asn Ile Glu Leu Leu Val
                245                 250                 255
Ala Thr Asn Gly Gly Asn Arg Val Val Ile Pro His Ser Met Gly
        260                 265                 270
Val Leu Tyr Phe Leu His Phe Met Lys Trp Val Glu Ala Pro Pro
        275                 280                 285
Met Gly Gly Gly Gly Pro Asn Trp Cys Ala Lys His Ile Lys Ser
        290                 295                 300
Val Met Asn Ile Gly Gly Pro Phe Leu Gly Val Pro Lys Ala Val Ala
305                 310                 315                 320
Gly Leu Phe Ser Ser Glu Ala Lys Asp Val Ala Val Ala Arg Ala Ile
                325                 330                 335
Ala Pro Glu Val Leu Asp Ser Asp Phe Leu Gly Leu Gln Thr Leu Arg
                340                 345                 350
His Leu Met Arg Met Thr Arg Thr Trp Asp Ser Thr Met Ser Met Ile
                355                 360                 365
Pro Lys Gly Gly Asp Thr Ile Trp Gly Asp Leu Asp Trp Ser Pro Glu
        370                 375                 380
Asp Gly Phe Glu Cys Lys Ala Lys Asn Gln Lys Ile Asn Asp Ser Glu
385                 390                 395                 400
Val Ser Lys Asp Ala Asn Gly Lys Asn Glu Val His Pro Glu Pro Val
                405                 410                 415
Lys Tyr Gly Arg Ile Val Ser Phe Gly Lys Asp Val Ala Glu Ala Pro
                420                 425                 430
Ser Ser Glu Ile Glu Gln Ile Glu Phe Arg Asp Ala Val Lys Gly Asn
        435                 440                 445
Asn Ile Ala His Ser Asn Thr Ser Cys Arg Asp Ile Trp Thr Glu Tyr
        450                 455                 460
His Glu Leu Gly Trp Gly Gly Ile Lys Ala Val Ala Asp Tyr Lys Val
465                 470                 475                 480
Tyr Thr Ala Gly Ser Ile Ile Asp Leu Leu Arg Phe Val Ala Pro Arg
                485                 490                 495
Met Met Gln Arg Gly Ser Val His Phe Ser Tyr Gly Ile Ala Asp Asn
                500                 505                 510
Leu Asp Asp Pro Lys Tyr Gly His Tyr Lys Tyr Trp Ser Asn Pro Leu
        515                 520                 525
Glu Thr Lys Leu Pro Asn Ala Pro Glu Met Gly Ile Phe Ser Met Tyr
        530                 535                 540
Gly Val Gly Ile Pro Thr Glu Arg Ala Tyr Val Tyr Lys Leu Ala Pro
545                 550                 555                 560
Gln Ala Glu Cys Tyr Ile Pro Phe Gln Ile Asp Ala Ser Ala Glu Gly
                565                 570                 575
Gly Asp Glu Asn Ser Cys Leu Lys Gly Gly Val Tyr Leu Ser Asn Gly
                580                 585                 590
Asp Glu Thr Val Pro Val Leu Ser Ala Gly Tyr Met Cys Ala Lys Gly
        595                 600                 605
```

-continued

```
Trp Arg Gly Lys Thr Arg Phe Asn Pro Ser Gly Ser Lys Thr Tyr Val
    610                 615                 620

Arg Glu Tyr Ser His Ser Pro Pro Ser Asn Leu Leu Glu Gly Arg Gly
625                 630                 635                 640

Thr Gln Ser Gly Ala His Val Asp Ile Met Gly Asn Phe Ala Leu Ile
                645                 650                 655

Glu Asp Ile Ile Arg Ile Ala Ala Gly Ala Thr Gly Glu Glu Leu Gly
            660                 665                 670

Gly Asp Gln Val Tyr Ser Asp Ile Phe Lys Trp Ser Asp Lys Ile Lys
        675                 680                 685

Leu Lys Leu
    690

<210> SEQ ID NO 23
<211> LENGTH: 2700
<212> TYPE: DNA
<213> ORGANISM: Glycine max

<400> SEQUENCE: 23
gccgcacctt ccaaaattgt tgataagttt ctccttgttt ctcgaaaaaa tcagaggaaa      60
gagattccgg atcagtttcc gttcagtggt tcacagatgc tataaccaat agtcatcatc     120
ttcagaaaaa aaccaccttt tttttgccat tctgagctca ccgagctacc caatgcgatt     180
ttgattcgcg ggcttttcat ttctgtataa atctgcaatc tttgaggaaa ataacgtaac     240
cccatctgtt tataatcata tggggcacaa gtgaacggaa actctcgagg aaattgaggt     300 tgaagcttg taacgcatcc tagaatatta tgtctttgct tcgacggaga aaagggtcgg      360
aaccggaaaa gggtccgagc cgagttcgg agccaaaggt tttaagcgaa gacgagacag      420
aagatgataa gaataataag aagaataaga agaagagaga tgaggtgggg gagaagaaga     480
agaacaaatg gtcatgcttc gatagctgtt gttggtgggt ggggtgcatt tgcacattgt     540
ggtggtttct tctgtttctg tatcagatga tgccttcttc gattcctcag tatgtgaccg     600
aggccttcac tgggcccatg ccggacccac cgggcctcaa actcaaaaag gaaggactca     660
aggtgaagca ccctgtggtt tttgtgcccg ggattgtcac tgggggcctt gaactgtggg     720
agggtcacct gtgtgctgag gggttgttca ggaaacgctt gtggggtggt acttttggag     780
aagtctataa aagaccttca tgctgggtgg atcacatgtc actggacaat gaaacaggat     840
tggatccacc aggcataaga gttaggcctg tctctggact tgtagctgct gattactttg     900
ctgcaggata cttcgtttgg gcagtcctaa ttgctaactt ggcacgcatt ggttatgaag     960
aaaaaactat gtacatggct gcatatgatt ggagaatagc atttcagaac actgaggtga    1020
gggatcaaac actaagtcgg ataaaaagca acatagaact tatggttgct actaatggtg    1080
gaaataaggc agttattatt ccacattcaa tgggggtctt gtacttccta cattttatga    1140
aatgggttga agcaccagct ccaatgggtg gtggggagg accagattgg tgctccaaat    1200
atataaaggc agttgtaaac attggtggac catttttagg tgttcccaag gctatagcag    1260
ggctattctc agctgaggcc agggatattg ctgttgccag gacgatagct ccaggatttt    1320
tagataacga tctgtttcgc attcaaacct tgcaacatgt aatgaagatg acccgtactt    1380
gggactcaac aatgtcaatg ataccaagag gaggagatac tatatggggt ggtcttgatt    1440
ggtcaccaga agaaggctat cacctagcc agaggaagca tagcagtgac tatactcagt     1500
taacagacca agagacaaat caaacaaatg ttgtcaacta tggaagaatg atatcatttg    1560
gcagagatgt ggccgaggca cactcctcta agattgagat ggctgacttt cggggtgcca    1620
```

-continued

```
tcaagggtcg cagtgttgca ataccacct gtcgtgatgt gtggactgaa taccatgaaa     1680
tgggatttga gggagtgaga gcagttgctg aacataaagt ttacacagct ggctctatcg     1740
tagaactcct tcaatttgtt gctccaaaga tgatggctcg tggtagtgct catttctctt     1800
atgaaattgc tgacaatttg gatgaccota aatataatca ctacaagtat tggtcaaacc     1860
ctttggaaac aaaactacca aatgctcctg atatggaaat cttctctatg tatggagttg     1920
gcttaccaac tgaaagatct tatatttaca agttaactcc ctttgccgag tgttacattc     1980
cttttgaaat tgcaccacg caagatggtg gaagtgatga agatagttgt ctgcaaggtg     2040
gagtctacac tgttgatggg gatgagactg tgccagttct aagttcaggc tacatgtgtg     2100
ctaaaggctg gcgcggaaaa acaagattca acccgtctgg tatgcgcacc tacgttagag     2160
aatatgatca ttctcctcca gccaaccttc tagagggaag gggcacacaa agtggtgctc     2220
atgttgacat catgggaaac tttgcattga ttgaggatgt tataagagtg gctgctggag     2280
ccaaaggaga agatctagga ggtgataaag tgtattctga tatcttcaag tggtctgaga     2340
aaatcaagtt accoctatga atgaagcaca atgtaattcc gcagtccac tcagacacac     2400 ttctcttgaa cccctttaag gatcagatca gactatatat aattttttgc agtatatttt     2460
cactgccacc agagttctat gagttgctgg ttctgctgat caaagtccag ttccatggag     2520
gggtgaacta cgcgaattgg ttatattgga agagcttgca ttgaacattt ttgttattaa     2580
agtaaggatt ttatttgtca tctctaagaa acctgaccgg gggcattatt cttaataagt     2640
tcagctgatt agttatgata aaaaaaaaaa aaaaaaaaa aaaaaaaaaa aaaaaaaaa      2700
```

<210> SEQ ID NO 24
<211> LENGTH: 676
<212> TYPE: PRT
<213> ORGANISM: Glycine max

<400> SEQUENCE: 24

```
Met Ser Leu Leu Arg Arg Lys Gly Ser Glu Pro Glu Lys Gly Pro
  1               5                  10                  15

Ser Pro Ser Ser Glu Pro Lys Val Leu Ser Glu Asp Glu Thr Glu Asp
             20                  25                  30

Asp Lys Asn Asn Lys Lys Asn Lys Lys Arg Asp Glu Val Gly Glu
         35                  40                  45

Lys Lys Lys Asn Lys Trp Ser Cys Phe Asp Ser Cys Cys Trp Trp Val
     50                  55                  60

Gly Cys Ile Cys Thr Leu Trp Trp Phe Leu Leu Phe Leu Tyr Gln Met
 65                  70                  75                  80

Met Pro Ser Ser Ile Pro Gln Tyr Val Thr Glu Ala Phe Thr Gly Pro
                 85                  90                  95

Met Pro Asp Pro Pro Gly Leu Lys Leu Lys Lys Glu Gly Leu Lys Val
             100                 105                 110

Lys His Pro Val Val Phe Val Pro Gly Ile Val Thr Gly Gly Leu Glu
         115                 120                 125

Leu Trp Glu Gly His Leu Cys Ala Glu Gly Leu Phe Arg Lys Arg Leu
     130                 135                 140

Trp Gly Gly Thr Phe Gly Glu Val Tyr Lys Arg Pro Ser Cys Trp Val
145                 150                 155                 160

Asp His Met Ser Leu Asp Asn Glu Thr Gly Leu Asp Pro Pro Gly Ile
                 165                 170                 175

Arg Val Arg Pro Val Ser Gly Leu Val Ala Ala Asp Tyr Phe Ala Ala
```

-continued

```
                180                 185                 190
Gly Tyr Phe Val Trp Ala Val Leu Ile Ala Asn Leu Ala Arg Ile Gly
            195                 200                 205
Tyr Glu Glu Lys Thr Met Tyr Met Ala Ala Tyr Asp Trp Arg Ile Ala
        210                 215                 220
Phe Gln Asn Thr Glu Val Arg Asp Gln Thr Leu Ser Arg Ile Lys Ser
225                 230                 235                 240
Asn Ile Glu Leu Met Val Ala Thr Asn Gly Asn Lys Ala Val Ile
                245                 250                 255
Ile Pro His Ser Met Gly Val Leu Tyr Phe Leu His Phe Met Lys Trp
            260                 265                 270
Val Glu Ala Pro Ala Pro Met Gly Gly Gly Gly Pro Asp Trp Cys
        275                 280                 285
Ser Lys Tyr Ile Lys Ala Val Asn Ile Gly Gly Pro Phe Leu Gly
        290                 295                 300
Val Pro Lys Ala Ile Ala Gly Leu Phe Ser Ala Glu Ala Arg Asp Ile
305                 310                 315                 320
Ala Val Ala Arg Thr Ile Ala Pro Gly Phe Leu Asp Asn Asp Leu Phe
                325                 330                 335
Arg Ile Gln Thr Leu Gln His Val Met Lys Met Thr Arg Thr Trp Asp
            340                 345                 350
Ser Thr Met Ser Met Ile Pro Arg Gly Gly Asp Thr Ile Trp Gly Gly
        355                 360                 365
Leu Asp Trp Ser Pro Glu Glu Gly Tyr His Pro Ser Gln Arg Lys His
        370                 375                 380
Ser Ser Asp Tyr Thr Gln Leu Thr Asp Gln Glu Thr Asn Gln Thr Asn
385                 390                 395                 400
Val Val Asn Tyr Gly Arg Met Ile Ser Phe Gly Arg Asp Val Ala Glu
                405                 410                 415
Ala His Ser Ser Lys Ile Glu Met Ala Asp Phe Arg Gly Ala Ile Lys
            420                 425                 430
Gly Arg Ser Val Ala Asn Thr Thr Cys Arg Asp Val Trp Thr Glu Tyr
        435                 440                 445
His Glu Met Gly Phe Glu Gly Val Arg Ala Val Ala Glu His Lys Val
        450                 455                 460
Tyr Thr Ala Gly Ser Ile Val Glu Leu Leu Gln Phe Val Ala Pro Lys
465                 470                 475                 480
Met Met Ala Arg Gly Ser Ala His Phe Ser Tyr Glu Ile Ala Asp Asn
                485                 490                 495
Leu Asp Asp Pro Lys Tyr Asn His Tyr Lys Tyr Trp Ser Asn Pro Leu
            500                 505                 510
Glu Thr Lys Leu Pro Asn Ala Pro Asp Met Glu Ile Phe Ser Met Tyr
        515                 520                 525
Gly Val Gly Leu Pro Thr Glu Arg Ser Tyr Ile Tyr Lys Leu Thr Pro
        530                 535                 540
Phe Ala Glu Cys Tyr Ile Pro Phe Glu Ile Asp Thr Thr Gln Asp Gly
545                 550                 555                 560
Gly Ser Asp Glu Asp Ser Cys Leu Gln Gly Gly Val Tyr Thr Val Asp
                565                 570                 575
Gly Asp Glu Thr Val Pro Val Leu Ser Ser Gly Tyr Met Cys Ala Lys
            580                 585                 590
Gly Trp Arg Gly Lys Thr Arg Phe Asn Pro Ser Gly Met Arg Thr Tyr
        595                 600                 605
```

```
Val Arg Glu Tyr Asp His Ser Pro Pro Ala Asn Leu Leu Glu Gly Arg
    610                 615                 620

Gly Thr Gln Ser Gly Ala His Val Asp Ile Met Gly Asn Phe Ala Leu
625                 630                 635                 640

Ile Glu Asp Val Ile Arg Val Ala Ala Gly Ala Lys Gly Glu Asp Leu
                645                 650                 655

Gly Gly Asp Lys Val Tyr Ser Asp Ile Phe Lys Trp Ser Glu Lys Ile
            660                 665                 670

Lys Leu Pro Leu
        675

<210> SEQ ID NO 25
<211> LENGTH: 2398
<212> TYPE: DNA
<213> ORGANISM: Helianthus sp.

<400> SEQUENCE: 25
```

| | | | | | |
|---|---|---|---|---|---|
| ccacgcgtcc | gcaccactct | ccgccgcttg | cacacgtcac | cacctcaact | ccacacgtca | 60 |
| cgcttcttca | tccatcctct | aaccgcttca | atccgactta | ctaatggcgt | tactccgaag | 120 |
| aagaaaacaa | ccagattccg | atccacatcc | ggatccgggt | caggatccga | aaccagatga | 180 |
| agaagacgat | aaggaacaaa | aagcgtcaaa | aaaatcaaac | aaaaacggta | aaataaagaa | 240 |
| ctattcgtgc | ctcgataact | gctgttggtt | cgtcggttgc | gtgtgctcgg | tgtggtggtt | 300 |
| gttgttgttt | ttgtataatg | ctatgccggc | gtcgttcccg | cagtttgtga | cggaagcgat | 360 |
| atccggaccg | tttccggatc | ctcccggagt | taagtgtttg | aaagaaggtt | tgaaggcgaa | 420 |
| gcatccggtg | gtgtttgtgc | cggggattgt | gaccggtgga | cttgagctgt | gggaagggca | 480 |
| ccagtgtatg | gatggattgt | tccggaaaag | gctttgggc | ggtacgtttg | gtgaggttta | 540 |
| taagaggcct | tcgtgtttggg | tacaacatat | gtcgctagac | aacaaaaccg | ggatggatcc | 600 |
| accgggtata | cgggtcaggc | ctgtcagtgg | acttgtagct | gctgactact | tcgctccagg | 660 |
| gtattttgtt | tgggctgttt | tgattgctaa | cttggcacgt | gttggctatg | aagagaaaaa | 720 |
| tatgtatatg | gctgcatatg | actggagact | ctcgtttcaa | aacacagagg | taagagacca | 780 |
| aacactgagc | cggataaaga | gcaatataga | actgatggtt | gctactaatg | gcgggaaaaa | 840 |
| ggcggttatc | atcccgcatt | caatgggtgt | tatctacttc | ctgcatttca | tgaaatgggt | 900 |
| cgaggcacca | gcaccaatgg | gtggcggagg | tggaccagat | tggtgtgcta | aacacataaa | 960 |
| agcggtgatg | aatatcggtg | gaccattttt | aggtgtccca | aaagctgtag | ccgggctttt | 1020 |
| ctctgcggaa | gctaaagata | ttgcatcagt | cagggcccct | gcaccaggtg | tgttagactc | 1080 |
| ggatttattt | cagattcaaa | cgttacaaca | tgtaatgaga | atgagccgca | catgggattc | 1140 |
| aaccatgtct | atgataccga | aaggcgggga | caccatttgg | ggcggcctca | attggtcacc | 1200 |
| cgaagaaggg | tatagtccaa | ggaggagtaa | acatggaaaa | aacgacactg | aatctcccac | 1260 |
| cgtaagtgat | tctgcaagtg | aagtaacaca | tgcaaattat | ggaaggatag | tatcgttcgg | 1320 |
| gagagatgta | gcagaggcac | catcttcaga | gatcgagagg | atagaattta | gaggtgctgt | 1380 |
| gaagggtatc | aatgttgcaa | acaatacatg | tcgggccgtg | tggaccgaat | accatgacat | 1440 |
| gggatttggt | ggaatcaagg | ctgttgcgga | gtacaaggta | tatacagctg | gcgaaatcgt | 1500 |
| ggaactgctg | gagtttgttg | ctccaaaaat | gatggaacgc | ggtagtgctc | atttttcgta | 1560 |
| tggtattgct | gacaatttgg | atgatccaaa | atatacacat | acaagtatt | ggtctaaccc | 1620 |
| attggagaca | aagttaccaa | acgctccaga | catggagatc | tattcaatgt | atggagttgg | 1680 |

-continued

```
catcccaacc gaaagagcat atgtctacaa actcacacct gcggcagagt gctacatacc    1740
attccaaatt gacacgtcag caaaggataa aggcgaggac gggtgtttaa aagacggggt    1800
ttatacggtt gacggggatg aaacagtacc agcactaagc gcgggttaca tgtgcgcaaa    1860
gggttggcgt gggaaaacgc gattcaatcc ttcgggaatt aaaacttatg tcagggaata    1920
cgatcacaac cctccatcca actttctcga gggccgggc actcaaagcg ggcccatgt     1980 ggatattatg ggtaattttc agttgattga agatgttata agagttgcag ccggagccac    2040
gggtgaagaa cttggaggtg atcaggtgta cactggtata ttcgagtggt ccgagaagat    2100
caatctaaag ttgtgaaata tgtgacttag attttataca acagtatat caggtgcgt     2160 ttgttacata gttttgatta gagatctgcg atacatggaa gattattgtg tcatatttaa    2220
accaataagg gttagtgcgc ttcttgcagt tctctacttg aatttgtcta tgtattaagc    2280
gtgaactcta tgtgcattat tgatccacaa atctgtattg tgggtggatt attttgtaat    2340
atgtagcatg ttgcttcctt gaacagccaa aaaaaaaaaa aaaaaaaaaa aaaaaaa      2398
```

<210> SEQ ID NO 26
<211> LENGTH: 670
<212> TYPE: PRT
<213> ORGANISM: Helianthus sp.

<400> SEQUENCE: 26

```
Met Ala Leu Leu Arg Arg Arg Lys Gln Pro Asp Ser Asp Pro His Pro
  1               5                  10                  15

Asp Pro Gly Gln Asp Pro Lys Pro Asp Glu Glu Asp Asp Lys Glu Gln
                 20                  25                  30

Lys Ala Ser Lys Lys Ser Asn Lys Asn Gly Lys Ile Lys Asn Tyr Ser
             35                  40                  45

Cys Leu Asp Asn Cys Cys Trp Phe Val Gly Cys Val Cys Ser Val Trp
         50                  55                  60

Trp Leu Leu Leu Phe Leu Tyr Asn Ala Met Pro Ala Ser Phe Pro Gln
 65                  70                  75                  80

Phe Val Thr Glu Ala Ile Ser Gly Pro Phe Pro Asp Pro Pro Gly Val
                 85                  90                  95

Lys Cys Leu Lys Glu Gly Leu Lys Ala Lys His Pro Val Val Phe Val
            100                 105                 110

Pro Gly Ile Val Thr Gly Gly Leu Glu Leu Trp Glu Gly His Gln Cys
        115                 120                 125

Met Asp Gly Leu Phe Arg Lys Arg Leu Trp Gly Gly Thr Phe Gly Glu
    130                 135                 140

Val Tyr Lys Arg Pro Ser Cys Trp Val Gln His Met Ser Leu Asp Asn
145                 150                 155                 160

Lys Thr Gly Met Asp Pro Pro Gly Ile Arg Val Arg Pro Val Ser Gly
                165                 170                 175

Leu Val Ala Ala Asp Tyr Phe Ala Pro Gly Tyr Phe Val Trp Ala Val
            180                 185                 190

Leu Ile Ala Asn Leu Ala Arg Val Gly Tyr Glu Glu Lys Asn Met Tyr
        195                 200                 205

Met Ala Ala Tyr Asp Trp Arg Leu Ser Phe Gln Asn Thr Glu Val Arg
    210                 215                 220

Asp Gln Thr Leu Ser Arg Ile Lys Ser Asn Ile Glu Leu Met Val Ala
225                 230                 235                 240

Thr Asn Gly Gly Lys Lys Ala Val Ile Ile Pro His Ser Met Gly Val
```

-continued

```
                245                 250                 255
Ile Tyr Phe Leu His Phe Met Lys Trp Val Glu Ala Pro Ala Pro Met
                260                 265                 270
Gly Gly Gly Gly Gly Pro Asp Trp Cys Ala Lys His Ile Lys Ala Val
            275                 280                 285
Met Asn Ile Gly Gly Pro Phe Leu Gly Val Pro Lys Ala Val Ala Gly
        290                 295                 300
Leu Phe Ser Ala Glu Ala Lys Asp Ile Ala Ser Val Arg Ala Leu Ala
305                 310                 315                 320
Pro Gly Val Leu Asp Ser Asp Leu Phe Gln Ile Gln Thr Leu Gln His
                325                 330                 335
Val Met Arg Met Ser Arg Thr Trp Asp Ser Thr Met Ser Met Ile Pro
                340                 345                 350
Lys Gly Gly Asp Thr Ile Trp Gly Gly Leu Asn Trp Ser Pro Glu Glu
            355                 360                 365
Gly Tyr Ser Pro Arg Arg Ser Lys His Gly Lys Asn Asp Thr Glu Ser
        370                 375                 380
Pro Thr Val Ser Asp Ser Ala Ser Glu Val Thr His Ala Asn Tyr Gly
385                 390                 395                 400
Arg Ile Val Ser Phe Gly Arg Asp Val Ala Glu Ala Pro Ser Ser Glu
                405                 410                 415
Ile Glu Arg Ile Glu Phe Arg Gly Ala Val Lys Gly Ile Asn Val Ala
                420                 425                 430
Asn Asn Thr Cys Arg Ala Val Trp Thr Glu Tyr His Asp Met Gly Phe
            435                 440                 445
Gly Gly Ile Lys Ala Val Ala Glu Tyr Lys Val Tyr Thr Ala Gly Glu
        450                 455                 460
Ile Val Glu Leu Leu Glu Phe Val Ala Pro Lys Met Met Glu Arg Gly
465                 470                 475                 480
Ser Ala His Phe Ser Tyr Gly Ile Ala Asp Asn Leu Asp Asp Pro Lys
                485                 490                 495
Tyr Thr His Tyr Lys Tyr Trp Ser Asn Pro Leu Glu Thr Lys Leu Pro
            500                 505                 510
Asn Ala Pro Asp Met Glu Ile Tyr Ser Met Tyr Gly Val Gly Ile Pro
        515                 520                 525
Thr Glu Arg Ala Tyr Val Tyr Lys Leu Thr Pro Ala Ala Glu Cys Tyr
        530                 535                 540
Ile Pro Phe Gln Ile Asp Thr Ser Ala Lys Asp Lys Gly Glu Asp Gly
545                 550                 555                 560
Cys Leu Lys Asp Gly Val Tyr Thr Val Asp Gly Asp Glu Thr Val Pro
                565                 570                 575
Ala Leu Ser Ala Gly Tyr Met Cys Ala Lys Gly Trp Arg Gly Lys Thr
            580                 585                 590
Arg Phe Asn Pro Ser Gly Ile Lys Thr Tyr Val Arg Glu Tyr Asp His
        595                 600                 605
Asn Pro Pro Ser Asn Phe Leu Glu Gly Arg Gly Thr Gln Ser Gly Ala
        610                 615                 620
His Val Asp Ile Met Gly Asn Phe Gln Leu Ile Glu Asp Val Ile Arg
625                 630                 635                 640
Val Ala Ala Gly Ala Thr Gly Glu Glu Leu Gly Gly Asp Gln Val Tyr
            645                 650                 655
Thr Gly Ile Phe Glu Trp Ser Glu Lys Ile Asn Leu Lys Leu
        660                 665                 670
```

<210> SEQ ID NO 27
<211> LENGTH: 2030
<212> TYPE: DNA
<213> ORGANISM: Triticum aestivum

<400> SEQUENCE: 27

| | | | | | |
|---|---|---|---|---|---|
| ctcgtgccga | attcggcacg | agcggaggcc | atcacgggcc | cgctcccgga | cccgcccggg | 60 |
| gtcaagctgc | agaaggaggg | gctgcacgcc | aagcaccccg | tcatcttcgt | gccggggatc | 120 |
| gtcaccggag | ggctcgagct | ctgggagggc | caccactgcg | ccgagggct | cttccggaag | 180 |
| cgcctctggg | gcggcacatt | cggcgacgtg | tacaagaggc | ctttatgctg | gattgaacat | 240 |
| atgtcattgg | acaacgaaac | tggattagat | aaaccaggaa | taagagttag | gccagtcaca | 300 |
| ggccttgtcg | cagctgacta | ttttgtccct | ggctattttg | tttgggcagt | cctgattgcc | 360 |
| aatttagctc | ggattggata | tgaagaaaag | aacatgtaca | tggctgctta | tgattggagg | 420 |
| ttatcattcc | agaacactga | gacccgtgat | caaacattga | gcagaataaa | gagtaacatt | 480 |
| gagctcttgg | tagcgactaa | tggtggaaat | agggcggtgg | tgatcccaca | ttccatggga | 540 |
| gttctctatt | ttcttcattt | tatgaagtgg | gtagaagcac | cttctcccat | gggtggtggt | 600 |
| ggtggtcctg | attggtgtgc | aaagcacatc | aaagctgtag | caaacattgg | tgggcctttc | 660 |
| ttaggagttc | caaaggctgt | tgctgggctt | ttctcatctg | aagccaaaga | tgttgctgtt | 720 |
| gctagagcta | ttgcaccaga | aatgctggac | tcagattttc | ttggacttca | gaccttgcgc | 780 |
| cacttgatgc | gaatgacccg | tacatgggat | tcaacaatgt | caatgctccc | taaggtggt | 840 |
| gagactattt | ggggaggttt | ggattggtct | ccagaagatg | gttttgagtg | taaatccaag | 900 |
| aagcggaaga | ccaatgattc | agaggtttct | aaggatgttc | atggggaacc | tgtcgaagtt | 960 |
| aatccagagc | ctgtgaactt | tggaagaatg | gtatcttttg | gaaagatgt | agcggaagct | 1020 |
| ccggcttcaa | atattgagca | gatagaattc | cgtgatgctc | tcaaaggtaa | taatcttgcc | 1080 |
| cattcgaata | catcatgccg | ggatgtctgg | acagagtatc | aggaattagg | gtggggtgga | 1140 |
| ataaaggcag | tttcagacta | caaagctttc | accgcaggct | ctatcataga | tcttttttaac | 1200 |
| tttgttgctc | caaggatgat | gcagcgtggt | agtgttcatt | tttcatatgg | aattgctgat | 1260 |
| aacttggatg | atccaaaata | tggccactac | aagtattggt | caaacccctt | ggagacaaaa | 1320 |
| ctaccagatg | cgcctgaaat | ggaaatattt | tcgatgtatg | gagtaggcat | tcctaccgaa | 1380 |
| agagcatatg | tctataaatt | atccccacag | gcagagtgct | ataacccctt | tcagatagat | 1440 |
| gcctcagctg | agggtgggga | tgagaatagc | tgcttgaaag | gtggtgttta | catgtcgaat | 1500 |
| ggtgacgaga | ctgttccagt | tcttagttca | gggtatatgt | gtgccaaagc | atggcgtgga | 1560 |
| aaaactcgct | tcaacccttc | tggcagcaag | acttacgtga | gagagtatag | tcattctcca | 1620 |
| ccctcgaatc | tcctcgaagg | caggggcaca | cagagtggtg | cccacgttga | tattatgggg | 1680 |
| aactttgctt | taatggagga | tattatcagg | attgctgctg | gggcaaccgg | tgaggaaatt | 1740 |
| ggtggtgatc | aggtgtattc | tgatatattc | aaatggtccg | agaagataaa | gctgaaattg | 1800 |
| tagttagtag | gaaatcatgt | gatttgtggt | gacgaagcag | attttactct | ggtcgaatcc | 1860 |
| tattaattt | gatttgataa | tgtaatggtt | tttgctctga | cactggcgtt | attgtgaaac | 1920 |
| cgcggtgtat | attaaaatgt | atagatggaa | gctgtgatac | ttctgttaaa | aaaaaaaaa | 1980 |
| aaaaaaaaaa | aaaaaaaaaa | aaaaaaaaaa | aaaaaaaaaa | aaaaaaaaaa | | 2030 |

<210> SEQ ID NO 28

<211> LENGTH: 600
<212> TYPE: PRT
<213> ORGANISM: Triticum aestivum

<400> SEQUENCE: 28

```
Leu Val Pro Asn Ser Ala Arg Ala Glu Ala Ile Thr Gly Pro Leu Pro
  1               5                  10                  15

Asp Pro Pro Gly Val Lys Leu Gln Lys Glu Gly Leu His Ala Lys His
             20                  25                  30

Pro Val Ile Phe Val Pro Gly Ile Val Thr Gly Gly Leu Glu Leu Trp
         35                  40                  45

Glu Gly His His Cys Ala Glu Gly Leu Phe Arg Lys Arg Leu Trp Gly
     50                  55                  60

Gly Thr Phe Gly Asp Val Tyr Lys Arg Pro Leu Cys Trp Ile Glu His
 65                  70                  75                  80

Met Ser Leu Asp Asn Glu Thr Gly Leu Asp Lys Pro Gly Ile Arg Val
                 85                  90                  95

Arg Pro Val Thr Gly Leu Val Ala Ala Asp Tyr Phe Val Pro Gly Tyr
            100                 105                 110

Phe Val Trp Ala Val Leu Ile Ala Asn Leu Ala Arg Ile Gly Tyr Glu
        115                 120                 125

Glu Lys Asn Met Tyr Met Ala Ala Tyr Asp Trp Arg Leu Ser Phe Gln
    130                 135                 140

Asn Thr Glu Thr Arg Asp Gln Thr Leu Ser Arg Ile Lys Ser Asn Ile
145                 150                 155                 160

Glu Leu Leu Val Ala Thr Asn Gly Gly Asn Arg Ala Val Val Ile Pro
                165                 170                 175

His Ser Met Gly Val Leu Tyr Phe Leu His Phe Met Lys Trp Val Glu
            180                 185                 190

Ala Pro Ser Pro Met Gly Gly Gly Gly Pro Asp Trp Cys Ala Lys
        195                 200                 205

His Ile Lys Ala Val Ala Asn Ile Gly Gly Pro Phe Leu Gly Val Pro
    210                 215                 220

Lys Ala Val Ala Gly Leu Phe Ser Ser Glu Ala Lys Asp Val Ala Val
225                 230                 235                 240

Ala Arg Ala Ile Ala Pro Glu Met Leu Asp Ser Asp Phe Leu Gly Leu
                245                 250                 255

Gln Thr Leu Arg His Leu Met Arg Met Thr Arg Thr Trp Asp Ser Thr
            260                 265                 270

Met Ser Met Leu Pro Lys Gly Gly Glu Thr Ile Trp Gly Gly Leu Asp
        275                 280                 285

Trp Ser Pro Glu Asp Gly Phe Glu Cys Lys Ser Lys Arg Lys Thr
    290                 295                 300

Asn Asp Ser Glu Val Ser Lys Asp Val His Gly Glu Pro Val Glu Val
305                 310                 315                 320

Asn Pro Glu Pro Val Asn Phe Gly Arg Met Val Ser Phe Gly Lys Asp
                325                 330                 335

Val Ala Glu Ala Pro Ala Ser Asn Glu Gln Ile Glu Phe Arg Asp
            340                 345                 350

Ala Val Lys Gly Asn Asn Leu Ala His Ser Asn Thr Ser Cys Arg Asp
        355                 360                 365

Val Trp Thr Glu Tyr Gln Glu Leu Gly Trp Gly Ile Lys Ala Val
    370                 375                 380

Ser Asp Tyr Lys Ala Phe Thr Ala Gly Ser Ile Ile Asp Leu Phe Asn
```

```
                385                 390                 395                 400
Phe Val Ala Pro Arg Met Met Gln Arg Gly Ser Val His Phe Ser Tyr
                405                 410                 415
Gly Ile Ala Asp Asn Leu Asp Asp Pro Lys Tyr Gly His Tyr Lys Tyr
                420                 425                 430
Trp Ser Asn Pro Leu Glu Thr Lys Leu Pro Asp Ala Pro Glu Met Glu
                435                 440                 445
Ile Phe Ser Met Tyr Gly Val Gly Ile Pro Thr Glu Arg Ala Tyr Val
        450                 455                 460
Tyr Lys Leu Ser Pro Gln Ala Glu Cys Tyr Ile Pro Phe Gln Ile Asp
465                 470                 475                 480
Ala Ser Ala Glu Gly Gly Asp Glu Asn Ser Cys Leu Lys Gly Gly Val
                    485                 490                 495
Tyr Met Ser Asn Gly Asp Glu Thr Val Pro Val Leu Ser Ser Gly Tyr
                500                 505                 510
Met Cys Ala Lys Ala Trp Arg Gly Lys Thr Arg Phe Asn Pro Ser Gly
                515                 520                 525
Ser Lys Thr Tyr Val Arg Glu Tyr Ser His Ser Pro Pro Ser Asn Leu
        530                 535                 540
Leu Glu Gly Arg Gly Thr Gln Ser Gly Ala His Val Asp Ile Met Gly
545                 550                 555                 560
Asn Phe Ala Leu Met Glu Asp Ile Ile Arg Ile Ala Ala Gly Ala Thr
                    565                 570                 575
Gly Glu Glu Ile Gly Gly Asp Gln Val Tyr Ser Asp Ile Phe Lys Trp
                580                 585                 590
Ser Glu Lys Ile Lys Leu Lys Leu
        595                 600

<210> SEQ ID NO 29
<211> LENGTH: 493
<212> TYPE: PRT
<213> ORGANISM: Arabidopsis thaliana

<400> SEQUENCE: 29

Met Ser Leu Leu Leu Glu Glu Ile Ile Arg Ser Val Glu Ala Leu Leu
1               5                   10                  15
Lys Leu Arg Asn Arg Asn Gln Glu Pro Tyr Val Asp Pro Asn Leu Asn
                20                  25                  30
Pro Val Leu Leu Val Pro Gly Ile Ala Gly Ser Ile Leu Asn Ala Val
            35                  40                  45
Asp His Glu Asn Gly Asn Glu Glu Arg Val Trp Val Arg Ile Phe Gly
        50                  55                  60
Ala Asp His Glu Phe Arg Thr Lys Met Trp Ser Arg Phe Asp Pro Ser
65                  70                  75                  80
Thr Gly Lys Thr Ile Ser Leu Asp Pro Lys Thr Ser Ile Val Val Pro
                85                  90                  95
Gln Asp Arg Ala Gly Leu His Ala Ile Asp Val Leu Asp Pro Asp Met
                100                 105                 110
Ile Val Gly Arg Glu Ser Val Tyr Tyr Phe His Glu Met Ile Val Glu
            115                 120                 125
Met Ile Gly Trp Gly Phe Glu Glu Gly Lys Thr Leu Phe Gly Phe Gly
        130                 135                 140
Tyr Asp Phe Arg Gln Ser Asn Arg Leu Gln Glu Thr Leu Asp Gln Phe
145                 150                 155                 160
```

```
Ala Lys Lys Leu Glu Thr Val Tyr Lys Ala Ser Gly Glu Lys Ile
                165                 170                 175

Asn Val Ile Ser His Ser Met Gly Gly Leu Leu Val Lys Cys Phe Met
            180                 185                 190

Gly Leu His Ser Asp Val Cys Lys Ser Leu Phe Leu Tyr Ser Tyr Ser
        195                 200                 205

Arg Ser Met Tyr Arg Ile Gly Leu Leu Leu Leu His Phe Glu Val
    210                 215                 220

Ser Ser Leu Thr Cys Gly Thr Ser Asp Ser Thr Gly Asp Asn Tyr His
225                 230                 235                 240

Thr Asp Trp Phe Arg Ile Ile Asp Ser Gly Ala Pro Gly Tyr Ile Thr
                245                 250                 255

Ser Thr Leu Leu Asn Gly Met Ser Phe Val Asn Gly Trp Glu Gln Asn
            260                 265                 270

Phe Phe Val Ser Lys Trp Ser Met His Gln Leu Ser Cys Gly Glu Arg
        275                 280                 285

Lys Arg Ala Met Met Glu Leu Glu Pro Leu Met Leu Phe Leu Ser Leu
    290                 295                 300

Thr Val Ala Trp Arg Ala Leu Lys Phe Leu Arg Asn Leu Phe Arg Ile
305                 310                 315                 320

Ile His Tyr Gly Asn Glu Lys Met Pro Val Lys Asp Leu Thr Asn Leu
                325                 330                 335

Arg Tyr Phe Gln Pro Thr Tyr Ile Cys Val Asp Gly Asp Gly Thr Val
            340                 345                 350

Pro Met Glu Ser Ala Met Ala Asp Gly Leu Glu Ala Val Ala Arg Val
        355                 360                 365

Gly Val Pro Gly Glu His Arg Gly Ile Leu Asn Asp His Arg Val Phe
    370                 375                 380

Arg Met Leu Lys Lys Trp Leu Asn Val Gly Glu Pro Asp Pro Phe Tyr
385                 390                 395                 400

Asn Pro Val Asn Asp Tyr Val Ile Leu Pro Thr Thr Tyr Glu Phe Glu
                405                 410                 415

Lys Phe His Glu Asn Gly Leu Glu Val Ala Ser Val Lys Glu Ser Trp
            420                 425                 430

Asp Ile Ile Ser Asp Asp Asn Asn Ile Gly Thr Thr Gly Ser Thr Val
        435                 440                 445

Asn Ser Ile Ser Val Ser Gln Pro Gly Asp Asp Gln Asn Pro Gln Ala
450                 455                 460

Glu Ala Arg Ala Thr Leu Thr Val Gln Pro Gln Ser Asp Gly Arg Gln
465                 470                 475                 480

His Val Glu Leu Asn Ala Val Ser Val Ser Val Asp Ala
                485                 490
```

<210> SEQ ID NO 30
<211> LENGTH: 671
<212> TYPE: PRT
<213> ORGANISM: Arabidopsis thaliana

<400> SEQUENCE: 30

```
Met Pro Leu Ile His Arg Lys Lys Pro Thr Glu Lys Pro Ser Thr Pro
 1               5                  10                  15

Pro Ser Glu Glu Val Val His Asp Glu Asp Ser Gln Lys Lys Pro His
            20                  25                  30

Glu Ser Ser Lys Ser His His Lys Lys Ser Asn Gly Gly Gly Lys Trp
        35                  40                  45
```

```
Ser Cys Ile Asp Ser Cys Cys Trp Phe Ile Gly Cys Val Cys Val Thr
    50                  55                  60

Trp Trp Phe Leu Leu Phe Leu Tyr Asn Ala Met Pro Ala Ser Phe Pro
65                  70                  75                  80

Gln Tyr Val Thr Glu Arg Ile Thr Gly Pro Leu Pro Asp Pro Pro Gly
                85                  90                  95

Val Lys Leu Lys Lys Glu Gly Leu Lys Ala Lys His Pro Val Val Phe
                100                 105                 110

Ile Pro Gly Ile Val Thr Gly Gly Leu Glu Leu Trp Glu Gly Lys Gln
            115                 120                 125

Cys Ala Asp Gly Leu Phe Arg Lys Arg Leu Trp Gly Thr Phe Gly
130                 135                 140

Glu Val Tyr Lys Arg Pro Leu Cys Trp Val Glu His Met Ser Leu Asp
145                 150                 155                 160

Asn Glu Thr Gly Leu Asp Pro Ala Gly Ile Arg Val Arg Ala Val Ser
                165                 170                 175

Gly Leu Val Ala Ala Asp Tyr Phe Ala Pro Gly Tyr Phe Val Trp Ala
                180                 185                 190

Val Leu Ile Ala Asn Leu Ala His Ile Gly Tyr Glu Glu Lys Asn Met
            195                 200                 205

Tyr Met Ala Ala Tyr Asp Trp Arg Leu Ser Phe Gln Asn Thr Glu Val
    210                 215                 220

Arg Asp Gln Thr Leu Ser Arg Met Lys Ser Asn Ile Glu Leu Met Val
225                 230                 235                 240

Ser Thr Asn Gly Gly Lys Lys Ala Val Ile Val Pro His Ser Met Gly
                245                 250                 255

Val Leu Tyr Phe Leu His Phe Met Lys Trp Val Glu Ala Pro Ala Pro
                260                 265                 270

Leu Gly Gly Gly Gly Pro Asp Trp Cys Ala Lys Tyr Ile Lys Ala
                275                 280                 285

Val Met Asn Ile Gly Gly Pro Phe Leu Gly Val Pro Lys Ala Val Ala
    290                 295                 300

Gly Leu Phe Ser Ala Glu Ala Lys Asp Val Ala Val Ala Arg Ala Ile
305                 310                 315                 320

Ala Pro Gly Phe Leu Asp Thr Asp Ile Phe Arg Leu Gln Thr Leu Gln
                325                 330                 335

His Val Met Arg Met Thr Arg Thr Trp Asp Ser Thr Met Ser Met Leu
                340                 345                 350

Pro Lys Gly Gly Asp Thr Ile Trp Gly Gly Leu Asp Trp Ser Pro Glu
                355                 360                 365

Lys Gly His Thr Cys Cys Gly Lys Lys Gln Lys Asn Asn Glu Thr Cys
    370                 375                 380

Gly Glu Ala Gly Glu Asn Gly Val Ser Lys Ser Pro Val Asn Tyr
385                 390                 395                 400

Gly Arg Met Ile Ser Phe Gly Lys Glu Val Ala Glu Ala Ala Pro Ser
                405                 410                 415

Glu Ile Asn Asn Ile Asp Phe Arg Gly Ala Val Lys Gly Gln Ser Ile
                420                 425                 430

Pro Asn His Thr Cys Arg Asp Val Trp Thr Glu Tyr His Asp Met Gly
                435                 440                 445

Ile Ala Gly Ile Lys Ala Ile Ala Glu Tyr Lys Val Tyr Thr Ala Gly
450                 455                 460
```

```
Glu Ala Ile Asp Leu Leu His Tyr Val Ala Pro Lys Met Met Ala Arg
465                 470                 475                 480
Gly Ala Ala His Phe Ser Tyr Gly Ile Ala Asp Leu Asp Asp Thr
                485                 490                 495
Lys Tyr Gln Asp Pro Lys Tyr Trp Ser Asn Pro Leu Glu Thr Lys Leu
            500                 505                 510
Pro Asn Ala Pro Glu Met Glu Ile Tyr Ser Leu Tyr Gly Val Gly Ile
        515                 520                 525
Pro Thr Glu Arg Ala Tyr Val Tyr Lys Leu Asn Gln Ser Pro Asp Ser
    530                 535                 540
Cys Ile Pro Phe Gln Ile Phe Thr Ser Ala His Glu Glu Asp Glu Asp
545                 550                 555                 560
Ser Cys Leu Lys Ala Gly Val Tyr Asn Val Asp Gly Asp Glu Thr Val
                565                 570                 575
Pro Val Leu Ser Ala Gly Tyr Met Cys Ala Lys Ala Trp Arg Gly Lys
                580                 585                 590
Thr Arg Phe Asn Pro Ser Gly Ile Lys Thr Tyr Ile Arg Glu Tyr Asn
            595                 600                 605
His Ser Pro Pro Ala Asn Leu Leu Glu Gly Arg Gly Thr Gln Ser Gly
        610                 615                 620
Ala His Val Asp Ile Met Gly Asn Phe Ala Leu Ile Glu Asp Ile Met
625                 630                 635                 640
Arg Val Ala Ala Gly Gly Asn Gly Ser Asp Ile Gly His Asp Gln Val
                645                 650                 655
His Ser Gly Ile Phe Glu Trp Ser Glu Arg Ile Asp Leu Lys Leu
            660                 665                 670

<210> SEQ ID NO 31
<211> LENGTH: 1957
<212> TYPE: DNA
<213> ORGANISM: C. tetragonoloba

<400> SEQUENCE: 31
gcacgagggt taacagcacc ttcacctaat agaaacccta tttcccaatt cgatttccgg    60
tgaattatcc attctggaaa ctcccgatca atcaattggt tgttgttagg gtttccattt   120
gcagatggcg atcttgttgg acgagatcct acaatccttg gagttatggc tgaagctgat   180
caagaagccc agccagagc cctacatcaa ccctaatcta daccctgttt tattggtgcc   240
tggaatcggc ggctccatgt tgcatgctgt aagcgattcc aacggcaaca gagaacgggt   300
ttgggttcgc ttcctcggcg cggattacat gttgaggacc aagctttggt cacgttacga   360
tccttctacc ggaaaatcca tatccttgga tacaaataca acaattttga ttcctgaaga   420
taggcatgga ctttatgcaa ttgatgtttt ggaccccgac ttggtaattg aagcgagtc    480
tgtttattat ttccatgaca tgatcgtgga aatgcgcaaa tgggggtatc aagagggaaa   540
gacactttt ggctttggat atgattttcg acaaagcaac aggttgcagg aaacaataga   600
tcggttggct gcaaaattag aatcaattta tgatgctgct ggagggaaaa agataaacat   660
cataagtcat tctatgggcg gtcttttggt gaaatgtttc atgtgcctgc aaagtgatat   720
ttttgagaaa tgtgttaaga attgggttgc aattgctgca ccattccagg gtgcacctgg   780
atgtatcaat tctaccttgt taaatggaat gtcatttgta gatggatggg agcaaaaggt   840
ttacatttcc aaatggagca tgcaccagtt gctgattgaa tgtccatcaa tttacgaact   900
tatgggttgt cctaatttc attggcaaca tattcctctt ctggaattgt ggcgtgagag   960
```

-continued

```
acatgattct gatgggaaat ctggtattat tctggaatca tatccaccgt gtgatagcgt    1020
tgaggttttg aagcaagctc ttgtaaataa cacagttaat tataatggtg aggatttacc    1080
ccttcccttc aacacagaga tcttgaaatg ggccaaaaaa acttgggaga tcctgtcttc    1140
tgccaaactt cctccaaatg ttaaatttta caatatttat gggactaatc tcgagacggc    1200
tcatagcatt tgctatggaa gtgcagacaa gcctgtctca gatctgcagc agctacgtta    1260
ttaccagccc aaatacgtat gtgttgatgg cgacggaaca gttccggtag aatcagctaa    1320
ggctgacggg ctcaatgcgg aggcgagggt tggagtccca ggcgaacatc gaggtatcct    1380
tcgtgaccct catgtattca ggattctcaa gcactggcta aaggctggag atcctgatcc    1440
cttttacaac cctctcaatg attatgtgat tctacctact gcttttgaaa tggagagtca    1500
taaagagaaa ggtttagaag tagcatccct taaagaggag tgggaaatta tttccaaaga    1560
ccaagatgaa caacaaagca atattgctga agaaatgtct ctgagtacca tatcagtttc    1620
gcatgaagga gccaatcaat cttgttccga ggctcatgct actgtcgtcg ttcgcccagg    1680
cgatgagggt aaacaacaca ttcaactgaa tgtcgttgct gtttcagtcg atgcctcatg    1740
aatccatgtg ttgaagaaga atgagtgaag gtggagggaa atacttgcta catagttgat    1800
tgtgggtgat ttctcttgta tataaggata ttcgattgat gctgctgctg ccatattctt    1860
ccttgtatga tatacgatat accaatatgt atcattggaa aaaaataatt aaaagaaaag    1920
aaaaatacca tcttctatga caaaaaaaaa aaaaaaa                             1957
```

<210> SEQ ID NO 32
<211> LENGTH: 538
<212> TYPE: PRT
<213> ORGANISM: C. tetragonoloba

<400> SEQUENCE: 32

```
Met Ala Ile Leu Leu Asp Glu Ile Leu Gln Ser Leu Glu Leu Trp Leu
  1               5                  10                  15

Lys Leu Ile Lys Lys Pro Gln Pro Glu Pro Tyr Ile Asn Pro Asn Leu
             20                  25                  30

Asp Pro Val Leu Leu Val Pro Gly Ile Gly Gly Ser Met Leu His Ala
         35                  40                  45

Val Ser Asp Ser Asn Gly Asn Arg Glu Arg Val Trp Val Arg Phe Leu
     50                  55                  60

Gly Ala Asp Tyr Met Leu Arg Thr Lys Leu Trp Ser Arg Tyr Asp Pro
 65                  70                  75                  80

Ser Thr Gly Lys Ser Ile Ser Leu Asp Thr Asn Thr Thr Ile Leu Ile
                 85                  90                  95

Pro Glu Asp Arg His Gly Leu Tyr Ala Ile Asp Val Leu Asp Pro Asp
            100                 105                 110

Leu Val Ile Gly Ser Glu Ser Val Tyr Tyr Phe His Asp Met Ile Val
        115                 120                 125

Glu Met Arg Lys Trp Gly Tyr Gln Glu Gly Lys Thr Leu Phe Gly Phe
    130                 135                 140

Gly Tyr Asp Phe Arg Gln Ser Asn Arg Leu Gln Glu Thr Ile Asp Arg
145                 150                 155                 160

Leu Ala Ala Lys Leu Glu Ser Ile Tyr Asp Ala Ala Gly Gly Lys Lys
                165                 170                 175

Ile Asn Ile Ile Ser His Ser Met Gly Gly Leu Leu Val Lys Cys Phe
            180                 185                 190

Met Cys Leu Gln Ser Asp Ile Phe Glu Lys Cys Val Lys Asn Trp Val
```

```
                195                 200                 205
Ala Ile Ala Ala Pro Phe Gln Gly Ala Pro Gly Cys Ile Asn Ser Thr
    210                 215                 220

Leu Leu Asn Gly Met Ser Phe Val Asp Gly Trp Glu Gln Lys Val Tyr
225                 230                 235                 240

Ile Ser Lys Trp Ser Met His Gln Leu Leu Ile Glu Cys Pro Ser Ile
                245                 250                 255

Tyr Glu Leu Met Gly Cys Pro Asn Phe His Trp Gln His Ile Pro Leu
                260                 265                 270

Leu Glu Leu Trp Arg Glu Arg His Asp Ser Asp Gly Lys Ser Gly Ile
            275                 280                 285

Ile Leu Glu Ser Tyr Pro Pro Cys Asp Ser Val Glu Val Leu Lys Gln
        290                 295                 300

Ala Leu Val Asn Asn Thr Val Asn Tyr Asn Gly Glu Asp Leu Pro Leu
305                 310                 315                 320

Pro Phe Asn Thr Glu Ile Leu Lys Trp Ala Lys Lys Thr Trp Glu Ile
                325                 330                 335

Leu Ser Ser Ala Lys Leu Pro Pro Asn Val Lys Phe Tyr Asn Ile Tyr
            340                 345                 350

Gly Thr Asn Leu Glu Thr Ala His Ser Ile Cys Tyr Gly Ser Ala Asp
        355                 360                 365

Lys Pro Val Ser Asp Leu Gln Gln Leu Arg Tyr Tyr Gln Pro Lys Tyr
    370                 375                 380

Val Cys Val Asp Gly Asp Gly Thr Val Pro Val Glu Ser Ala Lys Ala
385                 390                 395                 400

Asp Gly Leu Asn Ala Glu Ala Arg Val Gly Val Pro Gly Glu His Arg
                405                 410                 415

Gly Ile Leu Arg Asp Pro His Val Phe Arg Ile Leu Lys His Trp Leu
            420                 425                 430

Lys Ala Gly Asp Pro Asp Pro Phe Tyr Asn Pro Leu Asn Asp Tyr Val
        435                 440                 445

Ile Leu Pro Thr Ala Phe Glu Met Glu Ser His Lys Glu Lys Gly Leu
    450                 455                 460

Glu Val Ala Ser Leu Lys Glu Glu Trp Glu Ile Ile Ser Lys Asp Gln
465                 470                 475                 480

Asp Glu Gln Gln Ser Asn Ile Ala Glu Glu Met Ser Leu Ser Thr Ile
                485                 490                 495

Ser Val Ser His Glu Gly Ala Asn Gln Ser Cys Ser Glu Ala His Ala
            500                 505                 510

Thr Val Val Arg Pro Gly Asp Glu Gly Lys Gln His Ile Gln Leu
        515                 520                 525

Asn Val Val Ala Val Ser Val Asp Ala Ser
    530                 535

<210> SEQ ID NO 33
<211> LENGTH: 2077
<212> TYPE: DNA
<213> ORGANISM: Triticum aestivum

<400> SEQUENCE: 33
cgcctccgga atccccaccc ccgtccaaat ccgggcaaac catataccccc agctacccgc      60 cgcggagcag attccccgcc atccgccgac gccacgccac gccaccccg tgccgctccg       120 attcgagctt gccggagctc ggtttggccg aagcctcgc cctctcatgc tgatctcgcg       180
```

-continued

```
gccgggggct tgagagtgct tatttagggc ggggatttgg gcggcgggga agcaaggatg      240
tcggtgctgg aggatttgat ccgggcgatc gagctgtggc tgcggatcgc caaggagcag      300
gtgccgctgg tcgacccag cctcgacccg gtgctgctcg tgcccggcat cggcggctcc      360
atcctcgagg ccgtggacga ggccgggaac aaggagcggg tctgggtgcg catcctcgcc      420
gccgaccacg agtgccgcga gaagctctgg gcgcagttcg atgcctccac tggcaaaact      480
atttctgtgg atgagaaaat acgcatcact gtcccggagg ataggtatgg attgtacgcc      540
atcgacacat tggacccaga cctgattatt ggtgatgaca gtgtttacta ctatcatgac      600
atgatagtgc aaatgattaa atgggatat caagaaggca aaactctgtt cggatttggt      660
tatgatttcc gccaaagtaa caggcttcg gaaacacttg acaattttc taacaagcta      720 gagtcagtat acacagcttc aggagggaaa aagatcaatc taataacaca ttcaatgggg      780
ggattgcttg ttaaatgctt catgtctctt catggtgatg tctttgaaaa atatgtgaag      840
agttgggtta caattgctgc accatttcaa ggtgcgcctg gtacataaa tagtggtctg      900 ctgaatggaa tgtcttttgt ggaaggatgg caatcaaaat tcttcatttc caaatggact      960
atgcagcaat tgttgattga atgtccatca atatacgagt tgttggctag ctcaacctac      1020
cactgggaag atacaccatt gctacagatc tggaaagaga gcttagatga caatggcaag      1080
aaaagtgcca tactggagtc ctatgaacca gatgaagcaa taagatgat tcagaaagct      1140 cttccaagc atgagattat ctctgatgga atcacattc ctctgcccct taatgaggat      1200
atattaatat gggcaaagga aactcaagat atcttatccc aggcaaagct tccaaaatca      1260
gtgaagttct acaatattta cgggattgat tatgacactg ctcatactgt ttgctacggg      1320
agcaaacggc accctatttc aaatcttagt cacctcttat atactcaggg taaatacatc      1380
tgtgttgatg gtgatggatc cgttcccgca gaatcagcaa aggcggacgg ccttgatgca      1440
gtggcgagaa ttgggggttgc tgctgaccac cgaggaatcg tctgcgacca ccgcgtgttt      1500
cgcatagtcc agcattggct gcacgcgggt gaacctgacc cgttttacga cccgctcaac      1560
gactatgtcg tcatcccaac catcttcgag gtcgagaagc accacgagaa acgcggggac      1620
gtcacgtcgg tcagggagga ctgggagatc atctcccaca ccgatggcga cgaggccaaa      1680
aggctggctg agctccctgc tatggttggc gcgatgtctg cgtcttgcga gggtaaggat      1740
ggccttatgg acgaggcgca ggccaccgtg gtggtccacc cggagagcgg agggcggcag      1800
catgtggaag tcagggctgt cggagtcagc cacggtggct agctatgggc ctactcgccg      1860
tataacttta gctagggcga ttgcacatac tgtaaaccgt tgatgcacat aagatgtggc      1920
caagtaggga atatgtctct gtaaatacgg tatactgctg cttgtaaata tctgaacttg      1980
gaagcacaag gtgcactggc tatgagcacc aaggaggaag gaaataatca gaatggatta      2040
ccagcttgtc accttgtaaa aaaaaaaaaa aaaaaaa                               2077
```

<210> SEQ ID NO 34
<211> LENGTH: 534
<212> TYPE: PRT
<213> ORGANISM: Triticum aestivum

<400> SEQUENCE: 34

Met Ser Val Leu Glu Asp Leu Ile Arg Ala Ile Glu Leu Trp Leu Arg
1               5                   10                  15

Ile Ala Lys Glu Gln Val Pro Leu Val Asp Pro Ser Leu Asp Pro Val
            20                  25                  30

Leu Leu Val Pro Gly Ile Gly Gly Ser Ile Leu Glu Ala Val Asp Glu

-continued

```
               35                  40                  45
Ala Gly Asn Lys Glu Arg Val Trp Val Arg Ile Leu Ala Ala Asp His
         50                  55                  60

Glu Cys Arg Glu Lys Leu Trp Ala Gln Phe Asp Ala Ser Thr Gly Lys
 65                  70                  75                  80

Thr Ile Ser Val Asp Glu Lys Ile Arg Ile Thr Val Pro Glu Asp Arg
                 85                  90                  95

Tyr Gly Leu Tyr Ala Ile Asp Thr Leu Asp Pro Asp Leu Ile Ile Gly
            100                 105                 110

Asp Asp Ser Val Tyr Tyr His Asp Met Ile Val Gln Met Ile Lys
            115                 120                 125

Trp Gly Tyr Gln Glu Gly Lys Thr Leu Phe Gly Phe Gly Tyr Asp Phe
        130                 135                 140

Arg Gln Ser Asn Arg Leu Ser Glu Thr Leu Asp Lys Phe Ser Asn Lys
145                 150                 155                 160

Leu Glu Ser Val Tyr Thr Ala Ser Gly Gly Lys Lys Ile Asn Leu Ile
                165                 170                 175

Thr His Ser Met Gly Gly Leu Leu Val Lys Cys Phe Met Ser Leu His
            180                 185                 190

Gly Asp Val Phe Glu Lys Tyr Val Lys Ser Trp Val Ala Ile Ala Ala
            195                 200                 205

Pro Phe Gln Gly Ala Pro Gly Tyr Ile Asn Ser Gly Leu Leu Asn Gly
        210                 215                 220

Met Ser Phe Val Glu Gly Trp Gln Ser Lys Phe Phe Ile Ser Lys Trp
225                 230                 235                 240

Thr Met Gln Gln Leu Leu Ile Glu Cys Pro Ser Ile Tyr Glu Leu Leu
                245                 250                 255

Ala Ser Ser Thr Tyr His Trp Glu Asp Thr Pro Leu Leu Gln Ile Trp
            260                 265                 270

Lys Glu Ser Leu Asp Asp Asn Gly Lys Lys Ser Ala Ile Leu Glu Ser
            275                 280                 285

Tyr Glu Pro Asp Glu Ala Ile Lys Met Ile Gln Lys Ala Leu Ser Lys
        290                 295                 300

His Glu Ile Ile Ser Asp Gly Asn His Ile Pro Leu Pro Leu Asn Glu
305                 310                 315                 320

Asp Ile Leu Ile Trp Ala Lys Glu Thr Gln Asp Ile Leu Ser Gln Ala
                325                 330                 335

Lys Leu Pro Lys Ser Val Lys Phe Tyr Asn Ile Tyr Gly Ile Asp Tyr
            340                 345                 350

Asp Thr Ala His Thr Val Cys Tyr Gly Ser Lys Arg His Pro Ile Ser
            355                 360                 365

Asn Leu Ser His Leu Leu Tyr Thr Gln Gly Lys Tyr Ile Cys Val Asp
        370                 375                 380

Gly Asp Gly Ser Val Pro Ala Glu Ser Ala Lys Ala Asp Gly Leu Asp
385                 390                 395                 400

Ala Val Ala Arg Ile Gly Val Ala Ala Asp His Arg Gly Ile Val Cys
                405                 410                 415

Asp His Arg Val Phe Arg Ile Val Gln His Trp Leu His Ala Gly Glu
            420                 425                 430

Pro Asp Pro Phe Tyr Asp Pro Leu Asn Asp Tyr Val Val Ile Pro Thr
        435                 440                 445

Ile Phe Glu Val Glu Lys His His Glu Lys Arg Gly Asp Val Thr Ser
450                 455                 460
```

```
Val Arg Glu Asp Trp Glu Ile Ile Ser His Thr Asp Gly Asp Glu Ala
465                 470                 475                 480

Lys Arg Leu Ala Glu Leu Pro Ala Met Val Gly Ala Met Ser Ala Ser
                485                 490                 495

Cys Glu Gly Lys Asp Gly Leu Met Asp Glu Ala Gln Ala Thr Val Val
            500                 505                 510

Val His Pro Glu Ser Gly Gly Arg Gln His Val Glu Val Arg Ala Val
        515                 520                 525

Gly Val Ser His Gly Gly
        530

<210> SEQ ID NO 35
<211> LENGTH: 4093
<212> TYPE: DNA
<213> ORGANISM: Glycine max

<400> SEQUENCE: 35
```

| | | | |
|---|---|---|---|
| gattccggat cagtttccgt tcagtggttc acagatgcta taaccaatag tcatcatctt | | | 60 |
| cagaaaaaaa ccacctttt ttgccattct gagctcaccg agctacccaa tgcgattttg | | | 120 |
| attcgcgggc ttttcatttc tgtataaatc tgcaatcttt gaggaaaata acgtaacccc | | | 180 |
| atctgtttat aatcatatgg ggcacaagtg aacggaaact ctcgaggaaa ttgaggtttg | | | 240 |
| aagcttgtaa cgcatcctag aatattatgt ctttgcttcg acggagaaaa gggtcggaac | | | 300 |
| cggaaaaggg tccgagcccg agttcggagc caaaggtttt aagcgaagac gagacagaag | | | 360 |
| atgataagaa taataagaag aataagaaga agagagatga ggtgggggag aagaagaaga | | | 420 |
| acaaatggtc atgcttcgat agctgttgtt ggtgggtggg gtgcatttgc acattgtggt | | | 480 |
| gttttcttct gtttctgtat cagatgatgc cttcttcgat tcctcagtat gtgaccgagg | | | 540 |
| ccttcactgg gccatgccg gacccaccgg gcctcaaact caagaaggaa ggactcaagg | | | 600 |
| tgaagcaccc tgtggttttt gtgcccggga ttgtcactgg ggggcttgaa ctgtgggagg | | | 660 |
| gtcacctgtg tgctgagggg ttgttcagga acgcttatg gggtggtacc ttcggagaag | | | 720 |
| tttataaaag accttcatgc tgggtggatc acatgtcact ggacaatgaa acaggattgg | | | 780 |
| atccaccagg gataagagtt aggcctgtct ctggacttgt agctgctgat tactttgctg | | | 840 |
| caggatactt tgtatgggca gtgctaattg ctaacttggc acgcattggt tatgaagaaa | | | 900 |
| aaactatgta catggctgca tatgattgga gaatagcatt tcagaacact gaggtgaggg | | | 960 |
| atcaaacact aagtcggata aaaagcaaca tagaacttat ggttgctact aatggtggaa | | | 1020 |
| ataaggcagt tattattcca cattcaatgg gggtcttgta ctttcttcat tttatgaagt | | | 1080 |
| gggttgaagc accagctcca actggtggtg gaggaggacc agattggtgc tccacatata | | | 1140 |
| taaaggcagt tgtaaacatt ggtggaccat ttttaggtgt tcccaaggct atagcagggc | | | 1200 |
| ttttctcagc tgaggcccgg gatattgctg ttgctaggac aatagctcca ggattttag | | | 1260 |
| ataacgatct gtttcgcatt caaacattgc aacatgtaat gaagatgacc cgtacttggg | | | 1320 |
| actcaacaat gtcaatgata ccaagaggag agatactat atggggtggt cttgattggt | | | 1380 |
| caccagaaga aggctatcac cctagccaga gaaagcacag caataacaat actcagttga | | | 1440 |
| aagaccacga aacaaatcaa acaaatttg tcaactatgg aagaatgata tcatttggca | | | 1500 |
| gagatgtggc cgaggcacac tcccctgaga ttcagatgac tgacttccgg ggtgctatca | | | 1560 |
| agggtcgcag tattgcaaat accacttgtc gtgatgtgtg gactgaatac catgaaatgg | | | 1620 |
| gatttgaagg agtgagagca gttgctgaac ataaagttta cacagctggc tcagtcgttg | | | 1680 |

-continued

| | |
|---|---|
| acctccttca atttgttgct ccaaagatga tggctcgtgg tagtgctcat ttctcttatg | 1740 |
| gaattgctga caatttggat gaccctaaat ataatcacta caagtattgg tcaaacccct | 1800 |
| tggaaacaaa attaccaaat gctcctgata tggaaatctt ctctatgtat ggagttggct | 1860 |
| tacctactga aagatcttat atttacaagt taactccctt tgccgagtgt tacattcctt | 1920 |
| ttgaaattga caccacacaa gatggtggta gcgatgaaga tagctgtctg caaggtggag | 1980 |
| tctacactgt tgatggggat gagactgtgc cggttctaag ttcaggcttc atgtgtgcta | 2040 |
| aaggttggcg cggaaaaaca agattcaacc catccggtat ccgcacctac gttagagaat | 2100 |
| atgatcattc tcctccagcc aaccttctag agggaagggg cacacaaagt ggtgctcacg | 2160 |
| ttgacatcat gggaaatttt gcattgattg aggatgttat aagagtggct gctggagcca | 2220 |
| aaggagaaga tctaggaggt gataaagtgt attctgatat cttcaagtgg tctgagaaaa | 2280 |
| tcaagttacc cctatgaatg aagcccaatg cacttccaca gttccactca gacacttctc | 2340 |
| ttgaacccct ttaaggatca gatcaggcta tataatttt ttgcagtata ttttcactgc | 2400 |
| caccagagtt ctgtaagttg cacttattag aattgctggt tctgctgatc aaattccagt | 2460 |
| tccatggagg ggtgaactat gcgaattggt tatattgtaa gagcttgtat tgaacatttt | 2520 |
| tgttattaaa gtaaggattt gatttgtcat ctctgagcaa cctggccagg ggcattattc | 2580 |
| ttaataagtt cagctggtta gttacgaaaa aaaaaaaaa aaaataggtg tggattttat | 2640 |
| gtcagaaaat gtgcgtgcca tccttgatca agctggtttc agtgaggttg gcgtgtatag | 2700 |
| gatgtcaaat gagcaaattg gatgttctct ggctgatgcg gcagctactc gtacttacat | 2760 |
| ggaatatctt acagctgctt ctaggtctac ttctttgcat gtcatataca ttaacactaa | 2820 |
| gttagagaca aaggcatatg ctcatgaact tgtgcctaca ataacctgta cttcatcaaa | 2880 |
| tgttgtccag actatcctac aggcatttgc tcaagttcca gatttgagca tattttatgg | 2940 |
| acctgattct tacatgggtg caaatatcaa agatttgttc caacaaatga caaaaatgac | 3000 |
| tgatgaagag attgctgcaa tacatcctga gcacagtcaa gactctatta gatcattact | 3060 |
| acctcgactt cactattttc aggatggaac gtgcattgtt caccatctat ttggccatga | 3120 |
| ggttgtggag aagataaaag aaatgtactg tgatgcattc cttactgccc atcttgaggt | 3180 |
| acctggagag atgttttcat ggcaatgga agcaaagaga aggggaatgg gtgtagtagg | 3240 |
| ctccacaaag aatatttgg atttcataaa ggacagggtt caggaagctt tggatagaaa | 3300 |
| tatagatgat catctccaat ttgttttagg aacagaatct gggatggtga cttcaattgt | 3360 |
| ggcaacagtt cgtagtttgt tggagcctgt gaagtcctct tctgaaagag caaaagttac | 3420 |
| tgttgaaata gtcttccag tttcatcaga ctcaatctca acgaccacct caagtttatc | 3480 |
| ctccggcctt cagactgcca agtgggtga tatcatactt cctgttgtac caggaatagc | 3540 |
| tagcggggag ggctgttcaa ttcatggtgg ctgtgcatct tgtccataca tgaagatgaa | 3600 |
| ttctcttggc tcactcctga agttagcaa tcacctaccc gatgaagaaa atatccttc | 3660 |
| tgcatacaag gcagagcgat ttaagttgca aacaccgaat ggcagatcag tggcagatgt | 3720 |
| tggatgtgaa cctatttgc acatgaggaa cttccaggct actaaaaagc ttccagagaa | 3780 |
| gcttgttgat cagattcttc gtccccaaca cagttgaagg ttgatgtgat aaagttgaga | 3840 |
| ataatgtgg tgatgtgaag aagacagaaa tttgtggtgc tgtcttgtga gcaattccaa | 3900 |
| gtagcaacta cagcaaaagt taggtccgtg caagggcttt gcttatagca tggtaatagt | 3960 |
| tgatacaacc agatttgttg tatgatagtt tcccttcgca taggggactt ctaatttatt | 4020 | tagataagat gacattatag agttcgatat caatatagag aaataaatga actagaaaaa    4080 aaaaaaaaaa aaa                                                      4093

<210> SEQ ID NO 36
<211> LENGTH: 676
<212> TYPE: PRT
<213> ORGANISM: Glycine max

<400> SEQUENCE: 36

Met Ser Leu Leu Arg Arg Arg Lys Gly Ser Glu Pro Glu Lys Gly Pro
 1               5                  10                  15

Ser Pro Ser Ser Glu Pro Lys Val Leu Ser Glu Asp Glu Thr Glu Asp
            20                  25                  30

Asp Lys Asn Asn Lys Lys Asn Lys Lys Arg Asp Glu Val Gly Glu
        35                  40                  45

Lys Lys Lys Asn Lys Trp Ser Cys Phe Asp Ser Cys Cys Trp Trp Val
 50                  55                  60

Gly Cys Ile Cys Thr Leu Trp Cys Phe Leu Leu Phe Leu Tyr Gln Met
 65                  70                  75                  80

Met Pro Ser Ser Ile Pro Gln Tyr Val Thr Glu Ala Phe Thr Gly Pro
            85                  90                  95

Met Pro Asp Pro Pro Gly Leu Lys Leu Lys Lys Glu Gly Leu Lys Val
            100                 105                 110

Lys His Pro Val Val Phe Val Pro Gly Ile Val Thr Gly Gly Leu Glu
        115                 120                 125

Leu Trp Glu Gly His Leu Cys Ala Glu Gly Leu Phe Arg Lys Arg Leu
 130                 135                 140

Trp Gly Gly Thr Phe Gly Glu Val Tyr Lys Arg Pro Ser Cys Trp Val
145                 150                 155                 160

Asp His Met Ser Leu Asp Asn Glu Thr Gly Leu Asp Pro Pro Gly Ile
            165                 170                 175

Arg Val Arg Pro Val Ser Gly Leu Val Ala Ala Asp Tyr Phe Ala Ala
        180                 185                 190

Gly Tyr Phe Val Trp Ala Val Leu Ile Ala Asn Leu Ala Arg Ile Gly
        195                 200                 205

Tyr Glu Glu Lys Thr Met Tyr Met Ala Ala Tyr Asp Trp Arg Ile Ala
 210                 215                 220

Phe Gln Asn Thr Glu Val Arg Asp Gln Thr Leu Ser Arg Ile Lys Ser
225                 230                 235                 240

Asn Ile Glu Leu Met Val Ala Thr Asn Gly Gly Asn Lys Ala Val Ile
            245                 250                 255

Ile Pro His Ser Met Gly Val Leu Tyr Phe Leu His Phe Met Lys Trp
        260                 265                 270

Val Glu Ala Pro Ala Pro Thr Gly Gly Gly Gly Pro Asp Trp Cys
        275                 280                 285

Ser Thr Tyr Ile Lys Ala Val Val Asn Ile Gly Gly Pro Phe Leu Gly
        290                 295                 300

Val Pro Lys Ala Ile Ala Gly Leu Phe Ser Ala Glu Ala Arg Asp Ile
305                 310                 315                 320

Ala Val Ala Arg Thr Ile Ala Pro Gly Phe Leu Asp Asn Asp Leu Phe
            325                 330                 335

Arg Ile Gln Thr Leu Gln His Val Met Lys Met Thr Arg Thr Trp Asp
        340                 345                 350

Ser Thr Met Ser Met Ile Pro Arg Gly Gly Asp Thr Ile Trp Gly Gly

-continued

```
               355                 360                 365
Leu Asp Trp Ser Pro Glu Glu Gly Tyr His Pro Ser Gln Arg Lys His
    370                 375                 380
Ser Asn Asn Thr Gln Leu Lys Asp His Glu Thr Asn Gln Thr Asn
385                 390                 395                 400
Phe Val Asn Tyr Gly Arg Met Ile Ser Phe Gly Arg Asp Val Ala Glu
                405                 410                 415
Ala His Ser Pro Glu Ile Gln Met Thr Asp Phe Arg Gly Ala Ile Lys
                420                 425                 430
Gly Arg Ser Ile Ala Asn Thr Thr Cys Arg Asp Val Trp Thr Glu Tyr
                435                 440                 445
His Glu Met Gly Phe Glu Gly Val Arg Ala Val Ala Glu His Lys Val
    450                 455                 460
Tyr Thr Ala Gly Ser Val Val Asp Leu Leu Gln Phe Val Ala Pro Lys
465                 470                 475                 480
Met Met Ala Arg Gly Ser Ala His Phe Ser Tyr Gly Ile Ala Asp Asn
                485                 490                 495
Leu Asp Asp Pro Lys Tyr Asn His Tyr Lys Tyr Trp Ser Asn Pro Leu
                500                 505                 510
Glu Thr Lys Leu Pro Asn Ala Pro Asp Met Glu Ile Phe Ser Met Tyr
            515                 520                 525
Gly Val Gly Leu Pro Thr Glu Arg Ser Tyr Ile Tyr Lys Leu Thr Pro
            530                 535                 540
Phe Ala Glu Cys Tyr Ile Pro Phe Glu Ile Asp Thr Thr Gln Asp Gly
545                 550                 555                 560
Gly Ser Asp Glu Asp Ser Cys Leu Gln Gly Gly Val Tyr Thr Val Asp
                565                 570                 575
Gly Asp Glu Thr Val Pro Val Leu Ser Ser Gly Phe Met Cys Ala Lys
                580                 585                 590
Gly Trp Arg Gly Lys Thr Arg Phe Asn Pro Ser Gly Ile Arg Thr Tyr
            595                 600                 605
Val Arg Glu Tyr Asp His Ser Pro Pro Ala Asn Leu Leu Glu Gly Arg
    610                 615                 620
Gly Thr Gln Ser Gly Ala His Val Asp Ile Met Gly Asn Phe Ala Leu
625                 630                 635                 640
Ile Glu Asp Val Ile Arg Val Ala Ala Gly Ala Lys Gly Glu Asp Leu
                645                 650                 655
Gly Gly Asp Lys Val Tyr Ser Asp Ile Phe Lys Trp Ser Glu Lys Ile
            660                 665                 670
Lys Leu Pro Leu
        675
```